United States Patent
Chudova et al.

(10) Patent No.: US 10,741,269 B2
(45) Date of Patent: *Aug. 11, 2020

(54) METHOD FOR IMPROVING THE SENSITIVITY OF DETECTION IN DETERMINING COPY NUMBER VARIATIONS

(71) Applicant: Verinata Health, Inc., San Diego, CA (US)

(72) Inventors: Darya I. Chudova, San Jose, CA (US); Diana Abdueva, Orinda, CA (US); Richard P. Rava, Redwood City, CA (US)

(73) Assignee: Verinata Health, Inc., San Diego, CA (US)

(*) Notice: Subject to any disclaimer, the term of this patent is extended or adjusted under 35 U.S.C. 154(b) by 836 days.

This patent is subject to a terminal disclaimer.

(21) Appl. No.: 15/031,246

(22) PCT Filed: Oct. 21, 2014

(86) PCT No.: PCT/US2014/061635
§ 371 (c)(1),
(2) Date: Apr. 21, 2016

(87) PCT Pub. No.: WO2015/061359
PCT Pub. Date: Apr. 30, 2015

(65) Prior Publication Data
US 2016/0239604 A1    Aug. 18, 2016

Related U.S. Application Data

(60) Provisional application No. 61/893,830, filed on Oct. 21, 2013.

(51) Int. Cl.
*G16B 25/00* (2019.01)
*G16H 50/20* (2018.01)

(52) U.S. Cl.
CPC .............. *G16B 25/00* (2019.02); *G16H 50/20* (2018.01)

(58) Field of Classification Search
None
See application file for complete search history.

(56) References Cited

U.S. PATENT DOCUMENTS

| | | | |
|---|---|---|---|
| 7,601,499 B2 | 10/2009 | Berka et al. | |
| 8,195,415 B2 | 6/2012 | Fan et al. | |
| 8,296,076 B2 | 10/2012 | Fan et al. | |
| 8,620,593 B2 | 12/2013 | Lo et al. | |
| 10,095,831 B2 | 10/2018 | Duenwald et al. | |
| 10,318,704 B2 | 6/2019 | Chudova et al. | |
| 2010/0112575 A1 | 5/2010 | Fan et al. | |
| 2010/0216153 A1 | 8/2010 | Lapidus et al. | |
| 2011/0177517 A1 | 7/2011 | Rava et al. | |
| 2011/0319272 A1 | 12/2011 | Fan et al. | |
| 2012/0053063 A1 | 3/2012 | Rigatti et al. | |
| 2012/0095697 A1 | 4/2012 | Halpern et al. | |
| 2013/0022977 A1 | 1/2013 | Lapidus et al. | |
| 2013/0029852 A1 | 1/2013 | Rava et al. | |
| 2013/0085681 A1 | 4/2013 | Deciu et al. | |
| 2013/0130921 A1 | 5/2013 | Gao et al. | |
| 2013/0150253 A1 | 6/2013 | Deciu et al. | |
| 2013/0237431 A1 | 9/2013 | Lo et al. | |
| 2013/0310260 A1 | 11/2013 | Kim et al. | |
| 2014/0038830 A1 | 2/2014 | Srinivasan et al. | |
| 2014/0051154 A1 | 2/2014 | Hyland et al. | |
| 2014/0180594 A1 | 6/2014 | Kim et al. | |
| 2014/0371078 A1 | 12/2014 | Abdueva | |
| 2015/0126379 A1 | 5/2015 | Liang et al. | |
| 2016/0019338 A1 | 1/2016 | Chudova et al. | |
| 2016/0194703 A1 | 7/2016 | Rava et al. | |
| 2016/0210405 A1 | 7/2016 | Rava et al. | |
| 2017/0220735 A1 | 8/2017 | Duenwald et al. | |
| 2017/0362638 A1 | 12/2017 | Chudova et al. | |
| 2018/0049770 A1 | 2/2018 | Zitnick et al. | |

(Continued)

FOREIGN PATENT DOCUMENTS

| | | |
|---|---|---|
| CA | 2878246 | 1/2014 |
| CA | 2922005 A1 | 4/2014 |
| EP | 2 334 812 A2 | 6/2011 |

(Continued)

OTHER PUBLICATIONS

U.S. Appl. No. 62/091,380, filed Dec. 12, 2014, Chudova et al.
U.S. Appl. No. 62/290,891, filed Feb. 3, 2016, Duenwald et al.
PCT International Search Report and Written Opinion dated Jan. 29, 2015 issued in PCT Application No. PCT/US2014/061635.
PCT International Preliminary Report on Patentability and Written Opinion dated May 6, 2016 issued in PCT Application No. PCT/US2014/061635.
PCT International Search Report and Written Opinion dated Aug. 11, 2015 issued in PCT Application No. PCT/US2015/033403.

(Continued)

*Primary Examiner* — Nancy J Leith
(74) *Attorney, Agent, or Firm* — Weaver Austin Villeneuve & Sampson LLP

(57) ABSTRACT

Disclosed are methods for determining copy number variation (CNV) known or suspected to be associated with a variety of medical conditions. In some embodiments, methods are provided for determining copy number variation (CNV) of fetuses using maternal samples comprising maternal and fetal cell free DNA. In some embodiments, methods are provided for determining CNVs known or suspected to be associated with a variety of medical conditions. Some embodiments disclosed herein provide methods to improve the sensitivity and/or specificity of sequence data analysis by removing within-sample GC-content bias. In some embodiments, removal of within-sample GC-content bias is based on sequence data corrected for systematic variation common across unaffected training samples. Also disclosed are systems and computer program products for evaluation of CNV of sequences of interest.

39 Claims, 20 Drawing Sheets

(56) References Cited

U.S. PATENT DOCUMENTS

| | | |
|---|---|---|
| 2018/0307796 A1 | 10/2018 | Jiang et al. |
| 2019/0065676 A1 | 2/2019 | Duenwald et al. |

FOREIGN PATENT DOCUMENTS

| | | | |
|---|---|---|---|
| EP | 2 536 852 A2 | 12/2012 | |
| EP | 2 561 103 A1 | 2/2013 | |
| EP | 2 562 268 A1 | 2/2013 | |
| EP | 2 772 549 A1 | 9/2014 | |
| EP | 3 202 915 A1 | 8/2017 | |
| JP | 2010/534069 A | 11/2010 | |
| JP | 2016/526380 A | 9/2016 | |
| JP | 2016/533173 A | 10/2016 | |
| WO | WO 2009/051842 A2 | 4/2009 | |
| WO | WO 2011/102998 A2 | 8/2011 | |
| WO | WO 2012/071621 A1 | 6/2012 | |
| WO | WO 2013/000100 A1 | 1/2013 | |
| WO | WO 2013/015793 A1 | 1/2013 | |
| WO | WO 2013/052913 A2 | 4/2013 | |
| WO | WO 2013/109981 A1 | 7/2013 | |
| WO | WO 2013/138527 A1 | 9/2013 | |
| WO | WO 2014/014498 A1 | 1/2014 | |
| WO | WO 2014/015319 A1 | 1/2014 | |
| WO | WO 2014/039556 A1 | 3/2014 | |
| WO | WO 2013/097062 A1 | 9/2014 | |
| WO | WO 2014/149134 A2 | 9/2014 | |
| WO | WO 2015/061359 A1 | 4/2015 | |
| WO | WO 2015/184404 A1 | 12/2015 | |
| WO | WO 2016/094853 A1 | 6/2016 | |
| WO | WO 2017/136059 A1 | 8/2017 | |

OTHER PUBLICATIONS

PCT International Search Report and Written Opinion dated Mar. 8, 2016 issued in PCT Application No. PCT/US2015/065362.
Bianchi et al. (Feb. 27, 2014) "DNA Sequencing versus Standard Prenatal Aneuploidy Screening," *The New England Journal of Medicine*, 370(9):799-808.
Chen et al. (Jul. 6, 2011) "Noninvasive Prenatal Diagnosis of Fetal Trisomy 18 and Trisomy 13 by Maternal Plasma DNA Sequencing," *PLOS ONE*, 6(7):e21791, 7 pages.
Fan H.C. et al. (Oct. 21, 2008) "Noninvasive diagnosis of fetal aneuploidy by shotgun sequencing DNA from maternal blood," *Proceedings of the National Academy of Sciences, National Academy of Sciences*, US, 105(42):16266-16271.
Fan et al. (2010) "Analysis of the Size Distributions of Fetal and Maternal Cell-Free DNA by Paired-End Sequencing," *Clinical Chemistry*, 56:8 pages.
Hahn et al. (2010) "Cell-Free DNA in Maternal Plasma: Has the Size-Distribution Puzzle Been Solved?" *Clinical Chemistry*, 56:8, 1210-1211.
Jensen et al. (Jul. 1, 2012) "Detection of Microdeletion 22q11.2 in a Fetus by Next-Generation Sequencing of Maternal Plasma," *Clinical Chemistry*, 58(7):1148-1151.
Magi et al. (Dec. 23, 2011) "Read count approach for DNA copy number variants detection", *Bioinformatics*, 28(4):470-478.
Rava et al. (2014) "Circulating Fetal Cell-Free DNA Fractions Differ in Autosomal Aneuploidies and Monosomy X," *Clinical Chemistry*,60:1, 8 pages.
Salani et al. (2007) "Measurement of Cyclin E Genomic Copy Number and Strand Length in Cell-Free DNA Distinguish Malignant versus Benign Effusions," *Clin Cancer Res*. 13(19):5805-5809.
Yu et al. (2014) "Size-based molecular diagnostics using plasma DNA for noninvasive prenatal testing," *PNAS Early Edition*, 6 pages.
Van der Laan et al. "A new algorithm for hybrid hierarchical clustering with visualizaiton and the bootstrap," *Hierarchical Ordered Partitioning and Collapsing Hybrid (HOPACH)*, 30pp, 2003.
U.S. Office Action dated May 30, 2017 issued in U.S. Appl. No. 15/382,508.
U.S. Office Action dated Jan. 22, 2018 issued in U.S. Appl. No. 15/382,508.
U.S. Notice of Allowance dated Aug. 27, 2018 issued in U.S. Appl. No. 15/382,508.
U.S. Office Action dated Dec. 26, 2017 issued in U.S. Appl. No. 14/726,183.
U.S. Final Office Action dated Oct. 1, 2018 issued in U.S. Appl. No. 14/726,183.
Chinese First Office Action dated May 3, 2018 issued in Application No. CN 201480070158.4.
Israel First Office Action dated Aug. 22, 2018 issued in Application No. IL 245177.
Japanese First Office Action dated Sep. 27, 2018 issued in Application No. JP 2016-525007.
PCT International Preliminary Report on Patentability and Written Opinion dated Dec. 15, 2016 issued in Application No. PCT/US2015/033403.
European Examination Report dated Mar. 23, 2018 issued in Application No. EP 15728356.5.
Thailand First Office Action dated Mar. 29, 2018 issued in Application No. TH 1601007189.
Canadian Office Action and Examination Search Report dated Feb. 21, 2018 issued in Application No. CA 2,970,501.
PCT International Preliminary Report on Patentability and Written Opinion dated Jun. 22, 2017 issued in Application No. PCT/US2015/065362.
European Examination Search Report dated Oct. 6, 2017 issued in Application No. EP 15819994.3.
PCT Invitation to Pay Additional Fees and Partial International Search dated Apr. 26, 2017 issued in Application No. PCT/US2016/067886.
PCT International Search Report and Written Opinion dated Jul. 13, 2017 issued in Application No. PCT/US2016/067886.
International Preliminary Report on Patentability dated Aug. 16, 2018 issued in Application No. PCT/US16/67886.
European Extended Search Report dated Jun. 28, 2017 issued in Application No. EP 16 20 5580.0.
European Examination Report dated Jul. 21, 2017 issued in Application No. EP 16 20 5580.0.
European Examination Report dated Apr. 5, 2018 issued in Application No. EP 16 20 5580.0.
Chaing et al., "High Resolution mapping of copy-number alterations with massively parallel sequencing," Nature Methods, vol. 6, No. 1, Jan. 2009, pp. 99-103.
Jiang, et al., "Noninvasive Fetal Trisomy (NIFTY) test: an advanced noninvasive prenatal diagnosis methodology for fetal autosomal and sex chromosomal aneuploidies," BMC Medical Genomics, vol. 5, No. 57, Dec. 1, 2012, pp. 1-11. <doi:10.1186/1755-8794-5-57>.
Shendure, J., et al., "Next-generation DNA sequencing," Nature Biotechnology, vol. 26, No. 10, Oct. 2008, pp. 1135-1145. <doi:10.1038/nbt1486>.
U.S. Appl. No. 16/119,993, filed Aug. 31, 2018, Duenwald et al.
U.S. Notice of Allowance dated Jan. 30, 2019 issued in U.S. Appl. No. 14/726,183.
Australia First Office Action dated Apr. 26, 2019 issued in Application No. AU 2014340239.
European First Office Action dated May 10, 2019 issued in Application No. EP 14796611.3.
Japanese Decision to Grant Patent dated May 22, 2019 issued in Application No. JP 2016-525007.
Chinese Second Office Actiond dated Dec. 5, 2018 issued in Application No. CN 201480070158.4.
Thailand First Office Action dated Feb. 17, 2019 issued in Application No. TH 1601002280.
Japanese First Office Action dated Apr. 18, 2019 issued in Application No. JP 2017-515036.
European Second Office Action dated Dec. 3, 2018 issued in Application No. EP 15728356.5.
Australia First Office Action dated Jan. 8, 2019 issued in Application No. AU 2016391100.
Canadian First Office Action dated Feb. 28, 2019 issued in Application No. CA 3,013,572.

(56) References Cited

OTHER PUBLICATIONS

Canadian Second Office Action dated Jun. 30, 2019 issued in Application No. CA 3,013,572.
Chinese First Office Action dated Apr. 4, 2019 issued in Application No. CN 201680084307.1.
Eurasian First Office dated Jan. 30, 2019 issued in Application No. EA 201891580.
Extended European Search Report dated May 10, 2019 issued in Application No. EP 19161739.8.
Israel First Office Action dated Nov. 6, 2018 issued in Application No. IL 260938.
Israel Second Office Action dated Apr. 10, 2019 issued in Application No. IL 260938.
Singapore Notice of Eligibility for Grant dated Mar. 26, 2019 issued in Application No. SG 11201806595U.
Taiwanese First Office Action dated Nov. 30, 2018 issued in Application No. TW 105142299.
New Zealand First Examination Report dated Dec. 18, 2018 issued in Application No. NZ 745637.
Korean First Office Action dated Jun. 13, 2019 issued in Application No. KR 10-2018-7025212.
Benjamini, et al. (Feb. 9, 2012) "Summarizing and correcting the GC content bias in high-throughput sequencing," Nucleic Acids Research, 2012, vol. 40, No. 10, pp. 1-14.
U.S. Appl. No. 16/395,066, filed Apr. 25, 2019, Chudova et al.
Korean First Office Action dated Feb. 19, 2020 issued in Application No. KR 10-2019-7034142.
Taiwanese First Office Action dated Apr. 6, 2020 issued in Application No. TW 108113871.
European Extended Search Report dated Jun. 10, 2020 issued in Application No. EP 20164915.9.
Chinese Third Office Action dated May 22, 2020 issued in Application No. AU 2019203491.
New Zealand First Examination Report dated May 20, 2020 issued in Application No. NZ 752319.

METHOD FOR IMPROVING THE SENSITIVITY OF DETECTION IN DETERMINING COPY NUMBER VARIATIONS

CROSS-REFERENCE TO RELATED APPLICATIONS

This application is filed pursuant to 35 U.S.C. § 371 as a United States National Phase Application of International Application No. PCT/US2014/061635, entitled: METHOD FOR IMPROVING THE SENSITIVITY OF DETECTION IN DETERMINING COPY NUMBER VARIATIONS, filed Oct. 21, 2014, which claims benefits under 35 U.S.C. § 119(e) to U.S. Provisional Patent Application No. 61/893, 830, entitled: METHOD FOR IMPROVING THE SENSITIVITY OF DETECTION IN DETERMINING COPY NUMBER VARIATIONS, filed Oct. 21, 2013. All of the above prior applications are herein incorporated by reference in their entireties for all purposes.

BACKGROUND

One of the critical endeavors in human medical research is the discovery of genetic abnormalities that produce adverse health consequences. In many cases, specific genes and/or critical diagnostic markers have been identified in portions of the genome that are present at abnormal copy numbers. For example, in prenatal diagnosis, extra or missing copies of whole chromosomes are frequently occurring genetic lesions. In cancer, deletion or multiplication of copies of whole chromosomes or chromosomal segments, and higher level amplifications of specific regions of the genome, are common occurrences.

Most information about copy number variation (CNV) has been provided by cytogenetic resolution that has permitted recognition of structural abnormalities. Conventional procedures for genetic screening and biological dosimetry have utilized invasive procedures, e.g., amniocentesis, cordocentesis, or chorionic villus sampling (CVS), to obtain cells for the analysis of karyotypes. Recognizing the need for more rapid testing methods that do not require cell culture, fluorescence in situ hybridization (FISH), quantitative fluorescence PCR (QF-PCR) and array-Comparative Genomic Hybridization (array-CGH) have been developed as molecular-cytogenetic methods for the analysis of copy number variations.

One of the critical endeavors in human medical research is the discovery of genetic abnormalities that produce adverse health consequences. In many cases, specific genes and/or critical diagnostic markers have been identified in portions of the genome that are present at abnormal copy numbers. For example, in prenatal diagnosis, extra or missing copies of whole chromosomes are frequently occurring genetic lesions. In cancer, deletion or multiplication of copies of whole chromosomes or chromosomal segments, and higher level amplifications of specific regions of the genome, are common occurrences.

Most information about copy number variation (CNV) has been provided by cytogenetic resolution that has permitted recognition of structural abnormalities. Conventional procedures for genetic screening and biological dosimetry have utilized invasive procedures, e.g., amniocentesis, cordocentesis, or chorionic villus sampling (CVS), to obtain cells for the analysis of karyotypes. Recognizing the need for more rapid testing methods that do not require cell culture, fluorescence in situ hybridization (FISH), quantitative fluorescence PCR (QF-PCR) and array-Comparative Genomic Hybridization (array-CGH) have been developed as molecular-cytogenetic methods for the analysis of copy number variations.

The advent of technologies that allow for sequencing entire genomes in relatively short time, and the discovery of circulating cell-free DNA (cfDNA) have provided the opportunity to compare genetic material originating from one chromosome to be compared to that of another without the risks associated with invasive sampling methods, which provides a tool to diagnose various kinds of copy number variations of genetic sequences of interest.

Diagnosis of copy number variation (CNV) in some applications involves heightened technical challenges. For instance, non-invasive prenatal diagnosis (NIPD) of CNV for fraternal multiple (or polyzygotic) pregnancy is more difficult than single pregnancy because the total fraction of fetal cfDNA does not change proportionally to the number of fetuses, lowering the fetal fraction of cfDNA by an order of the number of fetuses, which in turn reduces signal to noise ratio of in analysis. Additionally, Y chromosome based diagnosis such as gender identification is affected by limitations related to the Y chromosome. Specifically, coverage of the Y chromosome is lower than that of autosomes, and repeated sequences on the Y chromosome complicate mapping of reads to their correct location. Furthermore, some current sequencing protocols utilize ultra-short reads such as 25mer reads and tags, presenting yet another alignment challenge since 25mer tags are shorter than typical size of most ubiquitous repeatable elements. Some embodiments disclosed herein provide methods to improve the sensitivity and/or specificity in analyzing sequence data for evaluation of CNV.

Limitations of existing methods in noninvasive prenatal diagnostics, which include insufficient sensitivity stemming from the limited levels of cfDNA, and the sequencing bias of the technology stemming from the inherent nature of genomic information, underlie the continuing need for non-invasive methods that would provide any or all of the specificity, sensitivity, and applicability, to reliably diagnose copy number changes in a variety of clinical settings. Embodiments disclosed herein fulfill some of the above needs and in particular provides a reliable method that is applicable to the practice of noninvasive prenatal diagnostics.

SUMMARY

In some embodiments, methods are provided for determining copy number variation (CNV) of any fetal aneuploidy, and CNVs known or suspected to be associated with a variety of medical conditions. The methods include mechanism for reducing noise and error related to GC fluctuation of genomic sequences. CNV that can be determined according to the present method include trisomies and monosomies of any one or more of chromosomes 1-22, X and Y, other chromosomal polysomies, and deletions and/or duplications of segments of any one or more of the chromosomes.

Another embodiment provides a method for identifying copy number variation (CNV) of a nucleic acid sequence of interest, e.g., a clinically relevant sequence, in a test sample. The method assesses copy number variation of sequences of interest instead of complete chromosomes or segments of chromosomes.

In some embodiments, the method is implemented at a computer system that includes one or more processors and system memory to evaluate copy number of a nucleic acid sequence of interest in a test sample comprising nucleic acids of one or more genomes. The method includes: (a) providing sequence reads obtained by a nucleic acid sequencer from the test sample; (b) aligning the sequence reads of the test sample to a reference genome comprising the nucleic acid sequence of interest, thereby providing test sequence tags; (c) determining a coverage of the test sequence tags located in each bin, wherein the reference genome is divided into a plurality of bins; (d) providing a global profile for the nucleic acid sequence of interest, wherein the global profile comprises an expected coverage in each bin, and wherein the expected coverage is obtained from a training set of unaffected (e.g., diploid) training samples sequenced and aligned in substantially the same manner as the test sample, the expected coverage exhibiting variation from bin to bin; (e) adjusting the coverage of the test sequence tags using the expected coverage in each bin of at least the nucleic acid sequence of interest, thereby obtaining global-profile-corrected coverages for the nucleic acid sequence of interest; (f) adjusting the global-profile-corrected coverages based on a relation between GC content levels and the global-profile-corrected coverages, thereby obtaining sample-GC-corrected coverages for the nucleic acid sequence of interest; and (g) evaluating a copy number of the nucleic acid sequence of interest in the test sample based on the sample-GC-corrected coverages. In some embodiments, the coverage determined in step (c) is obtained after normalization for library depth differences. The library normalization may involve dividing the coverage by the total number of reads mapping to robust chromosomes expected to de diploid as described herein. Alternatively, the library depth normalization may involve dividing coverage by the number of reads mapping to the whole genome, thereby producing sequence a tag density ratio. In some embodiments, the sequencing data for a sample itself can be used to derive genomic regions estimated to have diploid coverage, and use those regions in library normalization. Library depth normalization is performed separately from other forms of normalization typically performed after (c), such as normalizing the global-profile-corrected coverage obtained in (f). Another form of "normalization" produces a "sequence dose" as described hereinafter.

In some embodiments, the method further involves, before operation (c) of determining coverages of bins, applying a sequence mask that excludes from consideration coverages in masked bins. In some embodiments, the sequence mask is obtained from sequence reads of a plurality of unaffected training samples. The sequence mask is obtained by aligning the sequence reads of the training set to the reference genome, thereby providing training sequence tags for the training samples. The method also involves dividing the reference genome into a plurality of bins and determining a coverage of training sequence tags in each bin for each training sample. The method further involves creating a sequence mask comprising unmasked and masked bins. Each masked bin has a distribution index exceeding a masking threshold, the distribution index relating to the distribution of coverages of the training samples. In some embodiments, the distribution index used to determine masked and unmasked bins is mathematically related to the variance of the coverages of the training samples, e.g., a coefficient of variation. The distribution index is implemented as a criterion for masking bins because a bin exhibiting a large variability or variance among the training samples has a high distribution index, and therefore is unreliable for use in characterizing copy number.

In some embodiments, the method first removes systematic variation common in the unaffected training samples (or a global profile) before creating or applying a sequence mask. This can be done by adjusting the coverage of the training sequence tags according to the expected coverage in each bin, thereby obtaining global-profile-corrected coverages of the training sequence tags in the bins, which are then used to create a sequence mask. In some embodiments, a normalized coverage quantity is used to calculate the mask. The normalized coverage quantity is the ratio of a coverage of a nucleic acid sequence of interest over a coverage of a normalizing sequence. In some embodiments, the masked bins on the nucleic acid sequence of interest have a first masking threshold and the masked bins on a normalizing sequence have a second masking threshold. In some embodiments, the combination of the first masking threshold and the second masking threshold provides a sequence mask that results in a lower variation of coverage over a region including the sequence of interest in unaffected samples than masks obtained using other thresholds. The variation of coverage reflects the sequence mask's ability to control variance across samples and runs, and thus a lower variation increases the separation between affected and unaffected samples. In some embodiments, the masking thresholds result in a small coefficient of variance of the coverages in validation samples and/or a large d' value in an ROC analysis.

In some embodiments, the sequence mask includes masked bins and unmasked bins defined by the distribution of mapping quality scores across training samples within the bins. The mapping quality scores are derived from aligning sequence reads of a plurality of unaffected training samples to the reference genome.

In some embodiments, the evaluating copy number of the nucleic acid sequence of interest in the test sample comprises calculating a sequence dose of the nucleic acid sequence of interest for the test sample using coverage information of a normalizing sequence. In some embodiments, calculating the sequence dose comprises dividing the coverage (e.g., sample-GC-corrected coverage) of the test sequence tags in the nucleic acid sequence of interest by the coverage of the test sequence tags in a normalizing sequence. Other methods may be used to calculate sequence dose, such as using a linear regression or a robust linear regression to model the normalized coverages of a sequence of interest from the normalized coverages of other normalizing regions of the genome.

In some embodiments, the normalizing sequence comprises one or more robust autosomes sequences or segments thereof. In some embodiments, the robust autosomes include all autosomes except for the chromosome(s) of interest. In some embodiments, the robust autosomes include all autosomes except for chr X, Y, 13, 18, and 21. In some embodiments, the robust autosomes include all autosomes except those determined from a sample to be deviating from a normal diploid state.

In some embodiments, the evaluating the copy number further includes calculating a normalized chromosome value or a normalized segment value of the nucleic acid sequence of interest for the test sample using coverage information of a normalizing sequence.

In some embodiments, the test sample includes a mixture of nucleic acids from two different genomes. In some embodiments, the test sample includes cfDNA molecules. In some embodiments, the test sample includes fetal and maternal cell-free nucleic acids. In some embodiments, the test sample includes fetal cell-free nucleic acids from two or more fetuses. In some embodiments, the test sample comprises nucleic acids (cellular genomic DNA and/or cfDNA) from cancerous and unaffected cells from the same subject.

In some embodiments, the evaluating copy number of the nucleic acid sequence of interest in the test sample involves determining the presence or absence of a complete or partial fetal aneuploidy.

In some embodiments, after operation (f) of obtaining sample-GC-corrected coverage, the method further involves removing outlier bins of sample-GC-corrected coverage from consideration in evaluation of CNV. In some embodiments, the outlier bins are bins whose median sample-GC-corrected coverage are more than about 3 median absolute deviation from the median of all the bins in each chromosome.

In some embodiments, the expected coverage in each bin is the median or mean across training samples. In some embodiments, coverage in training samples is corrected for GC content variation prior to computing the global profile as the median or mean normalized coverage.

In some implementations, coverages of the test sequence tags are adjusted by: (i) obtaining a mathematical relation between the coverage of the test sequence tags versus the expected coverage in a plurality of bins in one or more robust chromosomes or regions, and (ii) applying the mathematical relation to bins in the sequence of interest. In some implementations, the coverages in a test sample are corrected for variation using a linear relationship between the expected coverage values from unaffected training samples and coverage values for the test sample in robust chromosomes or other robust regions of the genome. The adjustment results in global-profile-corrected coverages. In some cases, the adjustment involves obtaining coverages for a test sample for a subset of bins in robust chromosomes or regions as follows:

$$y_a = \text{intercept} + \text{slope} * gwp_a$$

where ya is coverage of bin a for the test sample in one or more robust chromosomes or regions, and gwpa is the global profile for bin a for unaffected training samples. The process then computes a global-profile-corrected coverage zb for a sequence or region of interest as:

$$z_b = y_b/(\text{intercept} + \text{slope} * gwp_b) - 1$$

where yb is the observed coverage of bin b for the test sample in the sequence of interest (which may reside outside a robust chromosome or region), and gwpb is the global profile for bin b for unaffected training samples. The denominator (intercept+slope*gwpb) is the coverage for bin b that should be observed in unaffected test samples. In the case of a sequence of interest harboring a copy number variation, the observed coverage and hence the global-profile-corrected coverage value for bin b will deviate significantly from the coverage of an unaffected sample. For example, the corrected coverage zb would be proportional to fetal fraction in the case of trisomic sample for bins on the affected chromosome. This process normalizes within sample by computing intercept and slope on robust chromosomes, and then evaluates how a target chromosome (or other sequence of interest) deviates from a relationship (as described by the slope and the intercept) that holds for robust chromosomes within the same sample.

In some embodiments, the global-profile-corrected coverage of the test sequence tags from (e) comprise global-profile-corrected coverage of bins in the nucleic acid sequence of interest and global-profile-corrected coverage of bins in a normalizing sequence.

In some embodiments, adjusting the global-profile-corrected coverage in operation (f) includes: grouping bins in the reference genome into a plurality of GC groups, each GC group comprising multiple bins, wherein the multiple bins contain test sequence tags and have similar GC content; determining an expected value of the global-profile-corrected coverage for each GC group for a plurality of robust autosomes; and adjusting the global-profile-corrected coverage of the test sequence tags for each GC group based on the determined expected value of the same GC group, thereby obtaining the sample-GC-corrected coverage of the test sequence tags on the nucleic acid sequence of interest.

In some embodiments, the expected value of the global-profile-corrected coverage is the mean or the median of the coverage for the GC group of a plurality of robust autosomes. In some embodiments, adjusting the global-profile-corrected coverage of the test sequence tags is achieved by subtracting the expected value from the global-profile-corrected coverage.

In some embodiments, the adjusting the global-profile-corrected coverage in operation (f) involves fitting a linear or non-linear mathematical function to data points from a plurality of robust autosomes, wherein each data point relates a coverage value to a GC content value. The method then adjust a coverage by a value equals to the coverage value of the mathematical function at the GC content value of the bin under consideration. In some embodiments, the method subtracts the expected value from the global-profile-corrected coverage. In other embodiments, the method divides the coverage quantity by the expected value.

In some embodiments, methods for evaluating CNV also involve extracting cell free DNA from a plurality of unaffected individuals and/or the test sample. In some embodiments, the methods also involve sequencing nucleic acids from the test sample using a sequencer, thereby generating sequence reads of the test sample. In some embodiments, the sequence reads comprise sequences of about 20 to 50-bp from anywhere in the entire genome of an individual. In some embodiments, the sequence reads include bar-coded 25-mers.

In some embodiments, the coverages of the test sequence tags and the training sequence tags are based on non-excluded site counts (NES counts), wherein NES counts are the numbers of non-redundant and/or uniquely aligned sequence tags mapped to non-excluded sites.

In some embodiments, the nucleic acid sequence of interest is divided into bins of between about 1000 bp and 1,000,000 bp. In some embodiments, the bin size is about 100,000 bp. In some embodiments, the bin size is calculated with reference to the numbers of sequence reads of the test sample. In some embodiments, the numbers of sequence tags in each bin are at least about 1000 bp.

Some embodiments disclosed herein provide a method for creating a sequence mask for evaluation of copy number of a nucleic acid sequence of interest. The method includes: (a) providing, at the computer system, a training set comprising sequence reads from a plurality of unaffected training samples; (b) aligning the sequence reads of the training set to a reference genome comprising the nucleic acid sequence of interest, thereby providing training sequence tags for the training samples; (c) dividing the reference genome into a plurality of bins; (d) determining for each unaffected training sample a coverage of training sequence tags in each bin for each training sample; (e) determining, for each bin, an expected coverage of the training sequence tags across all training samples; (f) adjusting the coverage of the training sequence tags in each bin for each training sample according to the expected coverage in each bin, thereby obtaining global-profile-corrected coverages of the training sequence tags in the bins for each training sample; and (g) creating a sequence mask comprising unmasked and masked bins across the reference genome, wherein each masked bin has a distribution characteristic exceeding a masking threshold, and the distribution characteristic is provided for the adjusted coverages of the training sequence tags in the bin across training samples.

In some embodiments, the expected coverage determined in (e) for each bin include the median or mean of coverages of training samples. In some embodiments, the adjusting the coverage of the training sequence tags in operation (f) include subtracting the median or mean from each training sample's coverage of the training sequence tags for each bin. In some embodiments, the adjusting is done by dividing each training sample's coverage of the training sequence tags for each bin by the median or mean.

In some embodiments, the masked bins on the nucleic acid sequence of interest have a first masking threshold and the masked bins on a normalizing sequence have a second masking threshold. In some embodiments, the combination of the first masking threshold and the second masking threshold provides a sequence mask that results in a lower variation of coverage over a region including the sequence of interest in unaffected samples than masks obtained using other thresholds.

In some embodiments, the method for creating a sequence mask further involves, after (f) and before (g), adjusting the global-profile-corrected coverages for the bins of each training sample based on the relation between GC content level and the global-profile-corrected coverage existing in each training sample, thereby obtaining sample-GC-corrected coverages of the training sequence tags for each training sample.

In some embodiments, the adjustment of the global-profile-corrected coverages for each training sample involves: grouping all bins in the reference genome into a plurality of GC groups, each GC group comprising multiple bins having similar GC content; determining an expected value of the global-profile-corrected coverage for each GC group for a plurality of robust autosomes; and adjusting the global-profile-corrected coverage of the training sequence tags for each GC group based on the determined expected value of the same GC group, thereby obtaining the sample-GC-corrected coverage of the training sequence tags on the nucleic acid sequence of interest.

In some embodiments, the expected value of the global-profile-corrected coverage is the mean or the median of the coverage for the GC group of a plurality of robust autosomes. In some embodiments, adjusting the global-profile-corrected coverage of the training sequence tags involves subtracting the expected value from the global-profile-corrected coverage.

In some embodiments, the adjusting the global-profile-corrected coverages for each training sample involves: fitting a linear or non-linear mathematical function to data points from a plurality of robust autosomes, wherein each data point relates a coverage value to a GC content value. The method then adjusts the global-profile-corrected coverage of the training sequence tags in each bin based on an expected value of coverage for each bin, which equals to the coverage value of the mathematical function at the GC content value of the bin.

In some embodiments, adjusting the global-profile-corrected coverage of the training sequence tags comprises subtracting the expected value from the global-profile-corrected coverage. In other embodiments, the coverage is divided by the expected value.

In some embodiments, the test sample may be a maternal sample selected from blood, plasma, serum, urine and saliva samples. In any one of the embodiments, the test sample may be plasma sample. The nucleic acid molecules of the maternal sample are a mixture of fetal and maternal cell-free DNA molecules. Sequencing of the nucleic acids can be performed using next generation sequencing (NGS). In some embodiments, sequencing is massively parallel sequencing using sequencing-by-synthesis with reversible dye terminators. In other embodiments, sequencing is sequencing-by-ligation. In yet other embodiments, sequencing is single molecule sequencing. Optionally, an amplification step is performed prior to sequencing.

Another embodiment provides a method for identifying copy number variation (CNV) of a nucleic acid sequence of interest, e.g., a clinically relevant sequence, in a test sample. The method assesses copy number variation of sequences of interest instead of complete chromosomes or segments of chromosomes.

In certain embodiments embodied on a computer system, the number of sequence tags identified for each of the one or more chromosomes of interest or chromosome segments of interest is at least about 10,000, or at least about 100,000.

The disclosed embodiments also provide a computer program product including a non-transitory computer readable medium on which is provided program instructions for performing the recited operations and other computational operations described herein.

Some embodiments provide a system for evaluation of copy number of a nucleic acid sequence of interest in a test sample. The system includes a sequencer for receiving nucleic acids from the test sample providing nucleic acid sequence information from the sample, a processor; and one or more computer-readable storage media having stored thereon instructions for execution on said processor to evaluate copy number in the test sample using the method recited herein.

In some embodiments, a method additionally includes sequencing at least a portion of said nucleic acid molecules of said test sample to obtain said sequence information for said fetal and maternal nucleic acid molecules of said test sample. The sequencing may involve massively parallel sequencing on maternal and fetal nucleic acids from the maternal test sample to produce the sequence reads.

Although the examples herein concern humans and the language is primarily directed to human concerns, the concepts described herein are applicable to genomes from any plant or animal. These and other objects and features of the present disclosure will become more fully apparent from the following description and appended claims, or may be learned by the practice of the disclosure as set forth hereinafter.

INCORPORATION BY REFERENCE

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

DETAILED DESCRIPTION

Figure 1:
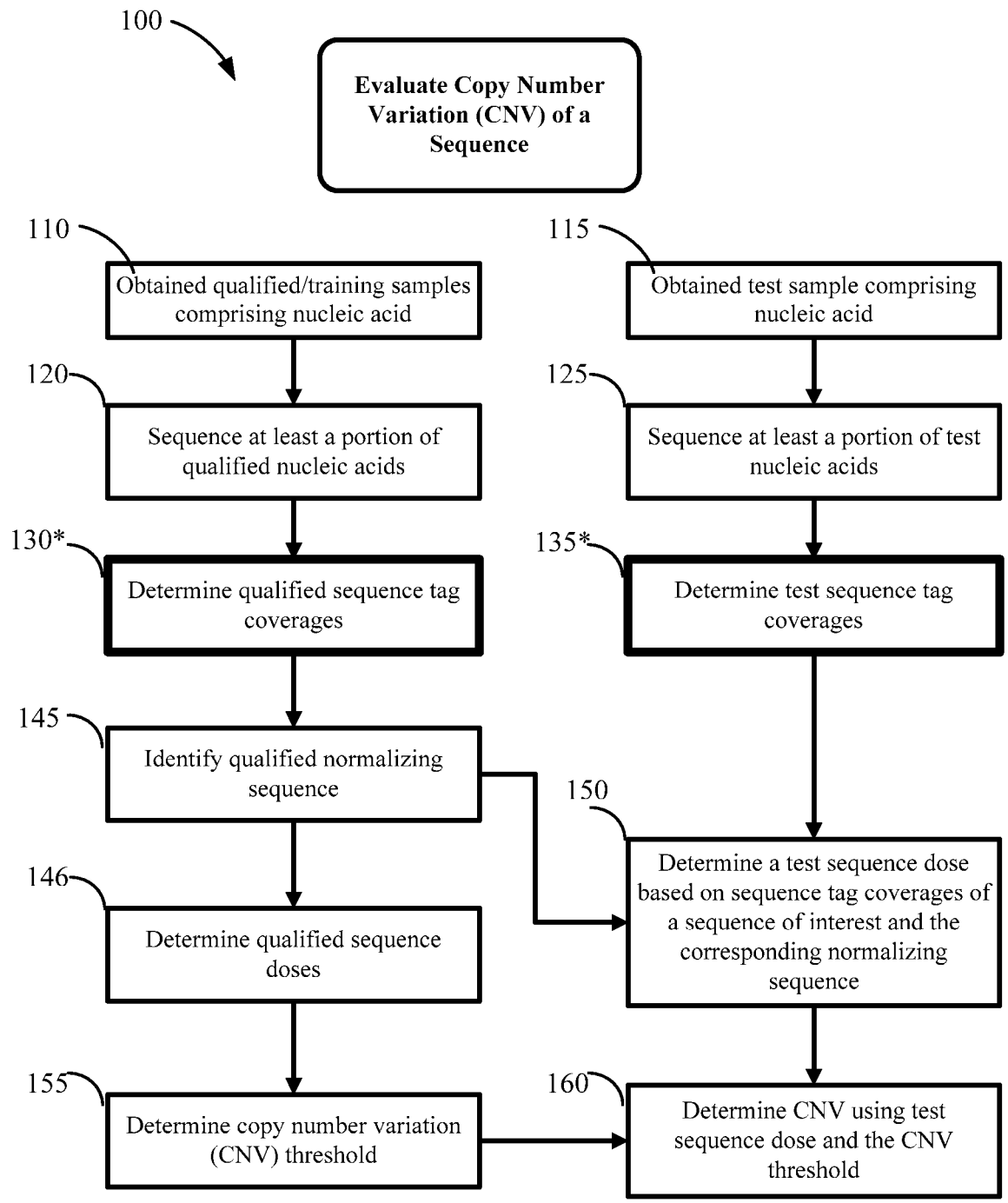
FIG. 1 is a flowchart of a method 100 for determining the presence or absence of a copy number variation in a test sample comprising a mixture of nucleic acids.

The disclosed embodiments concern methods, apparatus, and systems for evaluation of copy number of the Y chromosome in a test sample comprising fetal and maternal cell-free nucleic acids. In some embodiments, sequences of interest include genomic segment sequences ranging from, e.g., kilobases (kb) to megabases (Mb) to entire chromosomes that are known or are suspected to be associated with a genetic or a disease condition. In some embodiments, copy number of the Y chromosome is used to determine fetal gender. In some embodiments, CNV that can be determined according to the present method include monosomies and trisomies of sex chromosome Y (e.g. 47,XXY and 47,XYY), other polysomies of sex chromosomes such as tetrasomy and pentasomies (e.g. XXXXY and XYYYY), and deletions and/or duplications of segments of any one or more of the sex chromosomes. Other examples of sequences of interest include chromosomes associated with well-known aneuploidies, e.g., trisomy XXX, trisomy 21, and segments of chromosomes that are multiplied in diseases such as cancer, e.g., partial trisomy 8 in acute myeloid leukemia.

Unless otherwise indicated, the practice of the method and system disclosed herein involves conventional techniques and apparatus commonly used in molecular biology, microbiology, protein purification, protein engineering, protein and DNA sequencing, and recombinant DNA fields, which are within the skill of the art. Such techniques and apparatus are known to those of skill in the art and are described in numerous texts and reference works (See e.g., Sambrook et al., "Molecular Cloning: A Laboratory Manual," Third Edition (Cold Spring Harbor), [2001]); and Ausubel et al., "Current Protocols in Molecular Biology" [1987]).

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not intended to limit the disclosure.

Unless defined otherwise herein, all technical and scientific terms used herein have the same meaning as commonly understood by one of ordinary skill in the art. Various scientific dictionaries that include the terms included herein are well known and available to those in the art. Although any methods and materials similar or equivalent to those described herein find use in the practice or testing of the embodiments disclosed herein, some methods and materials are described.

The terms defined immediately below are more fully described by reference to the Specification as a whole. It is to be understood that this disclosure is not limited to the particular methodology, protocols, and reagents described, as these may vary, depending upon the context they are used by those of skill in the art.

Definitions

As used herein, the singular terms "a," "an," and "the" include the plural reference unless the context clearly indicates otherwise.

Unless otherwise indicated, nucleic acids are written left to right in 5' to 3' orientation and amino acid sequences are written left to right in amino to carboxy orientation, respectively.

The term "assessing" when used herein in the context of analyzing a nucleic acid sample for CNV refers to characterizing the status of a chromosomal or segment aneuploidy by one of three types of calls: "normal" or "unaffected," "affected," and "no-call." Thresholds for calling normal and affected are typically set. A parameter related to aneuploidy or other copy number variation is measured in a sample and the measured value is compared to the thresholds. For duplication type aneuploidies, a call of affected is made if a chromosome or segment dose (or other measured value sequence content) is above a defined threshold set for affected samples. For such aneuploidies, a call of normal is made if the chromosome or segment dose is below a threshold set for normal samples. By contrast for deletion type aneuploidies, a call of affected is made if a chromosome or segment dose is below a defined threshold for affected samples, and a call of normal is made if the chromosome or segment dose is above a threshold set for normal samples.

For example, in the presence of trisomy the "normal" call is determined by the value of a parameter, e.g., a test chromosome dose that is below a user-defined threshold of reliability, and the "affected" call is determined by a parameter, e.g., a test chromosome dose, that is above a user-defined threshold of reliability. A "no-call" result is determined by a parameter, e.g., a test chromosome dose that lies between the thresholds for making a "normal" or an "affected" call. The term "no-call" is used interchangeably with "unclassified".

The term "copy number variation" herein refers to variation in the number of copies of a nucleic acid sequence present in a test sample in comparison with the copy number of the nucleic acid sequence present in a reference sample. In certain embodiments, the nucleic acid sequence is 1 kb or larger. In some cases, the nucleic acid sequence is a whole chromosome or significant portion thereof. A "copy number variant" refers to the sequence of nucleic acid in which copy-number differences are found by comparison of a nucleic acid sequence of interest in test sample with an expected level of the nucleic acid sequence of interest. For example, the level of the nucleic acid sequence of interest in the test sample is compared to that present in a qualified sample. Copy number variants/variations include deletions, including microdeletions, insertions, including microinsertions, duplications, multiplications, and translocations. CNVs encompass chromosomal aneuploidies and partial aneuploidies.

The term "aneuploidy" herein refers to an imbalance of genetic material caused by a loss or gain of a whole chromosome, or part of a chromosome.

The terms "chromosomal aneuploidy" and "complete chromosomal aneuploidy" herein refer to an imbalance of genetic material caused by a loss or gain of a whole chromosome, and includes germline aneuploidy and mosaic aneuploidy.

The terms "partial aneuploidy" and "partial chromosomal aneuploidy" herein refer to an imbalance of genetic material caused by a loss or gain of part of a chromosome, e.g., partial monosomy and partial trisomy, and encompasses imbalances resulting from translocations, deletions and insertions.

The term "plurality" refers to more than one element. For example, the term is used herein in reference to a number of nucleic acid molecules or sequence tags that are sufficient to identify significant differences in copy number variations in test samples and qualified samples using the methods disclosed herein. In some embodiments, at least about $3 \times 10^6$ sequence tags of between about 20 and 40 bp are obtained for each test sample. In some embodiments, each test sample provides data for at least about $5 \times 10^6$, $8 \times 10^6$, $10 \times 10^6$, $15 \times 10^6$, $20 \times 10^6$, $30 \times 10^6$, $40 \times 10^6$, or $50 \times 10^6$ sequence tags, each sequence tag comprising between about 20 and 40 bp.

The terms "polynucleotide," "nucleic acid" and "nucleic acid molecules" are used interchangeably and refer to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The nucleotides include sequences of any form of nucleic acid, including, but not limited to RNA and DNA molecules such as cfDNA molecules. The term "polynucleotide" includes, without limitation, single- and double-stranded polynucleotide.

The term "portion" is used herein in reference to the amount of sequence information of fetal and maternal nucleic acid molecules in a biological sample that in sum amount to less than the sequence information of 1 human genome.

The term "test sample" herein refers to a sample, typically derived from a biological fluid, cell, tissue, organ, or organism, comprising a nucleic acid or a mixture of nucleic acids comprising at least one nucleic acid sequence that is to be screened for copy number variation. In certain embodiments the sample comprises at least one nucleic acid sequence whose copy number is suspected of having undergone variation. Such samples include, but are not limited to sputum/oral fluid, amniotic fluid, blood, a blood fraction, or fine needle biopsy samples (e.g., surgical biopsy, fine needle biopsy, etc.), urine, peritoneal fluid, pleural fluid, and the like. Although the sample is often taken from a human subject (e.g., patient), the assays can be used to copy number variations (CNVs) in samples from any mammal, including, but not limited to dogs, cats, horses, goats, sheep, cattle, pigs, etc. The sample may be used directly as obtained from the biological source or following a pretreatment to modify the character of the sample. For example, such pretreatment may include preparing plasma from blood, diluting viscous fluids and so forth. Methods of pretreatment may also involve, but are not limited to, filtration, precipitation, dilution, distillation, mixing, centrifugation, freezing, lyophilization, concentration, amplification, nucleic acid fragmentation, inactivation of interfering components, the addition of reagents, lysing, etc. If such methods of pretreatment are employed with respect to the sample, such pretreatment methods are typically such that the nucleic acid(s) of interest remain in the test sample, sometimes at a concentration proportional to that in an untreated test sample (e.g., namely, a sample that is not subjected to any such pretreatment method(s)). Such "treated" or "processed" samples are still considered to be biological "test" samples with respect to the methods described herein.

The term "qualified sample" or "unaffected sample" herein refers to a sample comprising a mixture of nucleic acids that are present in a known copy number to which the nucleic acids in a test sample are to be compared, and it is a sample that is normal, i.e., not aneuploid, for the nucleic acid sequence of interest. In some embodiments, qualified samples are used as unaffected training samples of a training set to derive sequence masks or sequence profiles. In certain embodiments, qualified samples are used for identifying one or more normalizing chromosomes or segments for a chromosome under consideration. For example, qualified samples may be used for identifying a normalizing chromosome for chromosome 21. In such case, the qualified sample is a sample that is not a trisomy 21 sample. Another example involves using only females as qualifying samples for chromosome X. Qualified samples may also be employed for other purposes such as determining thresholds for calling affected samples, identifying thresholds for defining mask regions on a reference sequence, determining expected coverage quantities for different regions of a genome, and the like.

The term "training set" herein refers to a set of training samples that can comprise affected and/or unaffected samples and are used to develop a model for analyzing test samples. In some embodiments, the training set includes unaffected samples. In these embodiments, thresholds for determining CNV are established using training sets of samples that are unaffected for the copy number variation of interest. The unaffected samples in a training set may be used as the qualified samples to identify normalizing sequences, e.g., normalizing chromosomes, and the chromosome doses of unaffected samples are used to set the thresholds for each of the sequences, e.g., chromosomes, of interest. In some embodiments, the training set includes affected samples. The affected samples in a training set can be used to verify that affected test samples can be easily differentiated from unaffected samples.

"Training set" is also used herein in reference to a set of individuals of a statistical sample of a population of interest, data of which individuals are used to determine one or more quantitative values of interest generalizable to the population. The statistical sample is a subset of individuals in the population of interest. The individuals may be persons, animals, tissues, cells, other biological samples (i.e., a statistical sample may include multiple biological samples), and other individual entities providing data points for statistical analysis.

Usually, a training set is used in conjunction with a validation set. The term "validation set" is used here in reference to a set of individuals in a statistical sample, data of which individuals are used to validate or evaluate the quantitative values of interest determined using a training set. In some embodiments, for instance, a training set provides data for calculating a mask for a reference sequence; a validation set provides data to validate or evaluate the mask.

"Evaluation of copy number" is used herein in reference to the statistical evaluation of the status of a genetic sequence related to the copy number of the sequence. For example, in some embodiments, the evaluation comprises the determination of the presence or absence of a genetic sequence. In some embodiments the evaluation comprises the determination of the partial or complete aneuploidy of a genetic sequence. In other embodiments the evaluation comprises discrimination between two or more samples based on the copy number of a genetic sequence. In some embodiments, the evaluation comprises statistical analyses, e.g., normalization and comparison, based on the copy number of the genetic sequence.

The term "qualified nucleic acid" is used interchangeably with "qualified sequence," which is a sequence against which the amount of a test sequence or test nucleic acid is compared. A qualified sequence is one present in a biological sample preferably at a known representation, i.e., the amount of a qualified sequence is known. Generally, a qualified sequence is the sequence present in a "qualified sample." A "qualified sequence of interest" is a qualified sequence for which the amount is known in a qualified sample, and is a sequence that is associated with a difference in sequence representation in an individual with a medical condition.

The term "sequence of interest" or "nucleic acid sequence of interest" herein refers to a nucleic acid sequence that is associated with a difference in sequence representation in healthy versus diseased individuals. A sequence of interest can be a sequence on a chromosome that is misrepresented, i.e., over- or under-represented, in a disease or genetic condition. A sequence of interest may be a portion of a chromosome, i.e., chromosome segment, or a whole chromosome. For example, a sequence of interest can be a chromosome that is over-represented in an aneuploidy condition, or a gene encoding a tumor-suppressor that is under-represented in a cancer. Sequences of interest include sequences that are over- or under-represented in the total population, or a subpopulation of cells of a subject. A "qualified sequence of interest" is a sequence of interest in a qualified sample. A "test sequence of interest" is a sequence of interest in a test sample.

The term "normalizing sequence" herein refers to a sequence that is used to normalize the number of sequence tags mapped to a sequence of interest associated with the normalizing sequence. In some embodiments, a normalizing sequence comprises a robust chromosome. A "robust chromosome" is one that is unlikely to be aneuploid. In some cases involving the human chromosome, a robust chromosome is any chromosome other than the X chromosome, Y chromosome, chromosome 13, chromosome 18, and chromosome 21. In some embodiments, the normalizing sequence displays a variability in the number of sequence tags that are mapped to it among samples and sequencing runs that approximates the variability of the sequence of interest for which it is used as a normalizing parameter. The normalizing sequence can differentiate an affected sample from one or more unaffected samples. In some implementations, the normalizing sequence best or effectively differentiates, when compared to other potential normalizing sequences such as other chromosomes, an affected sample from one or more unaffected samples. In some embodiments, the variability of the normalizing sequence is calculated as the variability in the chromosome dose for the sequence of interest across samples and sequencing runs. In some embodiments, normalizing sequences are identified in a set of unaffected samples.

A "normalizing chromosome," "normalizing denominator chromosome," or "normalizing chromosome sequence" is an example of a "normalizing sequence." A "normalizing chromosome sequence" can be composed of a single chromosome or of a group of chromosomes. In some embodiments, a normalizing sequence comprises two or more robust chromosomes. In certain embodiments, the robust chromosomes are all autosomal chromosomes other than chromosomes, X, Y, 13, 18, and 21. A "normalizing segment" is another example of a "normalizing sequence." A "normalizing segment sequence" can be composed of a single segment of a chromosome or it can be composed of two or more segments of the same or of different chromosomes. In certain embodiments, a normalizing sequence is intended to normalize for variability such as process-related, interchromosomal (intra-run), and inter-sequencing (inter-run) variability.

The term "differentiability" herein refers to a characteristic of a normalizing chromosome that enables one to distinguish one or more unaffected, i.e., normal, samples from one or more affected, i.e., aneuploid, samples. A normalizing chromosome displaying the greatest "differentiability" is a chromosome or group of chromosomes that provides the greatest statistical difference between the distribution of chromosome doses for a chromosome of interest in a set of qualified samples and the chromosome dose for the same chromosome of interest in the corresponding chromosome in the one or more affected samples.

The term "variability" herein refers to another characteristic of a normalizing chromosome that enables one to distinguish one or more unaffected, i.e., normal, samples from one or more affected, i.e., aneuploid, samples. The variability of a normalizing chromosome, which is measured in a set of qualified samples, refers to the variability in the number of sequence tags that are mapped to it that approximates the variability in the number of sequence tags that are mapped to a chromosome of interest for which it serves as a normalizing parameter.

The term "sequence tag density" herein refers to the number of sequence reads that are mapped to a reference genome sequence, e.g., the sequence tag density for chromosome 21 is the number of sequence reads generated by the sequencing method that are mapped to chromosome 21 of the reference genome.

The term "sequence tag density ratio" herein refers to the ratio of the number of sequence tags that are mapped to a chromosome of the reference genome, e.g., chromosome 21, to the length of the reference genome chromosome.

The term "sequence dose" herein refers to a parameter that relates the number of sequence tags identified for a sequence of interest and the number of sequence tags identified for the normalizing sequence. In some cases, the sequence dose is the ratio of the sequence tag coverage for a sequence of interest to the sequence tag coverage for a normalizing sequence. In some cases, the sequence dose refers to a parameter that relates the sequence tag density of a sequence of interest to the sequence tag density of a normalizing sequence. A "test sequence dose" is a parameter that relates the sequence tag density of a sequence of interest, e.g., chromosome 21, to that of a normalizing sequence, e.g., chromosome 9, determined in a test sample. Similarly, a "qualified sequence dose" is a parameter that relates the sequence tag density of a sequence of interest to that of a normalizing sequence determined in a qualified sample.

The term "coverage" refers to the abundance of sequence tags mapped to a defined sequence. Coverage can be quantitatively indicated by sequence tag density (or count of sequence tags), sequence tag density ratio, normalized coverage amount, adjusted coverage values, etc.

The term "coverage quantity" is a modification of raw coverage and often represents the relative quantity of sequence tags (sometimes called counts) in a region of a genome such as a bin. A coverage quantity may be obtained by normalizing, adjusting and/or correcting the raw coverage or count for a region of the genome. For example, a normalized coverage quantity for a region may be obtained by dividing the sequence tag count mapped to the region by the total number sequence tags mapped to the entire genome. Normalized coverage quantity allows comparison of coverage of a bin across different samples, which may have different depths of sequencing. It differs from sequence dose in that the latter is typically obtained by dividing by the tag count mapped to a subset of the entire genome. The subset is a normalizing segment or chromosome. Coverage quantities, whether or not normalized, may be corrected for global profile variation from region to region on the genome, G-C fraction variations, outliers in robust chromosomes, etc.

The term "Next Generation Sequencing (NGS)" herein refers to sequencing methods that allow for massively parallel sequencing of clonally amplified molecules and of single nucleic acid molecules. Non-limiting examples of NGS include sequencing-by-synthesis using reversible dye terminators, and sequencing-by-ligation.

The term "parameter" herein refers to a numerical value that characterizes a physical property. Frequently, a parameter numerically characterizes a quantitative data set and/or a numerical relationship between quantitative data sets. For example, a ratio (or function of a ratio) between the number of sequence tags mapped to a chromosome and the length of the chromosome to which the tags are mapped, is a parameter.

The terms "threshold value" and "qualified threshold value" herein refer to any number that is used as a cutoff to characterize a sample such as a test sample containing a nucleic acid from an organism suspected of having a medical condition. The threshold may be compared to a parameter value to determine whether a sample giving rise to such parameter value suggests that the organism has the medical condition. In certain embodiments, a qualified threshold value is calculated using a qualifying data set and serves as a limit of diagnosis of a copy number variation, e.g., an aneuploidy, in an organism. If a threshold is exceeded by results obtained from methods disclosed herein, a subject can be diagnosed with a copy number variation, e.g., trisomy 21. Appropriate threshold values for the methods described herein can be identified by analyzing normalized values (e.g. chromosome doses, NCVs or NSVs) calculated for a training set of samples. Threshold values can be identified using qualified (i.e., unaffected) samples in a training set which comprises both qualified (i.e., unaffected) samples and affected samples. The samples in the training set known to have chromosomal aneuploidies (i.e., the affected samples) can be used to confirm that the chosen thresholds are useful in differentiating affected from unaffected samples in a test set (see the Examples herein). The choice of a threshold is dependent on the level of confidence that the user wishes to have to make the classification. In some embodiments, the training set used to identify appropriate threshold values comprises at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, or more qualified samples. It may advantageous to use larger sets of qualified samples to improve the diagnostic utility of the threshold values.

The term "bin" refers to a segment of a sequence or a segment of a genome. In some embodiments, bins are contiguous with one another and separated by position within the genome or chromosome. Each bin may define a sequence of nucleotides in a reference genome. Sizes of the bin may be 1 kb, 100 kb, 1 Mb, etc., depending on the analysis required by particular applications and sequence tag density. In addition to their positions within a reference sequence, bins may have other characteristics such as sample coverage and sequence structure characteristics such as G-C fraction.

The term "masking threshold" is used herein to refer to a quantity against which a value based on the number of sequence tags in a sequence bin is compared, wherein a bin having a value exceeding the masking threshold is masked. In some embodiments, the masking threshold can be a percentile rank, an absolute count, a mapping quality score, or other suitable values. In some embodiments, a masking threshold may be defined as the percentile rank of a coefficient of variation across multiple unaffected samples. In other embodiments, a masking threshold may be defined as a mapping quality score, e.g., a MapQ score, which relates to the reliability of aligning sequence reads to a reference genome. Note that a masking threshold value is different from a copy number variation (CNV) threshold value, the latter being a cutoff to characterize a sample containing a nucleic acid from an organism suspected of having a medical condition related to CNV. In some embodiment, a CNV threshold value is defined relative to a normalized chromosome value (NCV) or a normalized segment value (NSV) described elsewhere herein.

The term "normalized value" herein refers to a numerical value that relates the number of sequence tags identified for the sequence (e.g. chromosome or chromosome segment) of interest to the number of sequence tags identified for a normalizing sequence (e.g. normalizing chromosome or normalizing chromosome segment). For example, a "normalized value" can be a chromosome dose as described elsewhere herein, or it can be an NCV, or it can be an NSV as described elsewhere herein.

The term "read" refers to a sequence read from a portion of a nucleic acid sample. Typically, though not necessarily, a read represents a short sequence of contiguous base pairs in the sample. The read may be represented symbolically by the base pair sequence (in ATCG) of the sample portion. It may be stored in a memory device and processed as appropriate to determine whether it matches a reference sequence or meets other criteria. A read may be obtained directly from a sequencing apparatus or indirectly from stored sequence information concerning the sample. In some cases, a read is a DNA sequence of sufficient length (e.g., at least about 25 bp) that can be used to identify a larger sequence or region, e.g., that can be aligned and specifically assigned to a chromosome or genomic region or gene.

The term "genomic read" is used in reference to a read of any segments in the entire genome of an individual.

The term "sequence tag" is herein used interchangeably with the term "mapped sequence tag" to refer to a sequence read that has been specifically assigned, i.e., mapped, to a larger sequence, e.g., a reference genome, by alignment. Mapped sequence tags are uniquely mapped to a reference genome, i.e., they are assigned to a single location to the reference genome. Unless otherwise specified, tags that map to the same sequence on a reference sequence are counted once. Tags may be provided as data structures or other assemblages of data. In certain embodiments, a tag contains a read sequence and associated information for that read such as the location of the sequence in the genome, e.g., the position on a chromosome. In certain embodiments, the location is specified for a positive strand orientation. A tag may be defined to provide a limit amount of mismatch in aligning to a reference genome. In some embodiments, tags that can be mapped to more than one location on a reference genome, i.e., tags that do not map uniquely, may not be included in the analysis.

The term "non-redundant sequence tag" refers to sequence tags that do not map to the same site, which is counted for the purpose of determining normalized chromosome values (NCVs) in some embodiments. Sometimes multiple sequence reads are aligned to the same locations on a reference genome, yielding redundant or duplicated sequence tags. In some embodiments, duplicate sequence tags that map to the same position are omitted or counted as one "non-redundant sequence tag" for the purpose of determining NCVs. In some embodiments, non-redundant sequence tags aligned to non-excluded sites are counted to yield "non-excluded-site counts" (NES counts) for determining NCVs.

The term "site" refers to a unique position (i.e. chromosome ID, chromosome position and orientation) on a reference genome. In some embodiments, a site may be a residue, a sequence tag, or a segment's position on a sequence.

"Excluded sites" are sites found in regions of a reference genome that have been excluded for the purpose of counting sequence tags. In some embodiments, excluded sites are found in regions of chromosomes that contain repetitive sequences, e.g., centromeres and telomeres, and regions of chromosomes that are common to more than one chromosome, e.g., regions present on the Y-chromosome that are also present on the X chromosome.

"Non-excluded sites" (NESs) are sites that are not excluded in a reference genome for the purpose of counting sequence tags.

"Non-excluded-site counts" (NES counts) are the numbers of sequence tags that are mapped to NESs on a reference genome. In some embodiments, NES counts are the numbers of non-redundant sequence tags mapped to NESs. In some embodiments, coverage and related parameters such normalized coverage quantities, global profile removed coverage quantities, and chromosome dose are based on NES counts. In one example, a chromosome dose is calculated as the ratio of the number of NES counts for a chromosome of interest to the number of NES counts for a normalizing chromosome.

Normalized chromosome value (NCV) relates coverage of a test sample to coverages of a set of training/qualified samples. In some embodiments, NCV is based on chromosome dose. In some embodiments, NCV relates to the difference between the chromosome dose of a chromosome of interest in a test sample and the mean of the corresponding chromosome dose in a set of qualified samples as, and can be calculated as:

$$NCV_{ij} = \frac{x_{ij} - \hat{\mu}_j}{\hat{\sigma}_j}$$

where $\hat{\mu}_j$ and $\hat{\sigma}_j$ are the estimated mean and standard deviation, respectively, for the j-th chromosome dose in a set of qualified samples, and $x_{ij}$ is the observed j-th chromosome ratio (dose) for test sample i.

In some embodiments, NCV can be calculated "on the fly" by relating the chromosome dose of a chromosome of interest in a test sample to the median of the corresponding chromosome dose in multiplexed samples sequenced on the same flow cells as:

$$NCV_{ij} = \frac{x_{ij} - M_j}{\hat{\sigma}_j}$$

where $M_j$ is the estimated median for the j-th chromosome dose in a set of multiplexed samples sequenced on the same flow cell; $\hat{\sigma}_j$ is the standard deviation for the j-th chromosome dose in one or more sets of multiplexed samples sequenced on one or more flow cells, and $x_i$ is the observed j-th chromosome dose for test sample i. In this embodiment, test sample i is one of the multiplexed samples sequenced on the same flow cell from which $M_j$ is determined.

For example, for chromosome of interest 21 in test sample A, which is sequenced as one of 64 multiplexed samples on one flow cell, the NCV for chromosome 21 in test sample A is calculated as the dose of chromosome 21 in sample A minus the median of the dose for chromosome 21 determined in the 64 multiplexed samples, divided by the standard deviation of the dose for chromosome 21 determined for the 64 multiplexed samples on flow cell 1, or of additional flow cells e.g. 20.

As used herein, the terms "aligned," "alignment," or "aligning" refer to the process of comparing a read or tag to a reference sequence and thereby determining whether the reference sequence contains the read sequence. If the reference sequence contains the read, the read may be mapped to the reference sequence or, in certain embodiments, to a particular location in the reference sequence. In some cases, alignment simply tells whether or not a read is a member of a particular reference sequence (i.e., whether the read is present or absent in the reference sequence). For example, the alignment of a read to the reference sequence for human chromosome 13 will tell whether the read is present in the reference sequence for chromosome 13. A tool that provides this information may be called a set membership tester. In some cases, an alignment additionally indicates a location in the reference sequence where the read or tag maps to. For example, if the reference sequence is the whole human genome sequence, an alignment may indicate that a read is present on chromosome 13, and may further indicate that the read is on a particular strand and/or site of chromosome 13.

Aligned reads or tags are one or more sequences that are identified as a match in terms of the order of their nucleic acid molecules to a known sequence from a reference genome. Alignment can be done manually, although it is typically implemented by a computer algorithm, as it would be impossible to align reads in a reasonable time period for implementing the methods disclosed herein. One example of an algorithm from aligning sequences is the Efficient Local Alignment of Nucleotide Data (ELAND) computer program distributed as part of the Illumina Genomics Analysis pipeline. Alternatively, a Bloom filter or similar set membership tester may be employed to align reads to reference genomes. See U.S. Patent Application No. 61/552,374 filed Oct. 27, 2011 which is incorporated herein by reference in its entirety. The matching of a sequence read in aligning can be a 100% sequence match or less than 100% (non-perfect match).

The term "alignment profile" is used in reference to the distribution of sequence tags aligned to locations which may be identified as base pair bins in a reference sequence of interest.

The term "mapping" used herein refers to specifically assigning a sequence read to a larger sequence, e.g., a reference genome, by alignment.

As used herein, the term "reference genome" or "reference sequence" refers to any particular known genome sequence, whether partial or complete, of any organism or virus which may be used to reference identified sequences from a subject. For example, a reference genome used for human subjects as well as many other organisms is found at the National Center for Biotechnology Information at ncbi.nlm.nih.gov. A "genome" refers to the complete genetic information of an organism or virus, expressed in nucleic acid sequences.

In various embodiments, the reference sequence is significantly larger than the reads that are aligned to it. For example, it may be at least about 100 times larger, or at least about 1000 times larger, or at least about 10,000 times larger, or at least about $10^5$ times larger, or at least about $10^6$ times larger, or at least about $10^7$ times larger.

In one example, the reference sequence is that of a full length human genome. Such sequences may be referred to as genomic reference sequences. In another example, the reference sequence is limited to a specific human chromosome such as chromosome 13. In some embodiments, a reference Y chromosome is the Y chromosome sequence from human genome version hg19. Such sequences may be referred to as chromosome reference sequences. Other examples of reference sequences include genomes of other species, as well as chromosomes, sub-chromosomal regions (such as strands), etc., of any species.

In various embodiments, the reference sequence is a consensus sequence or other combination derived from multiple individuals. However, in certain applications, the reference sequence may be taken from a particular individual.

The term "clinically-relevant sequence" herein refers to a nucleic acid sequence that is known or is suspected to be associated or implicated with a genetic or disease condition. Determining the absence or presence of a clinically-relevant sequence can be useful in determining a diagnosis or confirming a diagnosis of a medical condition, or providing a prognosis for the development of a disease.

The term "derived" when used in the context of a nucleic acid or a mixture of nucleic acids, herein refers to the means whereby the nucleic acid(s) are obtained from the source from which they originate. For example, in one embodiment, a mixture of nucleic acids that is derived from two different genomes means that the nucleic acids, e.g., cfDNA, were naturally released by cells through naturally occurring processes such as necrosis or apoptosis. In another embodiment, a mixture of nucleic acids that is derived from two different genomes means that the nucleic acids were extracted from two different types of cells from a subject.

The term "based on" when used in the context of obtaining a specific quantitative value, herein refers to using another quantity as input to calculate the specific quantitative value as an output.

The term "patient sample" herein refers to a biological sample obtained from a patient, i.e., a recipient of medical attention, care or treatment. The patient sample can be any of the samples described herein. In certain embodiments, the patient sample is obtained by non-invasive procedures, e.g., peripheral blood sample or a stool sample. The methods described herein need not be limited to humans. Thus, various veterinary applications are contemplated in which case the patient sample may be a sample from a non-human mammal (e.g., a feline, a porcine, an equine, a bovine, and the like).

The term "mixed sample" herein refers to a sample containing a mixture of nucleic acids, which are derived from different genomes.

The term "maternal sample" herein refers to a biological sample obtained from a pregnant subject, e.g., a woman.

The term "biological fluid" herein refers to a liquid taken from a biological source and includes, for example, blood, serum, plasma, sputum, lavage fluid, cerebrospinal fluid, urine, semen, sweat, tears, saliva, and the like. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

The terms "maternal nucleic acids" and "fetal nucleic acids" herein refer to the nucleic acids of a pregnant female subject and the nucleic acids of the fetus being carried by the pregnant female, respectively.

As used herein, the term "corresponding to" sometimes refers to a nucleic acid sequence, e.g., a gene or a chromosome, that is present in the genome of different subjects, and which does not necessarily have the same sequence in all genomes, but serves to provide the identity rather than the genetic information of a sequence of interest, e.g., a gene or chromosome.

As used herein, the term "substantially cell free" used in connection with a desired sample encompasses preparations of the desired sample from which cell components normally associated with the sample are removed. For example, a plasma sample is rendered substantially cell free by removing blood cells, e.g., red cells, which are normally associated with it. In some embodiments, substantially cell free samples are processed to remove cells that would otherwise contribute to the desired genetic material that is to be tested for a CNV.

As used herein, the term "fetal fraction" refers to the fraction of fetal nucleic acids present in a sample comprising fetal and maternal nucleic acid. Fetal fraction is often used to characterize the cfDNA in a mother's blood.

As used herein the term "chromosome" refers to the heredity-bearing gene carrier of a living cell, which is derived from chromatin strands comprising DNA and protein components (especially histones). The conventional internationally recognized individual human genome chromosome numbering system is employed herein.

As used herein, the term "polynucleotide length" refers to the absolute number of nucleic acid molecules (nucleotides) in a sequence or in a region of a reference genome. The term "chromosome length" refers to the known length of the chromosome given in base pairs, e.g., provided in the NCBI36/hg18 assembly of the human chromosome found at |genome|.|ucsc|.|edu/cgi-bin/hgTracks?hgsid=167155613&chromInfoPage= on the World Wide Web.

The term "subject" herein refers to a human subject as well as a non-human subject such as a mammal, an invertebrate, a vertebrate, a fungus, a yeast, a bacterium, and a virus. Although the examples herein concern humans and the language is primarily directed to human concerns, the concepts disclosed herein are applicable to genomes from any plant or animal, and are useful in the fields of veterinary medicine, animal sciences, research laboratories and such.

The term "condition" herein refers to "medical condition" as a broad term that includes all diseases and disorders, but can include [injuries] and normal health situations, such as pregnancy, that might affect a person's health, benefit from medical assistance, or have implications for medical treatments.

The term "complete" when used in reference to a chromosomal aneuploidy herein refers to a gain or loss of an entire chromosome.

The term "partial" when used in reference to a chromosomal aneuploidy herein refers to a gain or loss of a portion, i.e., segment, of a chromosome.

The term "mosaic" herein refers to denote the presence of two populations of cells with different karyotypes in one individual who has developed from a single fertilized egg. Mosaicism may result from a mutation during development which is propagated to only a subset of the adult cells.

The term "non-mosaic" herein refers to an organism, e.g., a human fetus, composed of cells of one karyotype.

The term "using a chromosome" when used in reference to determining a chromosome dose, herein refers to using the sequence information obtained for a chromosome, i.e., the number of sequence tags obtained for a chromosome.

The term "sensitivity" as used herein is equal to the number of true positives divided by the sum of true positives and false negatives.

The term "specificity" as used herein is equal to the number of true negatives divided by the sum of true negatives and false positives.

The term "enrich" herein refers to the process of amplifying polymorphic target nucleic acids contained in a portion of a maternal sample, and combining the amplified product with the remainder of the maternal sample from which the portion was removed. For example, the remainder of the maternal sample can be the original maternal sample.

The term "original maternal sample" herein refers to a non-enriched biological sample obtained from a pregnant subject, e.g., a woman, who serves as the source from which a portion is removed to amplify polymorphic target nucleic acids. The "original sample" can be any sample obtained from a pregnant subject, and the processed fractions thereof, e.g., a purified cfDNA sample extracted from a maternal plasma sample.

The term "primer," as used herein refers to an isolated oligonucleotide that is capable of acting as a point of initiation of synthesis when placed under conditions inductive to synthesis of an extension product (e.g., the conditions include nucleotides, an inducing agent such as DNA polymerase, and a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer, use of the method, and the parameters used for primer design.

The phrase "cause to be administered" refers to the actions taken by a medical professional (e.g., a physician), or a person controlling or directing medical care of a subject, that control and/or permit the administration of the agent(s)/compound(s) at issue to the subject. Causing to be administered can involve diagnosis and/or determination of an appropriate therapeutic or prophylactic regimen, and/or prescribing particular agent(s)/compounds for a subject. Such prescribing can include, for example, drafting a prescription form, annotating a medical record, and the like. Similarly, "cause to be performed," e.g., for a diagnostic procedure refers to the actions taken by a medical professional (e.g., a physician), or a person controlling or directing medical care of a subject, that control and/or permit the performance of one or more diagnostic protocols to or on the subject.

Introduction

Methods, apparatus, and systems are disclosed herein for determining copy number and copy number variations (CNV) of different sequences of interest in a test sample that comprises a mixture of nucleic acids derived from two or more different genomes, and which are known or are suspected to differ in the amount of one or more sequence of interest. Copy number variations determined by the methods and apparatus disclosed herein include gains or losses of entire chromosomes, alterations involving very large chromosomal segments that are microscopically visible, and an abundance of sub-microscopic copy number variation of DNA segments ranging from single nucleotide, to kilobases (kb), to megabases (Mb) in size.

In some embodiments, methods are provided for determining copy number variation (CNV) of fetuses using maternal samples containing maternal and fetal cell free DNA. Some embodiments disclosed herein provide methods to improve the sensitivity and/or specificity of sequence data analysis by removing within-sample GC-content bias. In some embodiments, removal of within-sample GC-content bias is based on sequence data corrected for systematic variation common across unaffected training samples.

Some embodiments disclosed provide methods to determine sequence coverage quantities with low noise and high signal, providing data to determine various genetic conditions related to copy number and CNV with improved sensitivity, selectivity, and/or efficiency relative to sequence coverage quantities obtained by conventional methods. The depicted process has been found particularly effective at improving the signal in samples having relatively low fractions of DNA from a genome under consideration (e.g., a genome of a fetus). An example of such sample is a maternal blood sample from an individual pregnant with fraternal twins, triplets, etc., where the process assesses copy number variation in the genome of one of the fetuses.

The methods are applicable to determining CNV of any fetal aneuploidy, and CNVs known or suspected to be associated with a variety of medical conditions. In some embodiments involving human subjects, CNV that can be determined according to the present method include trisomies and monosomies of any one or more of chromosomes 1-22, X and Y, other chromosomal polysomies, and deletions and/or duplications of segments of any one or more of the chromosomes, which can be detected by sequencing only once the nucleic acids of a test sample. Any aneuploidy can be determined from sequencing information that is obtained by sequencing only once the nucleic acids of a test sample.

CNV in the human genome significantly influence human diversity and predisposition to disease (Redon et al., Nature 23:444-454 [2006], Shaikh et al. Genome Res 19:1682-1690 [2009]). CNVs have been known to contribute to genetic disease through different mechanisms, resulting in either imbalance of gene dosage or gene disruption in most cases. In addition to their direct correlation with genetic disorders, CNVs are known to mediate phenotypic changes that can be deleterious. Recently, several studies have reported an increased burden of rare or de novo CNVs in complex disorders such as Autism, ADHD, and schizophrenia as compared to normal controls, highlighting the potential pathogenicity of rare or unique CNVs (Sebat et al., 316: 445-449 [2007]; Walsh et al., Science 320:539-543 [2008]). CNV arise from genomic rearrangements, primarily owing to deletion, duplication, insertion, and unbalanced translocation events.

The methods and apparatus described herein may employ next generation sequencing technology (NGS), which is massively parallel sequencing. In certain embodiments, clonally amplified DNA templates or single DNA molecules are sequenced in a massively parallel fashion within a flow cell (e.g. as described in Volkerding et al. Clin Chem 55:641-658 [2009]; Metzker M Nature Rev 11:31-46 [2010]). In addition to high-throughput sequence information, NGS provides quantitative information, in that each sequence read is a countable "sequence tag" representing an individual clonal DNA template or a single DNA molecule. The sequencing technologies of NGS include pyrosequencing, sequencing-by-synthesis with reversible dye terminators, sequencing by oligonucleotide probe ligation and ion semiconductor sequencing. DNA from individual samples can be sequenced individually (i.e., singleplex sequencing) or DNA from multiple samples can be pooled and sequenced as indexed genomic molecules (i.e., multiplex sequencing) on a single sequencing run, to generate up to several hundred million reads of DNA sequences. Examples of sequencing technologies that can be used to obtain the sequence information according to the present method are described herein after.

Various CNV analyses using DNA samples involve aligning or mapping sequence reads from a sequencer to a reference sequence. A reference sequence may be the sequence of whole genome, the sequence of a chromosome, the sequence of a sub chromosomal region, etc. Due to the characteristics of the reference sequence, diagnosis of CNV of the Y chromosome involves heightened technical challenges compared to autosomes, because coverage of the Y chromosome is lower than that of autosomes, and repeated sequences on the Y chromosome complicate mapping of reads to their correct location. There are about 10 Mb of unique Y sequence accessible by current NGS technologies, but gender detection remains to be a challenging task in fetal diagnostic world where the amount of fetal cfDNA in a maternal sample is at least an order of magnitude lower than that of maternal DNA, emphasizing the problem of nonspecific mapping.

Additionally, some current sequencing protocols utilize ultra-short reads such as 25mer reads and tags. Ultra-short sequencing utilized in processes of sequencing protocols generate short read lengths that presented technical challenges for sequence alignment since nearly half of the human genome is covered by repeats, many of which have been known about for decades. From a computational perspective, repeats create ambiguities in alignment, which, in turn, can produce biases and errors even at the whole chromosome counting level.

Evaluating CNV

Methods for Determination of CNV

Using the sequence coverage values provided by the methods disclosed herein, one can determine various genetic conditions related to copy number and CNV of sequences, chromosomes, or chromosome segments with improved sensitivity, selectivity, and/or efficiency relative to using sequence coverage values obtained by conventional methods. For example, in some embodiments, the masked reference sequences are used for determining the presence or absence of any two or more different complete fetal chromosomal aneuploidies in a maternal test sample comprising fetal and maternal nucleic acid molecules. Exemplary methods provided below align reads to reference sequences (including reference genomes). The alignment can be performed on an unmasked or masked reference sequence, thereby yielding sequence tags mapped to the reference sequence. In some embodiments, only sequence tags falling on unmasked segments of the reference sequence are taken into account to determine copy number variation.

In some embodiments, the method for determining the presence or absence of any complete fetal chromosomal aneuploidies in a maternal test sample comprises (a) obtaining sequence information for fetal and maternal nucleic acids in the maternal test sample; (b) using the sequence information and the method described above to identify a number of sequence tags or sequence coverage quantity derived therefrom for each of the chromosomes of interest selected from chromosomes 1-22, X and Y and to identify a number of sequence tags for one or more normalizing chromosome sequences; (c) using the number of sequence tags identified for each of the chromosomes of interest and the number of sequence tags identified for each of the normalizing chromosomes to calculate a single chromosome dose for each of the chromosomes of interests; and (d) comparing each chromosome dose to a threshold value, and thereby determining the presence or absence of any complete fetal chromosomal aneuploidies in the maternal test sample.

In some embodiments, step (a) described above can comprise sequencing at least a portion of the nucleic acid molecules of a test sample to obtain said sequence information for the fetal and maternal nucleic acid molecules of the test sample. In some embodiments, step (c) comprises calculating a single chromosome dose for each of the chromosomes of interest as the ratio of the number of sequence tags identified for each of the chromosomes of interest and the number of sequence tags identified for the normalizing chromosome sequence(s). In some other embodiments, chromosome dose is based on processed sequence coverage quantities derived from the number of sequence tags. In some embodiments, only unique, non-redundant sequence tags are used to calculate the processed sequence coverage quantities. In some embodiments, the processed sequence coverage quantity is a sequence tag density ratio, which is the number of sequence tag standardized by sequence length. In some embodiments, the processed sequence coverage quantity is a normalized sequence tag, which is the number of sequence tags of a sequence of interest divided by all or a substantial portion of the genome. In some embodiments, the processed sequence coverage quantity is adjusted according to a global profile of the sequence of interest. In some embodiments, the processed sequence coverage quantity is adjusted according to the within-sample correlation between the GC content and the sequence coverage for the sample being tested. In some embodiments, the processed sequence coverage quantity results from combinations of these processes, which are further described elsewhere herein.

In some embodiments, a chromosome dose is calculated as the ratio of the processed sequence coverage quantities for each of the chromosomes of interest and processed sequence coverage quantities for the normalizing chromosome sequence(s).

In any one of the embodiments above, the complete chromosomal aneuploidies are selected from complete chromosomal trisomies, complete chromosomal monosomies and complete chromosomal polysomies. The complete chromosomal aneuploidies are selected from complete aneuploidies of any one of chromosome 1-22, X, and Y. For example, the said different complete fetal chromosomal aneuploidies are selected from trisomy 2, trisomy 8, trisomy 9, trisomy 20, trisomy 21, trisomy 13, trisomy 16, trisomy 18, trisomy 22, 47,XXX, 47,XYY, and monosomy X.

In any one of the embodiments above, steps (a)-(d) are repeated for test samples from different maternal subjects, and the method comprises determining the presence or absence of any two or more different complete fetal chromosomal aneuploidies in each of the test samples.

In any one of the embodiments above, the method can further comprise calculating a normalized chromosome value (NCV), wherein the NCV relates the chromosome dose to the mean of the corresponding chromosome dose in a set of qualified samples as:

$$NCV_{ij} = \frac{x_{ij} - \hat{\mu}_j}{\hat{\sigma}_j}$$

where $\hat{\mu}_j$ and $\hat{\sigma}_j$ are the estimated mean and standard deviation, respectively, for the j-th chromosome dose in a set of qualified samples, and $x_{ij}$ is the observed j-th chromosome dose for test sample i.

In some embodiments, NCV can be calculated "on the fly" by relating the chromosome dose of a chromosome of interest in a test sample to the median of the corresponding chromosome dose in multiplexed samples sequenced on the same flow cells as:

$$NCV_{ij} = \frac{x_{ij} - M_j}{\hat{\sigma}_j}$$

where $M_j$ is the estimated median for the j-th chromosome dose in a set of multiplexed samples sequenced on the same flow cell; $\hat{\sigma}_j$ is the standard deviation for the j-th chromosome dose in one or more sets of multiplexed samples sequenced on one or more flow cells, and $x_i$ is the observed j-th chromosome dose for test sample i. In this embodiment, test sample i is one of the multiplexed samples sequenced on the same flow cell from which $M_j$ is determined.

In some embodiments, a method is provided for determining the presence or absence of different partial fetal chromosomal aneuploidies in a maternal test sample comprising fetal and maternal nucleic acids. The method involves procedures analogous to the method for detecting complete aneuploidy as outlined above. However, instead of analyzing a complete chromosome, a segment of a chromosome is analyzed. See US Patent Application Publication No. 2013/0029852, which is incorporated by reference.

FIG. 1 shows a method for determining the presence of copy number variation in accordance with some embodiments. In operations 130 and 135, qualified sequence tag coverages and test sequence tag coverages are determined. The present disclosure provides processes to determine coverage quantities that provide improved sensitivity and selectivity relative to conventional methods. Operation 130 and 135 are marked by asterisks and emphasized by boxes of heavy lines to indicate these operations contribute to improvement over prior art. In some embodiments, the sequence tag coverage quantities are normalized, adjusted, trimmed, and otherwise processed to improve the sensitivity and selectivity of the analysis. These processes are further described elsewhere herein.

From an over-view perspective, the method makes use of normalizing sequences of qualified training samples in determination of CNV of test samples. In some embodiments, the qualified training samples are unaffected and have normal copy number. Normalizing sequences provide a mechanism to normalize measurements for intra-run and inter-run variabilities. Normalizing sequences are identified using sequence information from a set of qualified samples obtained from subjects known to comprise cells having a normal copy number for any one sequence of interest, e.g., a chromosome or segment thereof. Determination of normalizing sequences is outlined in steps 110, 120, 130, 145 and 146 of the embodiment of the method depicted in FIG. 1. In some embodiments, the normalizing sequences are used to calculate sequence dose for test sequences. See step 150. In some embodiments, normalizing sequences are also used to calculate a threshold against which the sequence dose of the test sequences is compared. See step 150. The sequence information obtained from the normalizing sequence and the test sequence is used for determining statistically meaningful identification of chromosomal aneuploidies in test samples (step 160).

Turning to the details of the method for determining the presence of copy number variation according to some embodiments, FIG. 1 provides a flow diagram 100 of an embodiment for determining a CNV of a sequence of interest, e.g., a chromosome or segment thereof, in a biological sample. In some embodiments, a biological sample is obtained from a subject and comprises a mixture of nucleic acids contributed by different genomes. The different genomes can be contributed to the sample by two individuals, e.g., the different genomes are contributed by the fetus and the mother carrying the fetus. Also, the different genomes can be contributed to the sample by three or more individuals, e.g., the different genomes are contributed by two or more fetuses and the mother carrying the fetuses. Alternatively, the genomes are contributed to the sample by aneuploid cancerous cells and normal euploid cells from the same subject, e.g., a plasma sample from a cancer patient.

Apart from analyzing a patient's test sample, one or more normalizing chromosomes or one or more normalizing chromosome segments are selected for each possible chromosome of interest. The normalizing chromosomes or segments are identified asynchronously from the normal testing of patient samples, which may take place in a clinical setting. In other words, the normalizing chromosomes or segments are identified prior to testing patient samples. The associations between normalizing chromosomes or segments and chromosomes or segments of interest are stored for use during testing. As explained below, such association is typically maintained over periods of time that span testing of many samples. The following discussion concerns embodiments for selecting normalizing chromosomes or chromosome segments for individual chromosomes or segments of interest.

A set of qualified samples is obtained to identify qualified normalizing sequences and to provide variance values for use in determining statistically meaningful identification of CNV in test samples. In step 110, a plurality of biological qualified samples are obtained from a plurality of subjects known to comprise cells having a normal copy number for any one sequence of interest. In one embodiment, the qualified samples are obtained from mothers pregnant with a fetus that has been confirmed using cytogenetic means to have a normal copy number of chromosomes. The biological qualified samples may be a biological fluid, e.g., plasma, or any suitable sample as described below. In some embodiments, a qualified sample contains a mixture of nucleic acid molecules, e.g., cfDNA molecules. In some embodiments, the qualified sample is a maternal plasma sample that contains a mixture of fetal and maternal cfDNA molecules. Sequence information for normalizing chromosomes and/or segments thereof is obtained by sequencing at least a portion of the nucleic acids, e.g., fetal and maternal nucleic acids, using any known sequencing method. Preferably, any one of the Next Generation Sequencing (NGS) methods described elsewhere herein is used to sequence the fetal and maternal nucleic acids as single or clonally amplified molecules. In various embodiments, the qualified samples are processed as disclosed below prior to and during sequencing. They may be processed using apparatus, systems, and kits as disclosed herein.

In step 120, at least a portion of each of all the qualified nucleic acids contained in the qualified samples are sequenced to generate millions of sequence reads, e.g., 36 bp reads, which are aligned to a reference genome, e.g., hg18. In some embodiments, the sequence reads comprise about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the mapped sequence reads comprise 36 bp. In another embodiment, the mapped sequence reads comprise 25 bp.

Sequence reads are aligned to a reference genome, and the reads that are uniquely mapped to the reference genome are known as sequence tags. Sequence tags falling on masked segments of a masked reference sequence are not counted for analysis of CNV.

In one embodiment, at least about $3 \times 10^6$ qualified sequence tags, at least about $5 \times 10^6$ qualified sequence tags, at least about $8 \times 10^6$ qualified sequence tags, at least about $10 \times 10^6$ qualified sequence tags, at least about $15 \times 10^6$ qualified sequence tags, at least about $20 \times 10^6$ qualified sequence tags, at least about $30 \times 10^6$ qualified sequence tags, at least about $40 \times 10^6$ qualified sequence tags, or at least about $50 \times 10^6$ qualified sequence tags comprising between 20 and 40 bp reads are obtained from reads that map uniquely to a reference genome.

In step 130, all the tags obtained from sequencing the nucleic acids in the qualified samples are counted to obtain a qualified sequence tag coverage. Similarly, in operation 135, all tags obtained from a test sample are counted to obtain a test sequence tag coverage. The present disclosure provides processes to determine coverage quantities that provides improved sensitivity and selectivity relative to conventional methods. Operation 130 and 135 are marked by asterisks and emphasized by boxes of heavy lines to indicate these operations contribute to improvement over prior art. In some embodiments, the sequence tag coverage quantities are normalized, adjusted, trimmed, and otherwise processed to improve the sensitivity and selectivity of the analysis. These processes are further described elsewhere herein.

As all qualified sequence tags are mapped and counted in each of the qualified samples, the sequence tag coverage for a sequence of interest, e.g., a clinically-relevant sequence, in the qualified samples is determined, as are the sequence tag coverages for additional sequences from which normalizing sequences are identified subsequently.

In some embodiments, the sequence of interest is a chromosome that is associated with a complete chromosomal aneuploidy, e.g., chromosome 21, and the qualified normalizing sequence is a complete chromosome that is not associated with a chromosomal aneuploidy and whose variation in sequence tag coverage approximates that of the sequence (i.e., chromosome) of interest, e.g., chromosome 21. The selected normalizing chromosome(s) may be the one or group that best approximates the variation in sequence tag coverage of the sequence of interest. Any one or more of chromosomes 1-22, X, and Y can be a sequence of interest, and one or more chromosomes can be identified as the normalizing sequence for each of the any one chromosomes 1-22, X and Y in the qualified samples. The normalizing chromosome can be an individual chromosome or it can be a group of chromosomes as described elsewhere herein.

In another embodiment, the sequence of interest is a segment of a chromosome associated with a partial aneuploidy, e.g., a chromosomal deletion or insertion, or unbalanced chromosomal translocation, and the normalizing sequence is a chromosomal segment (or group of segments) that is not associated with the partial aneuploidy and whose variation in sequence tag coverage approximates that of the chromosome segment associated with the partial aneuploidy. The selected normalizing chromosome segment(s) may be the one or more that best approximates the variation in sequence tag coverage of the sequence of interest. Any one or more segments of any one or more chromosomes 1-22, X, and Y can be a sequence of interest.

In other embodiments, the sequence of interest is a segment of a chromosome associated with a partial aneuploidy and the normalizing sequence is a whole chromosome or chromosomes. In still other embodiments, the sequence of interest is a whole chromosome associated with an aneuploidy and the normalizing sequence is a chromosomal segment or segments that are not associated with the aneuploidy.

Whether a single sequence or a group of sequences are identified in the qualified samples as the normalizing sequence(s) for any one or more sequences of interest, the qualified normalizing sequence may be chosen to have a variation in sequence tag coverage that best or effectively approximates that of the sequence of interest as determined in the qualified samples. For example, a qualified normalizing sequence is a sequence that produces the smallest variability across the qualified samples when used to normalize the sequence of interest, i.e., the variability of the normalizing sequence is closest to that of the sequence of interest determined in qualified samples. Stated another way, the qualified normalizing sequence is the sequence selected to produce the least variation in sequence dose (for the sequence of interest) across the qualified samples. Thus, the process selects a sequence that when used as a normalizing chromosome is expected to produce the smallest variability in run-to-run chromosome dose for the sequence of interest.

The normalizing sequence identified in the qualified samples for any one or more sequences of interest remains the normalizing sequence of choice for determining the presence or absence of aneuploidy in test samples over days, weeks, months, and possibly years, provided that procedures needed to generate sequencing libraries, and sequencing the samples are essentially unaltered over time. As described above, normalizing sequences for determining the presence of aneuploidies are chosen for (possibly among other reasons as well) the variability in the number of sequence tags that are mapped to it among samples, e.g., different samples, and sequencing runs, e.g., sequencing runs that occur on the same day and/or different days, that best approximates the variability of the sequence of interest for which it is used as a normalizing parameter. Substantial alterations in these procedures will affect the number of tags that are mapped to all sequences, which in turn will determine which one or group of sequences will have a variability across samples in the same and/or in different sequencing runs, on the same day or on different days that most closely approximates that of the sequence(s) of interest, which would require that the set of normalizing sequences be re-determined. Substantial alterations in procedures include changes in the laboratory protocol used for preparing the sequencing library, which includes changes related to preparing samples for multiplex sequencing instead of singleplex sequencing, and changes in sequencing platforms, which include changes in the chemistry used for sequencing.

In some embodiments, the normalizing sequence chosen to normalize a particular sequence of interest is a sequence that best distinguishes one or more qualified, samples from one or more affected samples, which implies that the normalizing sequence is a sequence that has the greatest differentiability, i.e., the differentiability of the normalizing sequence is such that it provides optimal differentiation to a sequence of interest in an affected test sample to easily distinguish the affected test sample from other unaffected samples. In other embodiments, the normalizing sequence is a sequence that has a combination of the smallest variability and the greatest differentiability.

The level of differentiability can be determined as a statistical difference between the sequence doses, e.g., chromosome doses or segment doses, in a population of qualified samples and the chromosome dose(s) in one or more test samples as described below and shown in the Examples. For example, differentiability can be represented numerically as a t-test value, which represents the statistical difference between the chromosome doses in a population of qualified samples and the chromosome dose(s) in one or more test samples. Similarly, differentiability can be based on segment doses instead of chromosome doses. Alternatively, differentiability can be represented numerically as a Normalized Chromosome Value (NCV), which is a z-score for chromosome doses as long as the distribution for the NCV is normal. Similarly, in the case where chromosome segments are the sequences of interest, differentiability of segment doses can be represented numerically as a Normalized Segment Value (NSV), which is a z-score for chromosome segment doses as long as the distribution for the NSV is normal. In determining the z-score, the mean and standard deviation of chromosome or segment doses in a set of qualified samples can be used. Alternatively, the mean and standard deviation of chromosome or segment doses in a training set comprising qualified samples and affected samples can be used. In other embodiments, the normalizing sequence is a sequence that has the smallest variability and the greatest differentiability or an optimal combination of small variability and large differentiability.

The method identifies sequences that inherently have similar characteristics and that are prone to similar variations among samples and sequencing runs, and which are useful for determining sequence doses in test samples.

Determination of Sequence Doses

In some embodiments, chromosome or segment doses for one or more chromosomes or segments of interest are determined in all qualified samples as described in step 146 shown in FIG. 1, and a normalizing chromosome or segment sequence is identified in step 145. Some normalizing sequences are provided before sequence doses are calculated. Then one or more normalizing sequences are identified according to various criteria as further described below, see step 145. In some embodiments, e.g., the identified normalizing sequence results in the smallest variability in sequence dose for the sequence of interest across all qualified samples.

In step 146, based on the calculated qualified tag densities, a qualified sequence dose, i.e., a chromosome dose or a segment dose, for a sequence of interest is determined as the ratio of the sequence tag coverage for the sequence of interest and the qualified sequence tag coverage for additional sequences from which normalizing sequences are identified subsequently in step 145. The identified normalizing sequences are used subsequently to determine sequence doses in test samples.

In one embodiment, the sequence dose in the qualified samples is a chromosome dose that is calculated as the ratio of the number of sequence tags for a chromosome of interest and the number of sequence tags for a normalizing chromosome sequence in a qualified sample. The normalizing chromosome sequence can be a single chromosome, a group of chromosomes, a segment of one chromosome, or a group of segments from different chromosomes. Accordingly, a chromosome dose for a chromosome of interest is determined in a qualified sample as the ratio of the number of tags for a chromosome of interest and the number of tags for (i) a normalizing chromosome sequence composed of a single chromosome, (ii) a normalizing chromosome sequence composed of two or more chromosomes, (iii) a normalizing segment sequence composed of a single segment of a chromosome, (iv) a normalizing segment sequence composed of two or more segments form one chromosome, or (v) a normalizing segment sequence composed of two or more segments of two or more chromosomes. Examples for determining a chromosome dose for chromosome of interest 21 according to (i)-(v) are as follows: chromosome doses for chromosome of interest, e.g., chromosome 21, are determined as a ratio of the sequence tag coverage of chromosome 21 and one of the following sequence tag coverages: (i) each of all the remaining chromosomes, i.e., chromosomes 1-20, chromosome 22, chromosome X, and chromosome Y; (ii) all possible combinations of two or more remaining chromosomes; (iii) a segment of another chromosome, e.g., chromosome 9; (iv) two segments of one other chromosome, e.g., two segments of chromosome 9; (v) two segments of two different chromosomes, e.g., a segment of chromosome 9 and a segment of chromosome 14.

In another embodiment, the sequence dose in the qualified samples is a segment dose as opposed to a chromosome dose, which segment dose is calculated as the ratio of the number of sequence tags for a segment of interest, that is not a whole chromosome, and the number of sequence tags for a normalizing segment sequence in a qualified sample. The normalizing segment sequence can be any of the normalizing chromosome or segment sequences discussed above.

Identification of Normalizing Sequences

In step 145, a normalizing sequence is identified for a sequence of interest. In some embodiments, e.g., the normalizing sequence is the sequence based on the calculated sequence doses, e.g., that result in the smallest variability in sequence dose for the sequence of interest across all qualified training samples. The method identifies sequences that inherently have similar characteristics and are prone to similar variations among samples and sequencing runs, and which are useful for determining sequence doses in test samples.

Normalizing sequences for one or more sequences of interest can be identified in a set of qualified samples, and the sequences that are identified in the qualified samples are used subsequently to calculate sequence doses for one or more sequences of interest in each of the test samples (step 150) to determine the presence or absence of aneuploidy in each of the test samples. The normalizing sequence identified for chromosomes or segments of interest may differ when different sequencing platforms are used and/or when differences exist in the purification of the nucleic acid that is to be sequenced and/or preparation of the sequencing library. The use of normalizing sequences according to the methods described herein provides specific and sensitive measure of a variation in copy number of a chromosome or segment thereof irrespective of sample preparation and/or sequencing platform that is used.

In some embodiments, more than one normalizing sequence is identified, i.e., different normalizing sequences can be determined for one sequence of interest, and multiple sequence doses can be determined for one sequence of interest. For example, the variation, e.g., coefficient of variation (CV=standard deviation/mean), in chromosome dose for chromosome of interest 21 is least when the sequence tag coverage of chromosome 14 is used. However, two, three, four, five, six, seven, eight or more normalizing sequences can be identified for use in determining a sequence dose for a sequence of interest in a test sample. As an example, a second dose for chromosome 21 in any one test sample can be determined using chromosome 7, chromosome 9, chromosome 11 or chromosome 12 as the normalizing chromosome sequence as these chromosomes all have CV close to that for chromosome 14.

In some embodiments, when a single chromosome is chosen as the normalizing chromosome sequence for a chromosome of interest, the normalizing chromosome sequence will be a chromosome that results in chromosome doses for the chromosome of interest that has the smallest variability across all samples tested, e.g., qualified samples.

In some instances, the best normalizing chromosome may not have the least variation, but may have a distribution of qualified doses that best distinguishes a test sample or samples from the qualified samples, i.e., the best normalizing chromosome may not have the lowest variation, but may have the greatest differentiability.

In some embodiments, normalizing sequences include one or more robust autosomes sequences or segments thereof. In some embodiments, the robust autosomes include all autosomes except for the chromosome(s) of interest. In some embodiments, the robust autosomes include all autosomes except for chr X, Y, 13, 18, and 21. In some embodiments, the robust autosomes include all autosomes except those determined from a sample to be deviating from a normal diploid state, which can be useful in determining cancer genomes that have abnormal copy number relative to a normal diploid genome.

Determination of Aneuploidies in Test Samples

Based on the identification of the normalizing sequence(s) in qualified samples, a sequence dose is determined for a sequence of interest in a test sample comprising a mixture of nucleic acids derived from genomes that differ in one or more sequences of interest.

In step 115, a test sample is obtained from a subject suspected or known to carry a clinically-relevant CNV of a sequence of interest. The test sample may be a biological fluid, e.g., plasma, or any suitable sample as described below. As explained, the sample may be obtained using a non-invasive procedure such as a simple blood draw. In some embodiments, a test sample contains a mixture of nucleic acid molecules, e.g., cfDNA molecules. In some embodiments, the test sample is a maternal plasma sample that contains a mixture of fetal and maternal cfDNA molecules.

In step 125, at least a portion of the test nucleic acids in the test sample is sequenced as described for the qualified samples to generate millions of sequence reads, e.g., 36 bp reads. As in step 120, the reads generated from sequencing the nucleic acids in the test sample are uniquely mapped or aligned to a reference genome to produce tags. As described in step 120, at least about $3\times10^6$ qualified sequence tags, at least about $5\times10^6$ qualified sequence tags, at least about $8\times10^6$ qualified sequence tags, at least about $10\times10^6$ qualified sequence tags, at least about $15\times10^6$ qualified sequence tags, at least about $20\times10^6$ qualified sequence tags, at least about $30\times10^6$ qualified sequence tags, at least about $40\times10^6$ qualified sequence tags, or at least about $50\times10^6$ qualified sequence tags comprising between 20 and 40 bp reads are obtained from reads that map uniquely to a reference genome. In certain embodiments, the reads produced by sequencing apparatus are provided in an electronic format. Alignment is accomplished using computational apparatus as discussed below. Individual reads are compared against the reference genome, which is often vast (millions of base pairs) to identify sites where the reads uniquely correspond with the reference genome. In some embodiments, the alignment procedure permits limited mismatch between reads and the reference genome. In some cases, 1, 2, or 3 base pairs in a read are permitted to mismatch corresponding base pairs in a reference genome, and yet a mapping is still made.

In step 135, all or most of the tags obtained from sequencing the nucleic acids in the test samples are counted to determine a test sequence tag coverage using a computational apparatus as described below. In some embodiments, each read is aligned to a particular region of the reference genome (a chromosome or segment in most cases), and the read is converted to a tag by appending site information to the read. As this process unfolds, the computational apparatus may keep a running count of the number of tags/reads mapping to each region of the reference genome (chromosome or segment in most cases). The counts are stored for each chromosome or segment of interest and each corresponding normalizing chromosome or segment.

In certain embodiments, the reference genome has one or more excluded regions that are part of a true biological genome but are not included in the reference genome. Reads potentially aligning to these excluded regions are not counted. Examples of excluded regions include regions of long repeated sequences, regions of similarity between X and Y chromosomes, etc. Using a masked reference sequence obtained by masking techniques described above, only tags on unmasked segments of the reference sequence are taken into account for analysis of CNV.

In some embodiments, the method determines whether to count a tag more than once when multiple reads align to the same site on a reference genome or sequence. There may be occasions when two tags have the same sequence and therefore align to an identical site on a reference sequence. The method employed to count tags may under certain circumstances exclude from the count identical tags deriving from the same sequenced sample. If a disproportionate number of tags are identical in a given sample, it suggests that there is a strong bias or other defect in the procedure. Therefore, in accordance with certain embodiments, the counting method does not count tags from a given sample that are identical to tags from the sample that were previously counted.

Various criteria may be set for choosing when to disregard an identical tag from a single sample. In certain embodiments, a defined percentage of the tags that are counted must be unique. If more tags than this threshold are not unique, they are disregarded. For example, if the defined percentage requires that at least 50% are unique, identical tags are not counted until the percentage of unique tags exceeds 50% for the sample. In other embodiments, the threshold number of unique tags is at least about 60%. In other embodiments, the threshold percentage of unique tags is at least about 75%, or at least about 90%, or at least about 95%, or at least about 98%, or at least about 99%. A threshold may be set at 90% for chromosome 21. If 30M tags are aligned to chromosome 21, then at least 27M of them must be unique. If 3M counted tags are not unique and the 30 million and first tag is not unique, it is not counted. The choice of the particular threshold or other criterion used to determine when not to count further identical tags can be selected using appropriate statistical analysis. One factor influencing this threshold or other criterion is the relative amount of sequenced sample to the size of the genome to which tags can be aligned. Other factors include the size of the reads and similar considerations.

In one embodiment, the number of test sequence tags mapped to a sequence of interest is normalized to the known length of a sequence of interest to which they are mapped to provide a test sequence tag density ratio. As described for the qualified samples, normalization to the known length of a sequence of interest is not required, and may be included as a step to reduce the number of digits in a number to simplify it for human interpretation. As all the mapped test sequence tags are counted in the test sample, the sequence tag coverage for a sequence of interest, e.g., a clinically-relevant sequence, in the test samples is determined, as are the sequence tag coverages for additional sequences that correspond to at least one normalizing sequence identified in the qualified samples.

In step 150, based on the identity of at least one normalizing sequence in the qualified samples, a test sequence dose is determined for a sequence of interest in the test sample. In various embodiments, the test sequence dose is computationally determined using the sequence tag coverages of the sequence of interest and the corresponding normalizing sequence as described herein. The computational apparatus responsible for this undertaking will electronically access the association between the sequence of interest and its associated normalizing sequence, which may be stored in a database, table, graph, or be included as code in program instructions.

As described elsewhere herein, the at least one normalizing sequence can be a single sequence or a group of sequences. The sequence dose for a sequence of interest in a test sample is a ratio of the sequence tag coverage determined for the sequence of interest in the test sample and the sequence tag coverage of at least one normalizing sequence determined in the test sample, wherein the normalizing sequence in the test sample corresponds to the normalizing sequence identified in the qualified samples for the particular sequence of interest. For example, if the normalizing sequence identified for chromosome 21 in the qualified samples is determined to be a chromosome, e.g., chromosome 14, then the test sequence dose for chromosome 21 (sequence of interest) is determined as the ratio of the sequence tag coverage for chromosome 21 in and the sequence tag coverage for chromosome 14 each determined in the test sample. Similarly, chromosome doses for chromosomes 13, 18, X, Y, and other chromosomes associated with chromosomal aneuploidies are determined. A normalizing sequence for a chromosome of interest can be one or a group of chromosomes, or one or a group of chromosome segments. As described previously, a sequence of interest can be part of a chromosome, e.g., a chromosome segment. Accordingly, the dose for a chromosome segment can be determined as the ratio of the sequence tag coverage determined for the segment in the test sample and the sequence tag coverage for the normalizing chromosome segment in the test sample, wherein the normalizing segment in the test sample corresponds to the normalizing segment (single or a group of segments) identified in the qualified samples for the particular segment of interest. Chromosome segments can range from kilobases (kb) to megabases (Mb) in size (e.g., about 1 kb to 10 kb, or about 10 kb to 100 kb, or about 100 kb to 1 Mb).

In step 155, threshold values are derived from standard deviation values established for qualified sequence doses determined in a plurality of qualified samples and sequence doses determined for samples known to be aneuploid for a sequence of interest. Note that this operation is typically performed asynchronously with analysis of patient test samples. It may be performed, for example, concurrently with the selection of normalizing sequences from qualified samples. Accurate classification depends on the differences between probability distributions for the different classes, i.e., type of aneuploidy. In some examples, thresholds are chosen from empirical distribution for each type of aneuploidy, e.g., trisomy 21. Possible threshold values that were established for classifying trisomy 13, trisomy 18, trisomy 21, and monosomy X aneuploidies as described in the Examples, which describe the use of the method for determining chromosomal aneuploidies by sequencing cfDNA extracted from a maternal sample comprising a mixture of fetal and maternal nucleic acids. The threshold value that is determined to distinguish samples affected for an aneuploidy of a chromosome can be the same or can be different from the threshold for a different aneuploidy. As is shown in the Examples, the threshold value for each chromosome of interest is determined from the variability in the dose of the chromosome of interest across samples and sequencing runs. The less variable the chromosome dose for any chromosome of interest, the narrower the spread in the dose for the chromosome of interest across all the unaffected samples, which are used to set the threshold for determining different aneuploidies.

Returning to the process flow associated with classifying a patient test sample, in step 160, the copy number variation of the sequence of interest is determined in the test sample by comparing the test sequence dose for the sequence of interest to at least one threshold value established from the qualified sequence doses. This operation may be performed by the same computational apparatus employed to measure sequence tag coverages and/or calculate segment doses.

In step 160, the calculated dose for a test sequence of interest is compared to that set as the threshold values that are chosen according to a user-defined "threshold of reliability" to classify the sample as a "normal" an "affected" or a "no call." The "no call" samples are samples for which a definitive diagnosis cannot be made with reliability. Each type of affected sample (e.g., trisomy 21, partial trisomy 21, monosomy X) has its own thresholds, one for calling normal (unaffected) samples and another for calling affected samples (although in some cases the two thresholds coincide). As described elsewhere herein, under some circumstances a no-call can be converted to a call (affected or normal) if fetal fraction of nucleic acid in the test sample is sufficiently high. The classification of the test sequence may be reported by the computational apparatus employed in other operations of this process flow. In some cases, the classification is reported in an electronic format and may be displayed, emailed, texted, etc. to interest persons.

In some embodiments, the determination of CNV comprises calculating a NCV or NSV that relates the chromosome or segment dose to the mean of the corresponding chromosome or segment dose in a set of qualified samples as described above. Then CNV can be determined by comparing the NCV/NSV to a predetermined copy number evaluation threshold value.

The copy number evaluation threshold can be chosen to optimize the rate of false positives and false negatives. The higher the copy number evaluation threshold, the less likely the occurrence of a false positive. Similarly, the lower the threshold, the less likely the occurrence of a false negative. Thus, a trade-off exists between a first ideal threshold above which only true positives are classified, and a second ideal threshold below which only true negatives are classified.

Thresholds are set largely depending on the variability in chromosome doses for a particular chromosome of interest as determined in a set of unaffected samples. The variability is dependent on a number of factors, including the fraction of fetal cDNA present in a sample. The variability (CV) is determined by the mean or median and standard deviation for chromosome doses across a population of unaffected samples. Thus, the threshold (s) for classifying aneuploidy use NCVs, according to:

$$NCV_{ij} = \frac{x_{ij} - \hat{\mu}_j}{\hat{\sigma}_j}$$

(where $\hat{\mu}_j$ and $\hat{\sigma}_j$ are the estimated mean and standard deviation, respectively, for the j-th chromosome dose in a set of qualified samples, and $x_{ij}$ is the observed j-th chromosome dose for test sample i.)

with an associated fetal fraction as:

$$FF_{ij} = 2 \times \left| \frac{NCV_{ij} \times \hat{\sigma}_j}{\hat{\mu}_j} \right| = 2 \times NCV \times CV$$

Thus, for every NCV of a chromosome of interest, an expected fetal fraction associated with the given NCV value can be calculated from the CV based on the mean and standard deviation of the chromosome ratio for the chromosome of interest across a population of unaffected samples.

Subsequently, based on the relationship between fetal fraction and NCV values, a decision boundary can be chosen above which samples are determined to be positive (affected) based on the normal distribution quantiles. As described above, a threshold that is set for optimal trade-off between the detection of true positives and rate of false negative results. Accordingly, the threshold that is set is chosen to optimize the false positive and false negatives.

Certain embodiments provide a method for providing prenatal diagnosis of a fetal chromosomal aneuploidy in a biological sample comprising fetal and maternal nucleic acid molecules. The diagnosis is made based on obtaining sequence information from at least a portion of the mixture of the fetal and maternal nucleic acid molecules derived from a biological test sample, e.g., a maternal plasma sample, computing from the sequencing data a normalizing chromosome dose for one or more chromosomes of interest, and/or a normalizing segment dose for one or more segments of interest, and determining a statistically significant difference between the chromosome dose for the chromosome of interest and/or the segment dose for the segment of interest, respectively, in the test sample and a threshold value established in a plurality of qualified (normal) samples, and providing the prenatal diagnosis based on the statistical difference. As described in step 160 of the method, a diagnosis of normal or affected is made. A "no call" is provided in the event that the diagnosis for normal or affected cannot be made with confidence.

In some embodiments, two thresholds can be chosen. A first threshold is chosen to minimize the false positive rate, above which samples will be classified as "Affected", and a second threshold is chosen to minimize the false negative rate, below which samples will be classified as "unaffected". Samples having NCVs above the second threshold but below the first threshold can be classified as "Aneuploidy suspected" or "No call" samples, for which the presence or absence of aneuploidy can be confirmed by independent means. The region between the first and second thresholds can be referred to as a "no call" region.

In some embodiments, the suspected and no call thresholds are shown in Table 1. As can be seen, the thresholds of NCV vary across different chromosomes. In some embodiments, the thresholds vary according to the FF for the sample as explained above. Threshold techniques applied here contribute to improved sensitivity and selectivity in some embodiments.

TABLE 1

Suspected and Affected NCV Thresholds
Bracketing No-Call Ranges

|  | Suspected | Affected |
|---|---|---|
| Chr 13 | 3.5 | 4.0 |
| Chr 18 | 3.5 | 4.5 |
| Chr 21 | 3.5 | 4.0 |
| Chr X (XO, XXX) | 4.0 | 4.0 |
| Chr Y (XX vs XY) | 6.0 | 6.0 |

Determining Sequence Coverage

General Process for Determining Sequence Coverage

Some embodiments disclosed provide methods to determine sequence coverage quantities with low noise and high signal, providing data to determine various genetic conditions related to copy number and CNV with improved sensitivity, selectivity, and/or efficiency relative to sequence coverage quantities obtained by conventional methods. In certain embodiments, sequences from a test sample are processed to obtain sequence coverage quantities.

The process makes use of certain information available from other sources. In some implementations, all of this information is obtained from a training set of samples known to be unaffected (e.g., not aneuploid). In other embodiments, some or all of the information is obtained from other test samples, which may be provided "on-the-fly" as multiple samples are analyzed in the same process.

In certain embodiments, sequence masks are employed to reduce data noise. In some embodiments, both the sequence of interest and its normalizing sequences are masked. In some embodiments, different masks may be employed when different chromosomes or segments of interest are considered. For example one mask (or group of masks) may be employed when chromosome 13 is the chromosome of interest and a different mask (or group of masks) may be employed with chromosome 21 is the chromosome of interest. In certain embodiments, the masks are defined at the resolution of bins. Therefore, in one example, the mask resolution is 100 kb. In some embodiments, a distinct mask may be applied to chromosome Y. The masked exclusion regions for chromosome Y may be provided at a finer resolution (1 kb) than for other chromosomes of interest, as described in U.S. Provisional Patent Application No. 61/836,057, filed Jun. 17, 2013. The masks are provided in the form of files identifying excluded genomic regions.

In certain embodiments, the process utilizes an expectation value of normalized coverage to remove bin-to-bin variation in the profile of a sequence of interest, which variation is uninformative for determination of CNV for the test sample. The process adjusts normalized coverage quantities according to the expectation value of normalized coverage for each bin across the entire genome, or at least the bins of the robust chromosomes in the reference genome (for use in operation 317 below). The expectation value may be determined from a training set of unaffected samples. As an example, the expectation value may be a median value across the training set samples. The expected coverage values of the samples may be determined as the number of unique non-redundant tags aligned to a bin divided by the total number of unique non-redundant tags aligned to all bins in the robust chromosomes of the reference genome.

Figure 2:
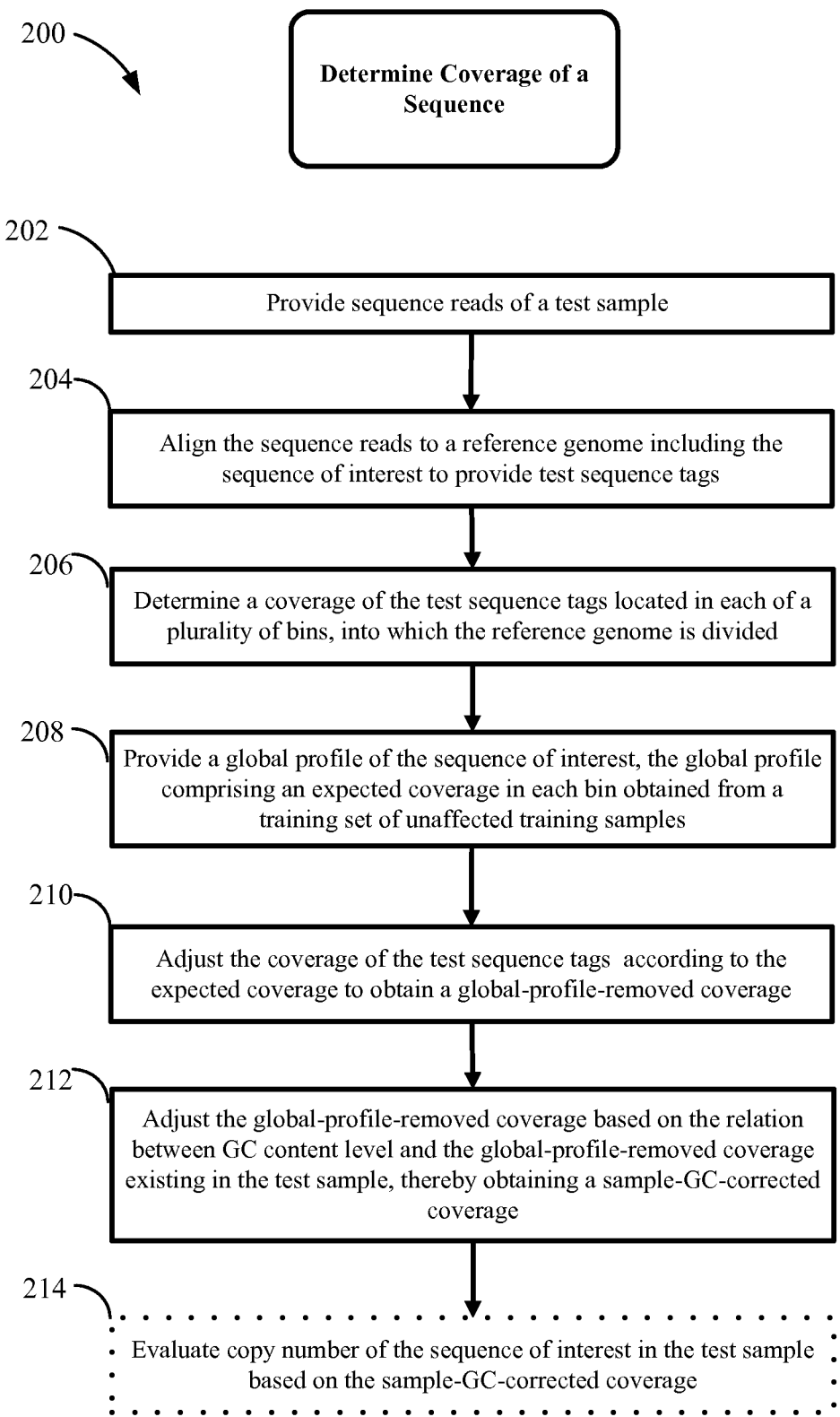
FIG. 2 depicts a flowchart of a process for determining coverage of a nucleic acid sequence of interest used for evaluation of the copy number.

FIG. 2 depicts a flowchart of a process 200 for determining coverage of a sequence of interest, which is used to evaluate the copy number of the sequence of interest in a test sample in block 214. This process removes systematic variation common across unaffected training samples, which variation increases noise in the analysis for CNV evaluation. It also removes GC bias specific to a test sample, thereby increasing the signal-to-noise ratio in data analysis.

The process starts by providing sequence reads of the test sample as indicated in block 202. In some embodiments the sequence reads are obtained by sequencing DNA segments obtained from a pregnant woman's blood including cfDNA of the mother and the fetus. The process proceeds to align the sequence reads to a reference genome including the sequence of interest, providing test sequence tags. Block 204. Testing sequence tag counts in each bin on the reference sequence defines the coverage of the bin. Block 206. In some embodiments, reads that are aligned to more than one site are excluded. In some embodiments multiple reads align to the same site are excluded or reduced to a single read count. In some embodiments, reads aligned to excluded sites are also excluded. Therefore, in some embodiments, only the uniquely aligned, non-redundant tags aligned to non-excluded sites are counted to provide a non-excluded site count (NES count) for determining the coverage of each bin. In some embodiments, the coverage of each bin is divided by the coverage of the normalizing sequence in the same sample, providing a normalized coverage quantity.

Process 200 then provides a global profile of the sequence of interest. The global profile comprises an expected coverage in each bin obtained from a training set of unaffected training samples. Block 208. Process 200 removes variation common in the training sample by adjusting the normalized coverage quantity of the test sequence tags according to the expected coverage to obtain a global-profile-corrected coverage. Block 210. In some embodiments, the expected coverage obtained from the training set provided in block 208 is a median of across the training samples. In some embodiments, operation 210 adjusts the normalized coverage quantity by subtracting the expected coverage from the normalized coverage. In other embodiments, operation 210 divides the normalized coverage quantity by the expected coverage of each bin to produce global-profile corrected coverage.

Furthermore, process 200 removes GC bias specific to the test sample by further adjusting the coverage quantity that has been adjusted to remove the global profile. As shown in block 212, the process adjusts the global-profile-corrected coverage based on the relation between GC content level and the global-profile-corrected coverage existing in the test sample, thereby obtaining a sample-GC-corrected coverage. After adjusting for systematic variation common in the unaffected training samples and within-subject GC bias, the process provides coverage quantities to evaluate CNV of the sample with improved sensitivity and specificity.

Details of an Exemplary Process for Determining Sequence Coverage

Figure 3A:
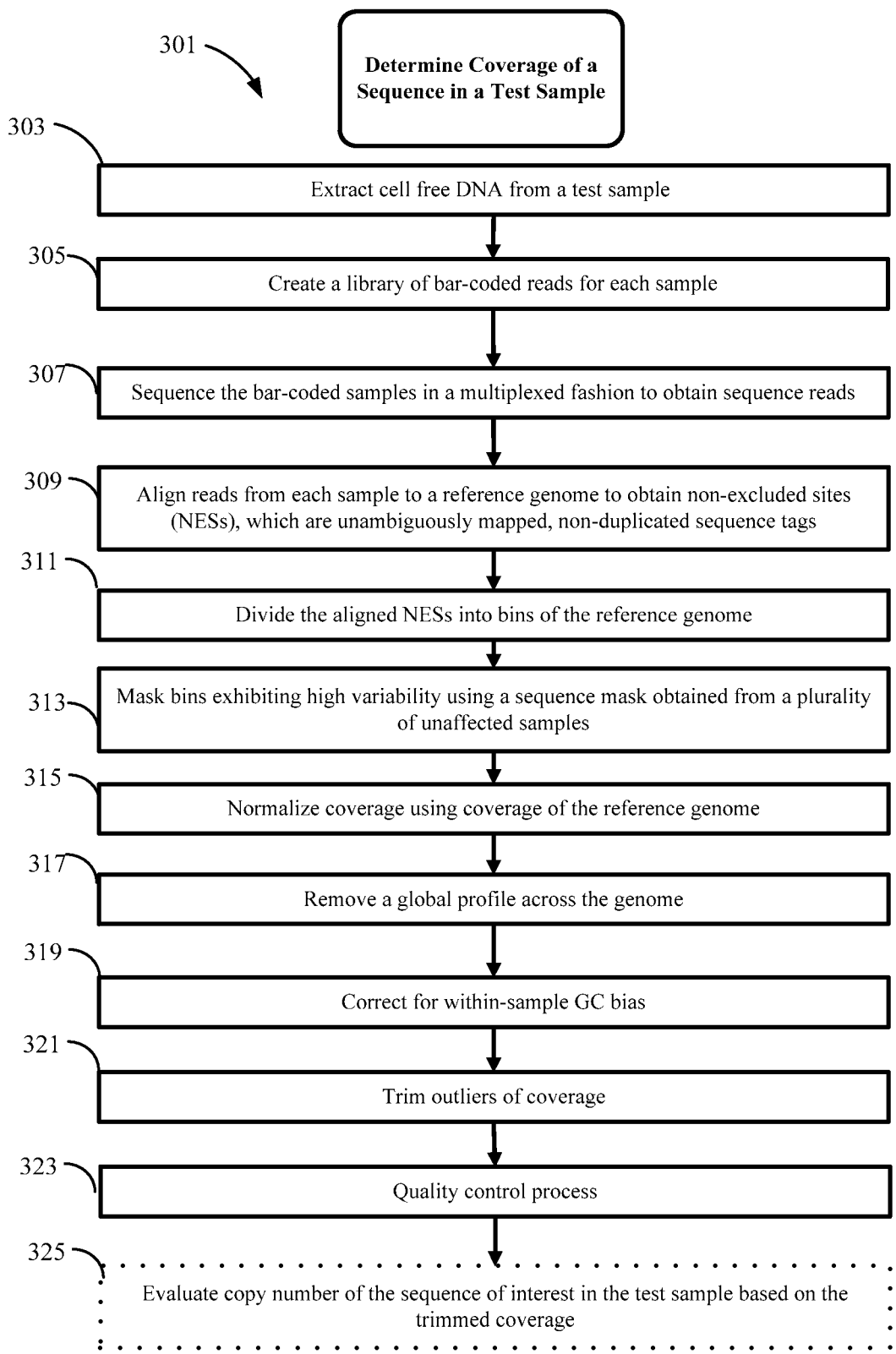
FIG. 3A shows a flowchart of an example of a process for reducing the noise in sequence data from a test sample.

FIG. 3A presents an example of a process 301 for reducing the noise in sequence data from a test sample. FIGS. 3B-3J present data analyses at various stages of the process. As shown in FIG. 3A, the depicted process begins with extraction of cfDNA from one or more samples. See block 303. Suitable extraction processes and apparatus are described elsewhere herein. In some embodiments, a process described in U.S. Patent Application No. 61/801,126, filed Mar. 15, 2013 (incorporated herein by reference in its entirety) extracts cfDNA. In some implementations, the apparatus processes cfDNA from multiple samples together to provide multiplexed libraries and sequence data. See blocks 305 and 307 in FIG. 3A. In some embodiments, the apparatus processes cfDNA from eight or more test samples in parallel. As described elsewhere herein, a sequencing system may process extracted cfDNA to produce a library of coded (e.g., bar coded) cfDNA fragments. A sequencer sequences library of cfDNA to produce a very large number of sequence reads. Per sample coding allows demultiplexing of the reads in multiplexed samples. Each of the eight or more samples may have hundreds of thousands or millions of reads. The process may filter the reads prior to additional operations in FIG. 3A. In some embodiments, read filtering is a quality-filtering process enabled by software programs implemented in the sequencer to filter out erroneous and low quality reads. For example, Illumina's Sequencing Control Software (SCS) and Consensus Assessment of Sequence and Variation software programs filter out erroneous and low quality reads by converting raw image data generated by the sequencing reactions into intensity scores, base calls, quality scored alignments, and additional formats to provide biologically relevant information for downstream analysis.

After the sequencer or other apparatus generates the reads for a sample, an element of the system computationally aligns the reads to a reference genome. See block 309. Alignment is described elsewhere herein. The alignment produces tags, which contain read sequences with annotated location information specifying unique positions on the reference genome. In certain implementations, the system conducts a first pass alignment without regard for duplicate reads—two or more reads having identical sequences—and subsequently removes duplicated reads or counts duplicate reads as a single read to produce non-duplicated sequence tags. In other implementations, the system does not remove duplicated reads. In some embodiments, the process removes from consideration reads that are aligned to multiple locations on the genome to produce uniquely aligned tags. In some embodiments, uniquely aligned, non-redundant sequence tags mapped to non-excluded sites (NESs) are accounted for to yield non-excluded site counts (NES counts), which provide data to estimate coverage.

As explained elsewhere, excluded sites are sites found in regions of a reference genome that have been excluded for the purpose of counting sequence tags. In some embodiments, excluded sites are found in regions of chromosomes that contain repetitive sequences, e.g., centromeres and telomeres, and regions of chromosomes that are common to more than one chromosome, e.g., regions present on the Y-chromosome that are also present on the X chromosome. Non-excluded sites (NESs) are sites that are not excluded in a reference genome for the purpose of counting sequence tags.

Next, the system divides the aligned tags into bins on the reference genome. See block 311. The bins are spaced along the length of the reference genome. In some embodiments, the entire reference genome is divided into contiguous bins, which may have defined equal size (e.g., 100 kb). Alternatively, the bins may have a length determined dynamically, possibly on a per-sample basis. Sequencing depth impacts optimal bin size selection. Dynamically sized bins may have their size determined by the library size. For example, the bin size may be determined to be the sequence length required to accommodate 1000 tags, on average.

Each bin has a number of tags from a sample under consideration. This number of tags, which reflects the "coverage" of the aligned sequence, serves as a starting point for filtering and otherwise cleaning the sample data to reliably determine copy number variation in the sample. FIG. 3A shows the cleaning operations in blocks 313 to 321.

In the embodiment depicted in FIG. 3A, the process applies a mask to the bins of the reference genome. See block 313. The system may exclude coverage in masked bins from consideration in some or all of the following process operations. In many cases, coverage values from masked bins are not considered any of the remaining operations in FIG. 3A.

In various implementations, one or more masks are applied to remove bins for regions of the genome found to exhibit high variability from sample to sample. Such masks are provided for both chromosomes of interest (e.g., chr13, 18, and 21) and other chromosomes. As explained elsewhere, a chromosome of interest is the chromosome under consideration as potentially harboring a copy number variation or other aberration.

In some implementations, masks are identified from a training set of qualified samples using the following approach. Initially, each training set sample is processed and filtered according to operations 315 through 319 in FIG. 3A. The normalized and corrected coverage quantities are then noted for each bin and statistics such as standard deviation, median absolute deviation, and/or coefficient of variation are calculated for each bin. Various filter combinations may be evaluated for each chromosome of interest. The filter combinations provide one filter for the bins of the chromosome of interest and a different filter for the bins of all other chromosomes.

In some implementations, the choice of a normalizing chromosome (or group of chromosomes) is reconsidered after obtaining masks (e.g., by choosing cut-offs for a chromosome of interest as described above). After applying the sequence mask, the process of choosing a normalizing chromosome or chromosomes may be conducted as described elsewhere herein. For example, all possible combinations of chromosomes are evaluated as normalizing chromosomes and ranked according to their ability to discriminate affected and unaffected samples. This process may (or may not) find a different optimal normalizing chromosome or group of chromosomes. In other embodiments, normalizing chromosomes are those that result in the smallest variability in sequence dose for the sequence of interest across all qualified samples. If a different normalizing chromosome or group of chromosomes is identified, the process optionally executes the above described identification of bins to filter. Possibly the new normalizing chromosome(s) result in different cut-offs.

In certain embodiments, a different mask is applied for chromosome Y. An example of a suitable chromosome Y mask is described in U.S. Provisional Patent Application No. 61/836,057, filed Jun. 17, 2013, which is incorporated herein by reference for all purposes.

After the system computationally masks the bins, it computationally normalizes the coverage values in the bins that are not excluded by the masks. See block 315. In certain embodiments, the system normalizes the test sample coverage values in each bin (e.g., NES counts per bin) against most or all of the coverage in reference genome or a portion thereof (e.g., the coverage in the robust chromosomes of the reference genome). In some cases, the system normalizes the test sample coverage values (per bin) by dividing the count for the bin under consideration by the total number of all non-excluded sites aligning to all robust chromosomes in the reference genome. In some embodiments, the system normalizes the test sample coverage values (per bin) by performing a linear regression. For instance, the system first calculates coverages for a subset of bins in robust chromosomes as $y_a = \text{intercept} + \text{slope} \cdot \text{gwp}_a$, where $y_a$ is coverage for bin a, and $\text{gwp}_a$ is the global profile for the same bin. The system then calculates the normalized coverages $z_b$ as: $z_b = y_b/(\text{intercept}+\text{slope}*gwp_b)-1$.

As explained above, a robust chromosome is one that is unlikely to be aneuploid. In certain embodiments, the robust chromosomes are all autosomal chromosomes other than chromosomes 13, 18, and 21. In some embodiments, the robust chromosomes are all autosomal chromosomes other than chromosomes determined to deviate from a normal diploid genome.

A bin's transformed count value or coverage is referred to as a "normalized coverage quantity" for further processing. The normalization is performed using information unique to each sample. Typically, no information from a training set is used. Normalization allows coverage quantities from samples having different library sizes (and consequently different numbers of reads and tags) to be treated on equal footing. Some of the subsequent process operations use coverage quantities derived from training samples which may be sequenced from libraries that are larger or smaller than the libraries used for a test sample under consideration. Without normalization based on the number of reads aligned to the entire reference genome (or at least the robust chromosomes), treatment using parameters derived from a training set might not be reliable or generalizable in some implementations.

Figure 3B:
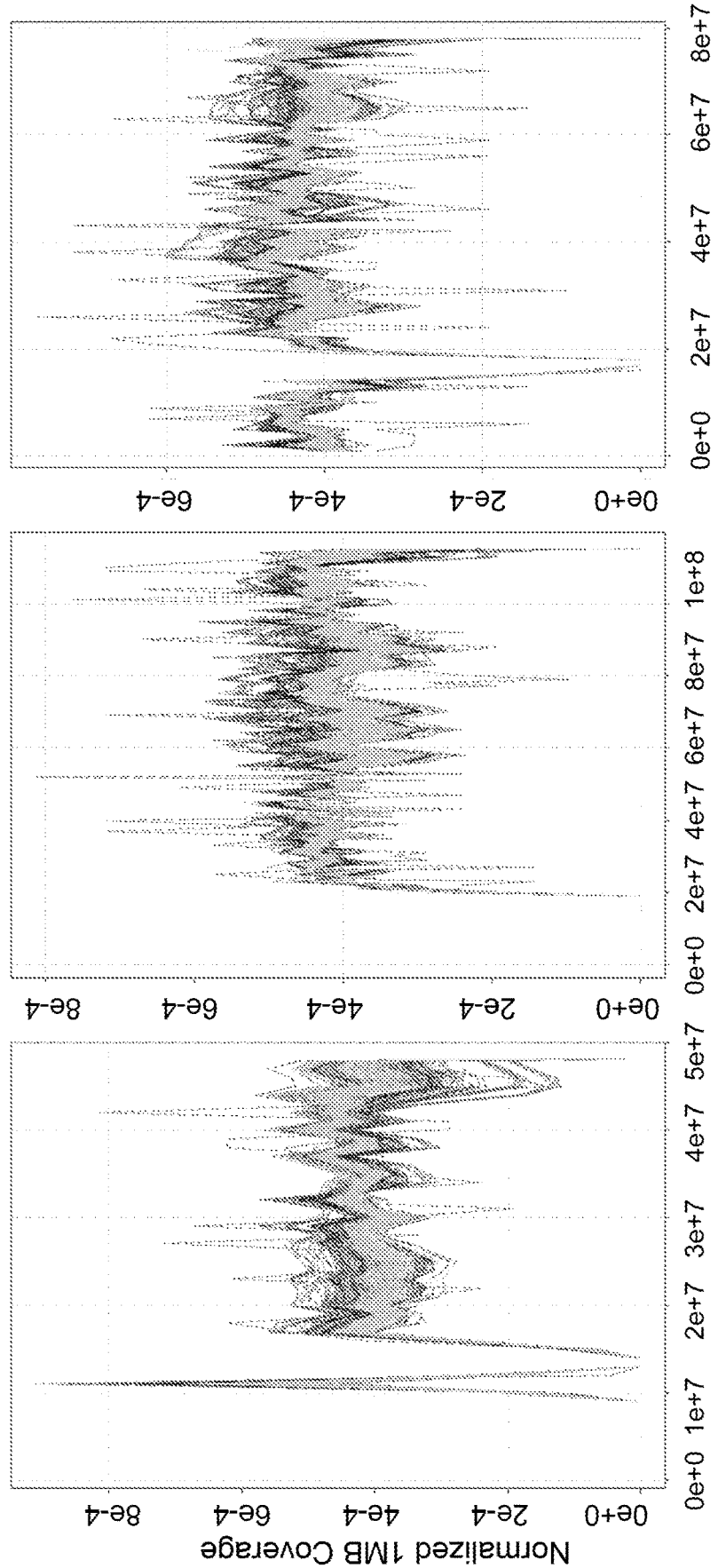
FIGS. 3B-3K present analyses of data obtained at various stages of the process depicted in FIG. 3A.
Figure 3C:
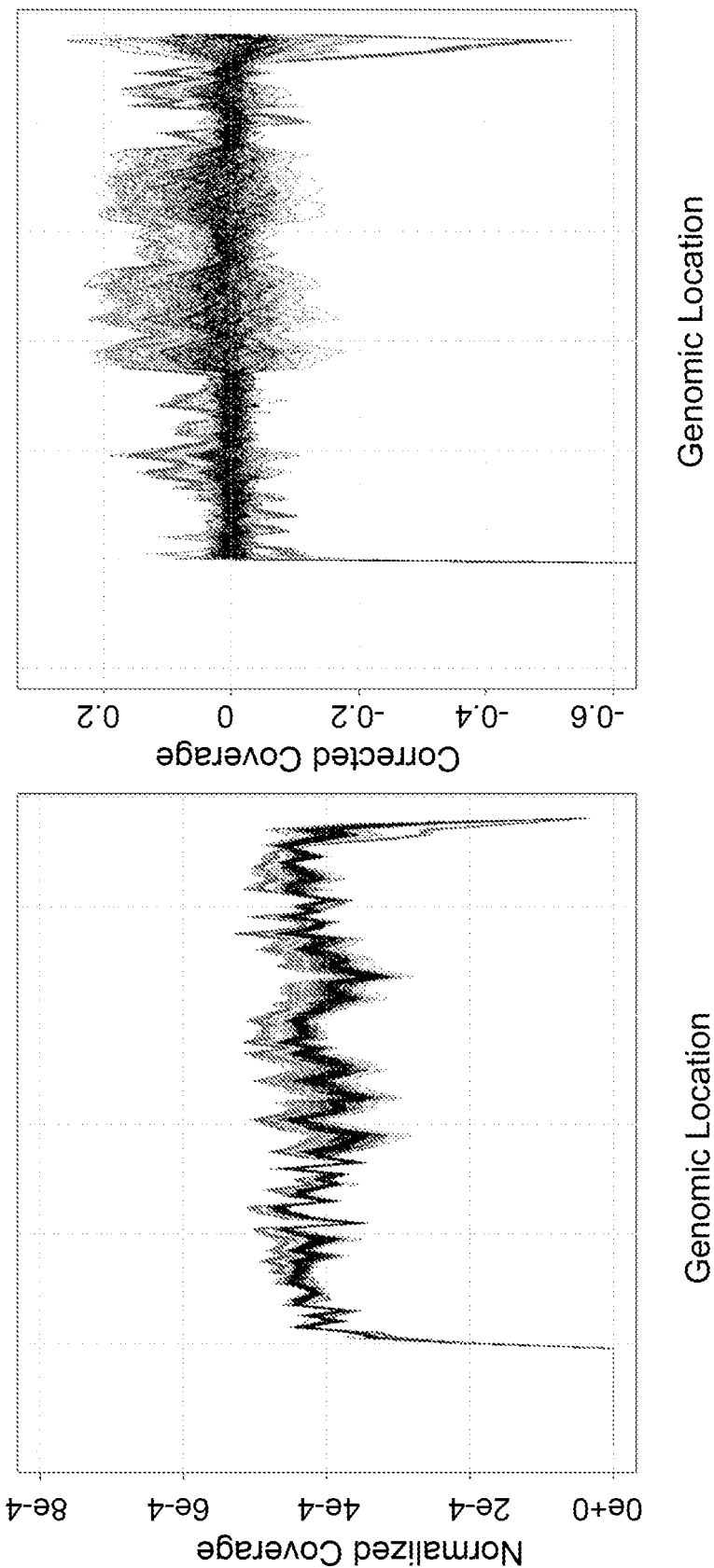

FIG. 3B illustrates the coverage across chromosomes 21, 13, and 18 for many samples. Some of the samples were processed differently from one another. As a consequence, one can see a wide sample-to-sample variation at any given genomic position. Normalization removes some of the sample-to-sample variation. The left panel of FIG. 3C depicts normalized coverage quantities across an entire genome.

In the embodiment of FIG. 3A, the system removes or reduces a "global profile" from the normalized coverage quantities produced in operation 315. See block 317. This operation removes systematic biases in the normalized coverage quantities arising from the structure of the genome, the library generation process, and the sequencing process. In addition, this operation is designed to correct for any systematic linear deviation from the expected profile in any given sample.

In some implementations, the global profile removal involves dividing the normalized coverage quantity of each bin by a corresponding expected value of each bin. In other embodiments, the global profile removal involves subtracting an expected value of each bin from the normalized coverage quantity of each bin. The expected value may be obtained from a training set of unaffected samples (or unaffected female samples for the X chromosome). Unaffected samples are samples from individuals known not to have an aneuploidy for the chromosome of interest. In some implementations, the global profile removal involves subtracting the expected value of each bin (obtained from a training set) from the normalized coverage quantity of each bin. In some embodiments, the process uses median values of normalized coverage quantities for each bin as determined using the training set. In other words, the median values are the expected values.

In some embodiments, the global profile removal is implemented using a linear correction for the dependence of the sample coverage on the global profile. As indicated, the global profile is an expected value for each bin as determined from the training set (for example the median value for each bin). These embodiments may employ a robust linear model obtained by fitting the test sample's normalized coverage quantities against the global median profile obtained for each bin. In some embodiments, the linear model is obtained by regressing the sample's observed normalized coverage quantities against the global median (or other expectation value) profile.

The linear model is based on an assumption that sample coverage quantities have a linear relationship with the global profile values, which linear relationship should hold for both robust chromosomes/regions and a sequence of interest. See FIG. 3D. In such case, a regression of the sample normalized coverage quantities on the global profile's expected coverage quantities will produce a line having a slope and intercept. In certain embodiments, the slope and intercept of such line is used to calculate a "predicted" coverage quantity from the global profile value for a bin. In some implementations, a global profile correction involves modeling each bin's normalized coverage quantity by the predicted coverage quantities for the bin. In some implementations, coverages of the test sequence tags are adjusted by: (i) obtaining a mathematical relation between the coverage of the test sequence tags versus the expected coverage in a plurality of bins in one or more robust chromosomes or regions, and (ii) applying the mathematical relation to bins in the sequence of interest. In some implementations, the coverages in a test sample are corrected for variation using a linear relationship between the expected coverage values from unaffected training samples and coverage values for the test sample in robust chromosomes or other robust regions of the genome. The adjustment results in global-profile-corrected coverages. In some cases, the adjustment involves obtaining coverages for a test sample for a subset of bins in robust chromosomes or regions as follows:

$$y_a = \text{intercept}+\text{slope}*gwp_a$$

where ya is coverage of bin a for the test sample in one or more robust chromosomes or regions, and gwpa is the global profile for bin a for unaffected training samples. The process then computes a global-profile-corrected coverage zb for a sequence or region of interest as:

$$z_b = y_b/(\text{intercept}+\text{slope}*gwp_b)-1$$

where yb is the observed coverage of bin b for the test sample in the sequence of interest (which may reside outside a robust chromosome or region), and gwpb is the global profile for bin b for unaffected training samples. The denominator (intercept+slope*gwpb) is the coverage for bin b that is predicted to be observed in unaffected test samples based on the relationship estimated from robust regions of the genome. In the case of a sequence of interest harboring a copy number variation, the observed coverage and hence the global-profile-corrected coverage value for bin b will deviate significantly from the coverage of an unaffected sample. For example, the corrected coverage zb would be proportional to fetal fraction in the case of trisomic sample for bins on the affected chromosome. This process normalizes within sample by computing intercept and slope on robust chromosomes, and then evaluates how the genomic region of interest deviates from a relationship (as described by the slope and the intercept) that holds for robust chromosomes within the same sample.

Figure 3D:
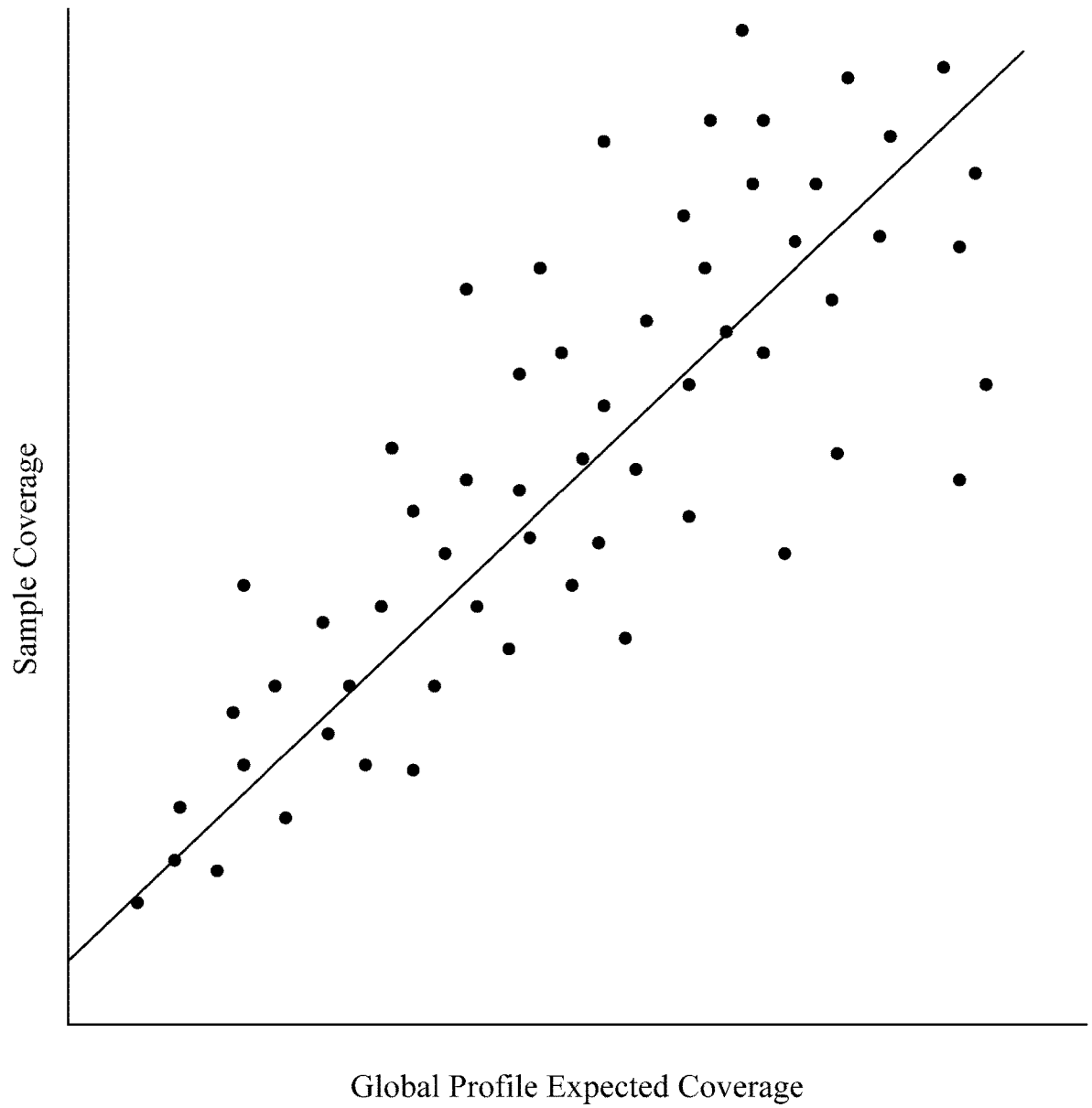

The slope and intercept are obtained from a line as shown in FIG. 3D. An example of global profile removal is depicted in FIG. 3C. The left panel shows a high bin-to-bin variation in normalized coverage quantities across many samples. The right panel shows the same normalized coverage quantities after global profile removal as described above.

Figure 3E:
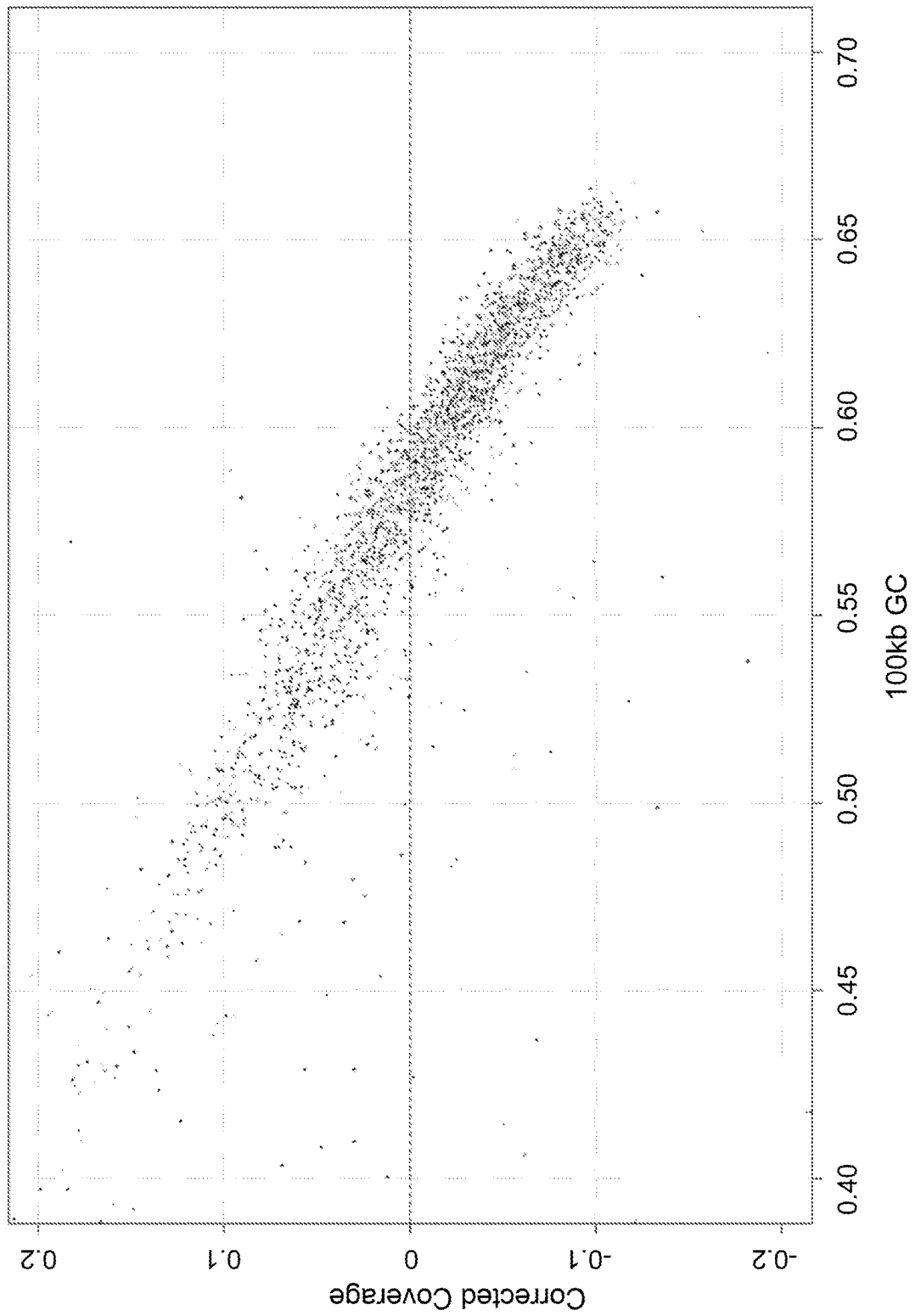
Figure 3F:
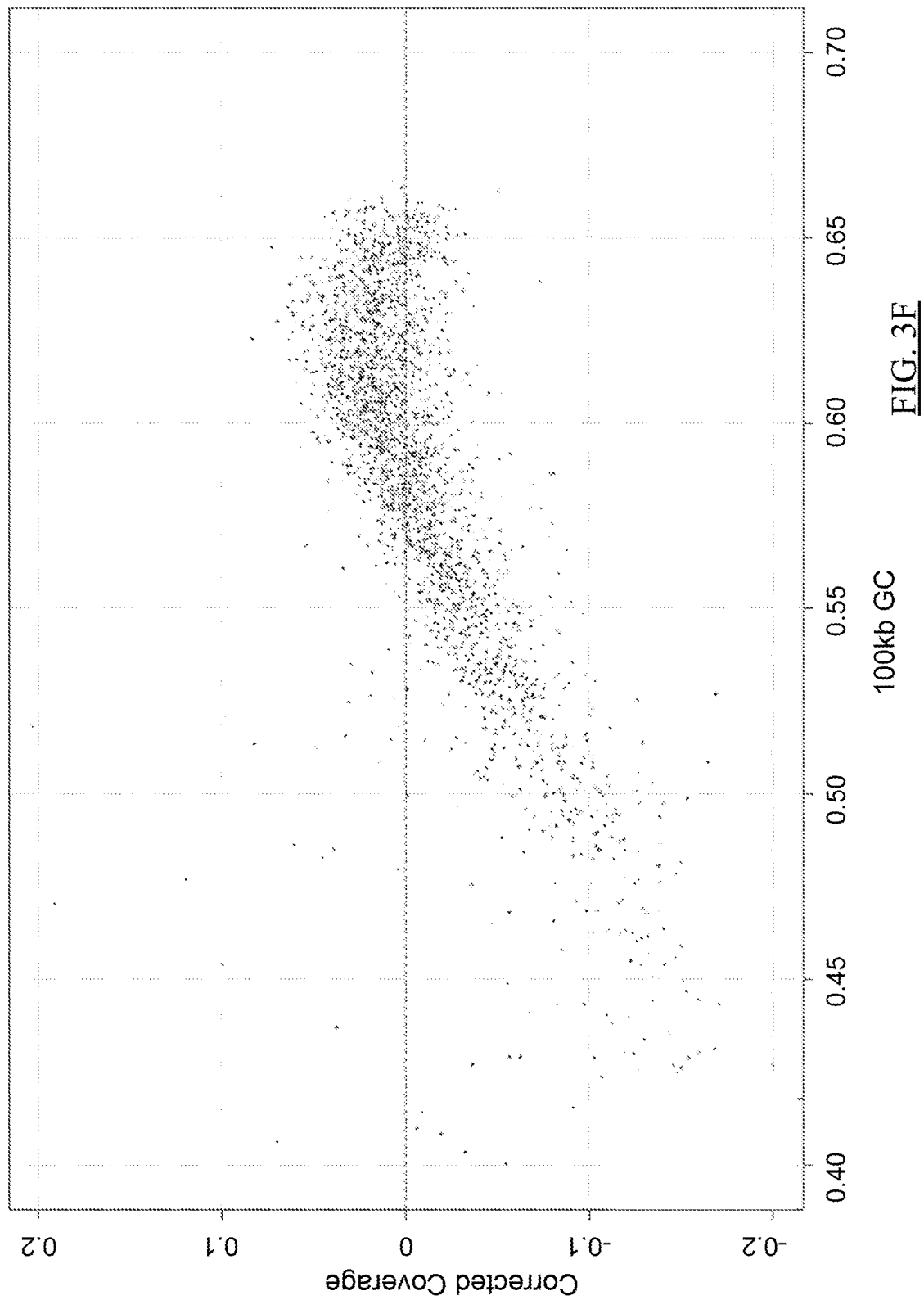
Figure 3G:
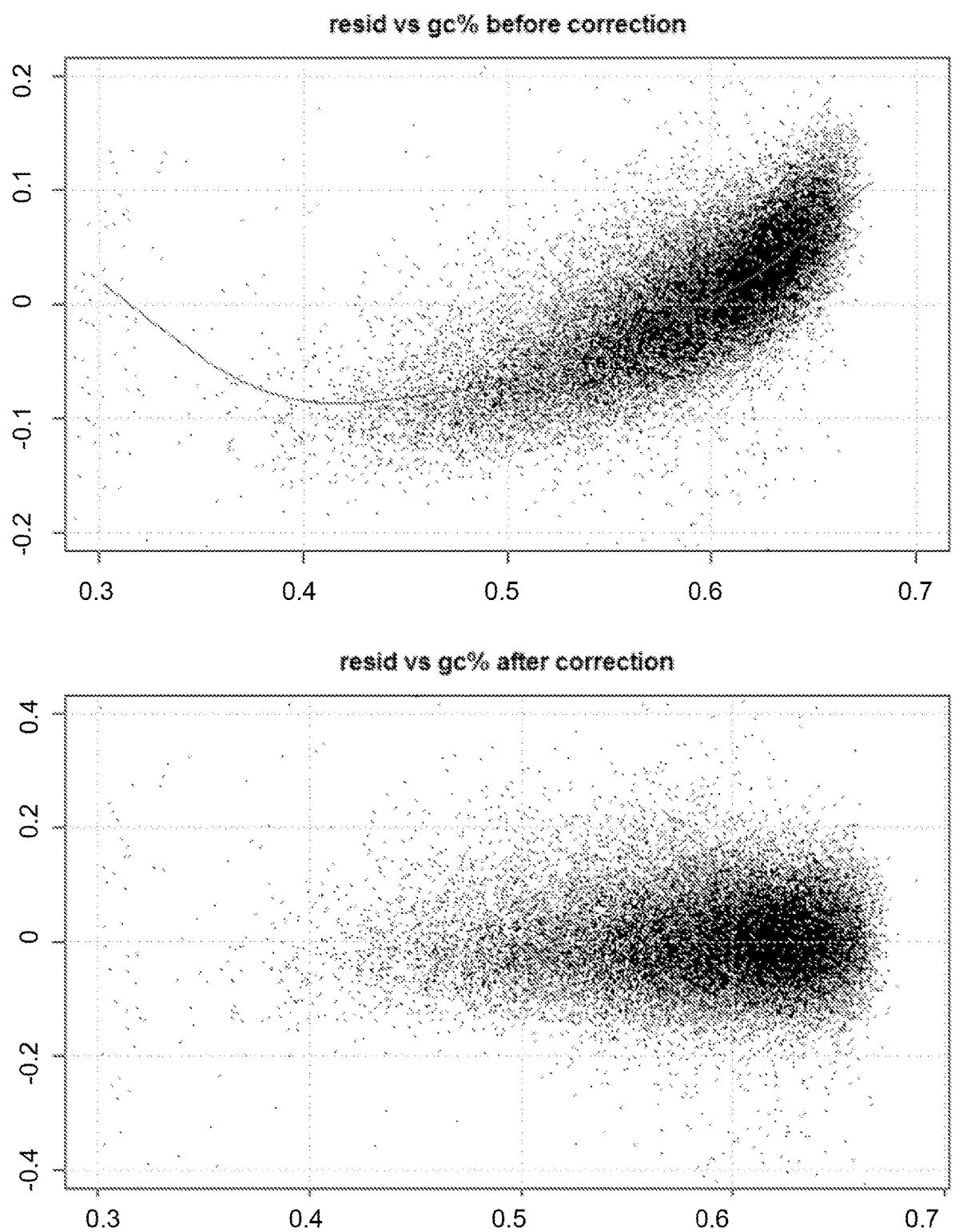

After the system removes or reduces the global profile variations at block 317, it corrects for in-sample GC (guanine-cytosine) content variations. See block 319. Every bin has its own fractional contribution from GC. The fraction is determined by dividing the number of G and C nucleotides in a bin by the total number of nucleotides in a bin (e.g., 100,000). Some bins will have greater GC fractions than others. As shown in FIGS. 3E and 3F, different samples exhibit different GC biases. These differences and their corrections will be explained further below. FIGS. 3E-G show global profile corrected, normalized coverage quantity (per bin) as a function of GC fraction (per bin). Surprisingly, different samples exhibit different GC dependence. Some samples show monotonically decreasing dependence (as in FIG. 3E), while others exhibit a comma shaped dependence (as in FIGS. 3F and 3G). Because these profiles may be unique for each sample, the correction described in this step is performed separately and uniquely for each sample.

In some embodiments, the system computationally arranges bins on the basis of GC fraction as illustrated in FIGS. 3E-G. It then corrects the global profile corrected, normalized coverage quantity of a bin using information from other bins with similar GC contents. This correction is applied to each unmasked bin.

In some processes, each bin is corrected for GC content in the following way. The system computationally selects bins having GC fractions similar to those of a bin under consideration and then determines a correction parameter from information in the selected bins. In some embodiments, those bins having similar GC fractions are selected using an arbitrarily defined cut-off value of similarity. In one example, 2% of all bins are selected. These bins are the 2% having GC content bins most similar to the bin under consideration. For example, the 1% of bins having slightly more GC content and 1% having slightly less GC content are selected.

Using the selected bins, the system computationally determines a correction parameter. In one example, the correction parameter is a representative value of the normalized coverage quantities (after global profile removal) in the selected bins. Examples of such representative value include the median or mean of the normalized coverage quantities in the selected bins. The system applies a calculated correction parameter for a bin under consideration to the normalized coverage quantity (after global profile removal) for the bin under consideration. In some implementations, a representative value (e.g., median value) is subtracted from the normalized coverage quantity of the bin under consideration. In some embodiments, the median value (or other representative value) of normalized coverage quantities is selected using only the coverage quantities for robust autosomal chromosomes (all autosomes other than chromosomes 13, 18, and 21).

In one example using, e.g., 100 kb bins, each bin will have a unique value of GC fraction, and the bins are divided into groups based on their GC fraction content. For example, the bins are divided into 50 groups, where group boundaries correspond to (0, 2, 4, 6, . . . , and 100) quantiles of the % GC distribution. A median normalized coverage quantity is calculated for each group of bins from the robust autosomes mapping to the same GC group (in the sample), and then the median value is subtracted from the normalized coverage quantities (for all bins across the entire genome in the same GC group). This applies a GC correction estimated from robust chromosomes within any given sample to the potentially affected chromosomes within the same sample. For example, all bins on robust chromosomes having a GC content between 0.338660 and 0.344720 are grouped together, the median is calculated for this group and is subtracted from the normalized coverage of the bins within this GC range, which bins may be found anywhere on the genome (excluding chromosomes 13, 18, 21, and X). In certain embodiments, chromosome Y is excluded from this GC correction process.

Figure 3H:
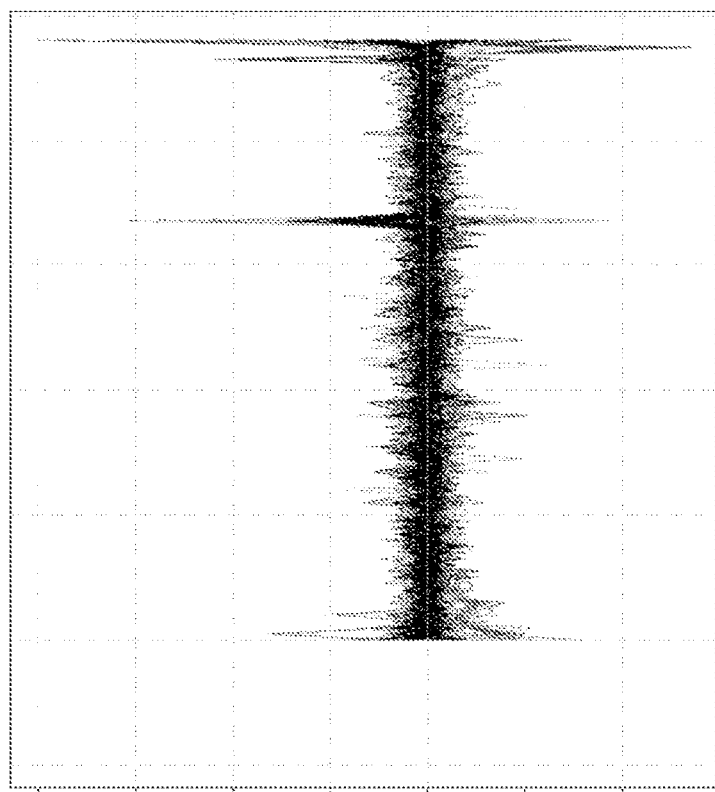
Figure 3H:
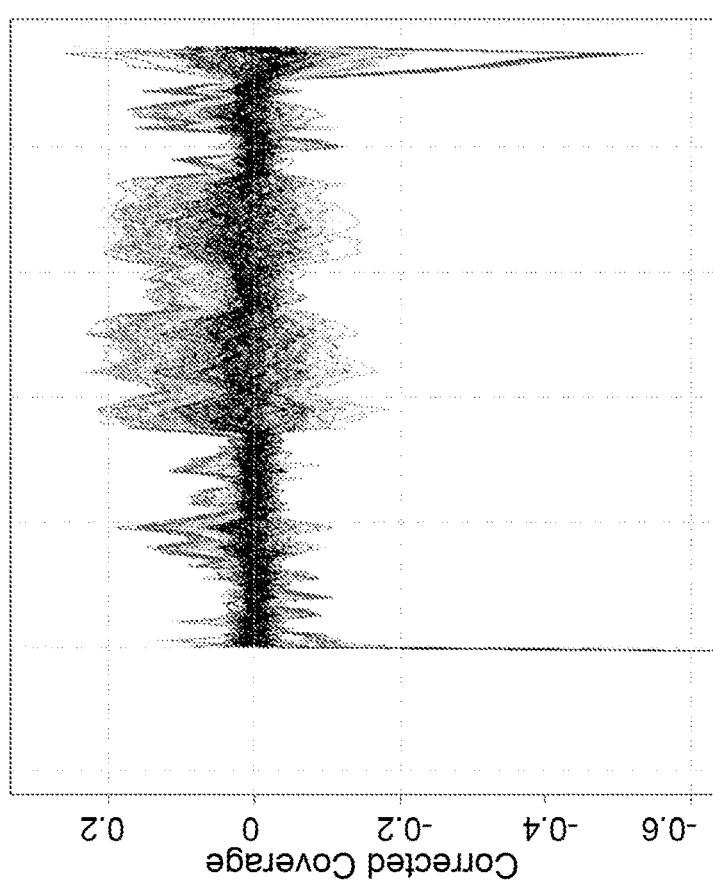
Figure 3I:
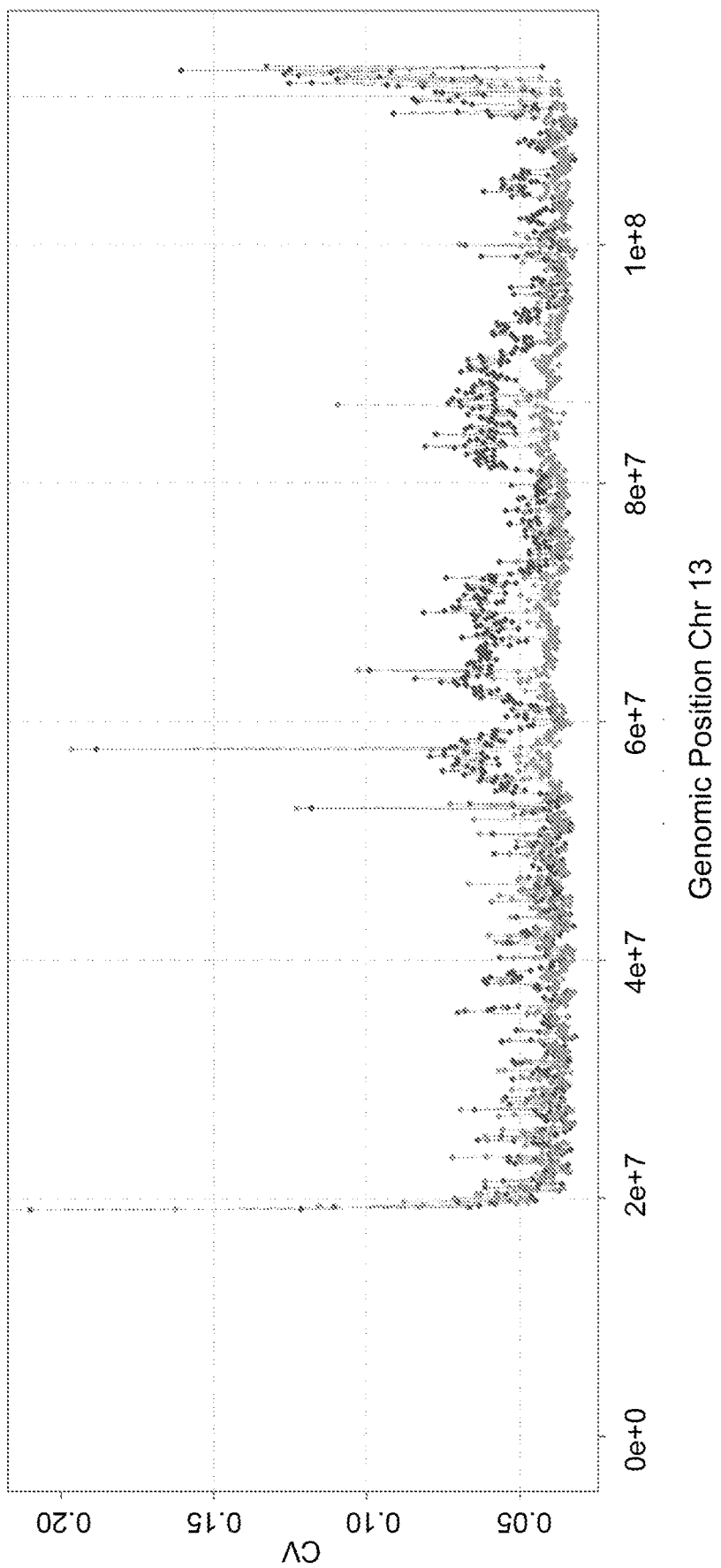

FIG. 3G shows application of a GC correction using median normalized coverage quantities as a correction parameter as just described. The left panel shows the uncorrected coverage quantities versus GC fraction profile. As shown, the profile has a non-linear shape. The right panel shows the corrected coverage quantities. FIG. 3H shows the normalized coverages for many samples before GC fraction correction (left panel) and after GC fraction correction (right panel). FIG. 3I shows the coefficient of variation (CV) of the normalized coverages for many test samples before GC fraction correction (red) and after GC fraction correction (green), where GC correction leads to substantially smaller variation in normalized coverages.

The above process is a relatively simple implementation of the GC correction. Alternative approaches to correcting for GC bias employ a spline or other non-linear fitting technique, which may be applied in the continuous GC space and does not involve binning coverage quantities by GC content. Examples of suitable techniques include continuous loess correction and smooth spline correction. A fitting function may be derived from bin-by-bin normalized coverage quantity versus GC content for the sample under consideration. The correction for each bin is calculated by applying the GC content for bin under consideration to the fitting function. For instance, the normalized coverage quantity may be adjusted by subtracting the expected coverage value of a spline at the GC content of the bin under consideration. Alternatively, the adjustment may be achieved by division of the expected coverage value according to the spline fit.

Figure 3J:
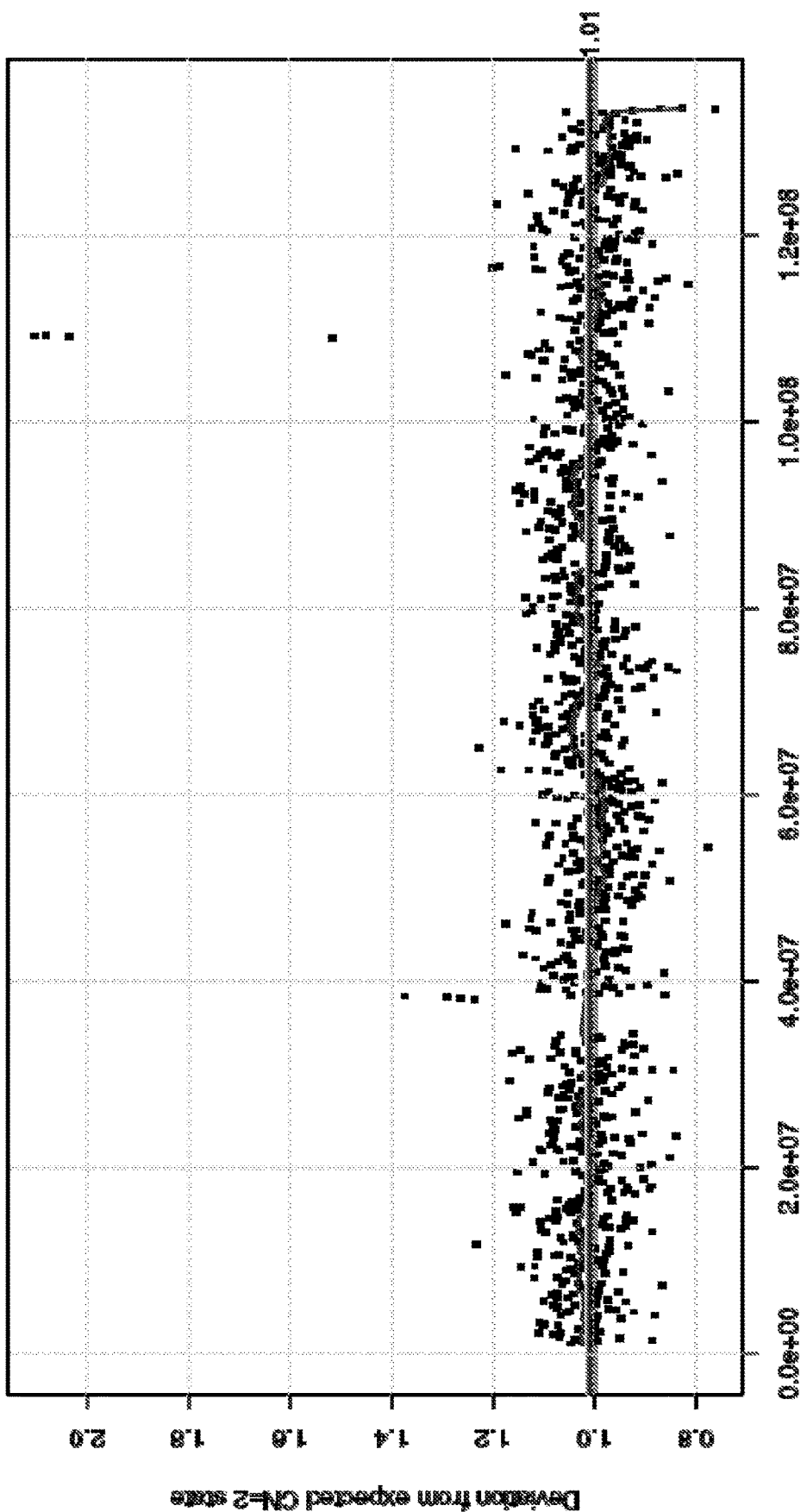

After correcting the GC-dependence in operation 319, the system computationally removes outlier bins in sample under consideration—See block 321. This operation may be referred to as single sample filtering or trimming. FIG. 3J shows that even after GC correction, the coverage still has sample-specific variation within small regions. See for example the coverage at position 1.1 e8 on chromosome 12 where an unexpectedly high deviation from the expected value results. It is possible that this deviation results from a small copy number variation in the material genome. Alternatively, this may be due to technical reasons in sequencing unrelated to copy number variation. Typically, this operation is only applied to the robust chromosomes.

As one example, the systems computationally filters any bins having a GC corrected normalized coverage quantity of more than 3 median absolute deviations from the median of the GC corrected normalized coverage quantity across all bins in the chromosome harboring the bin under consideration for filtering. In one example, the cut-off value is defined as 3 median absolute deviations adjusted to be consistent with the standard deviation, so actually the cut-off is 1.4826*median absolute deviations from the median. In certain embodiments, this operation is applied to all chromosomes in the sample, including both the robust chromosomes and the chromosomes suspected of aneuploidy.

Figure 3K:
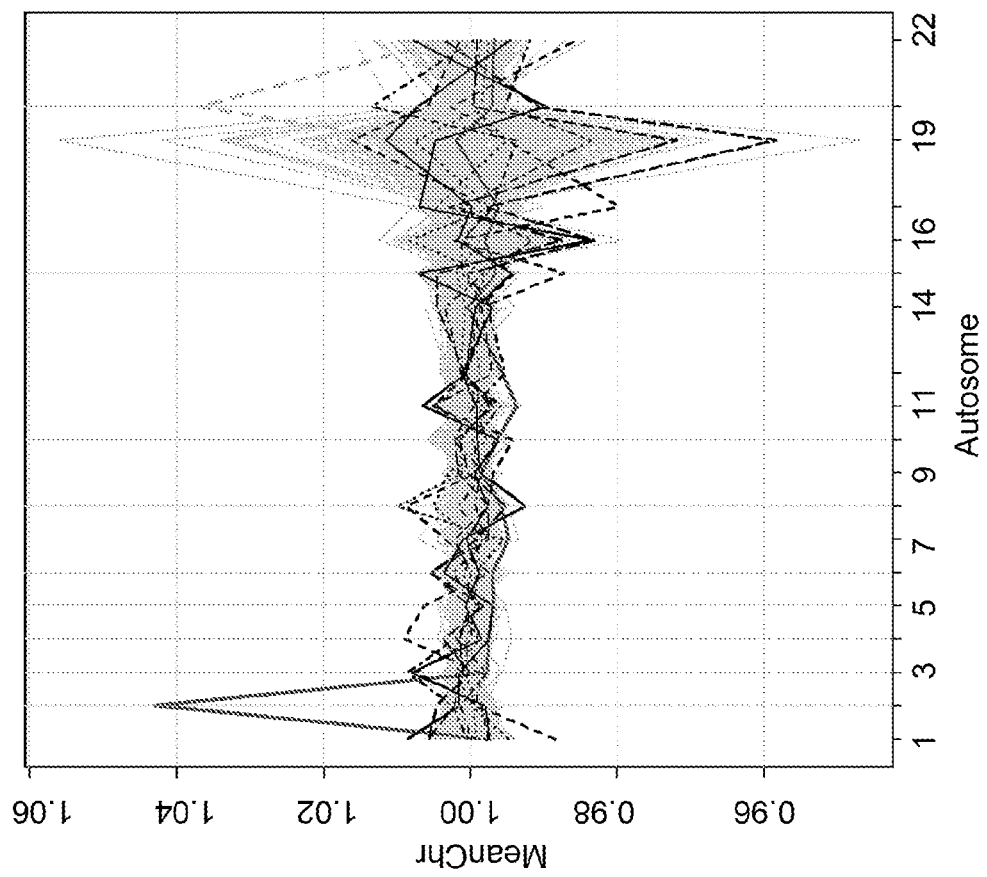
Figure 3K:
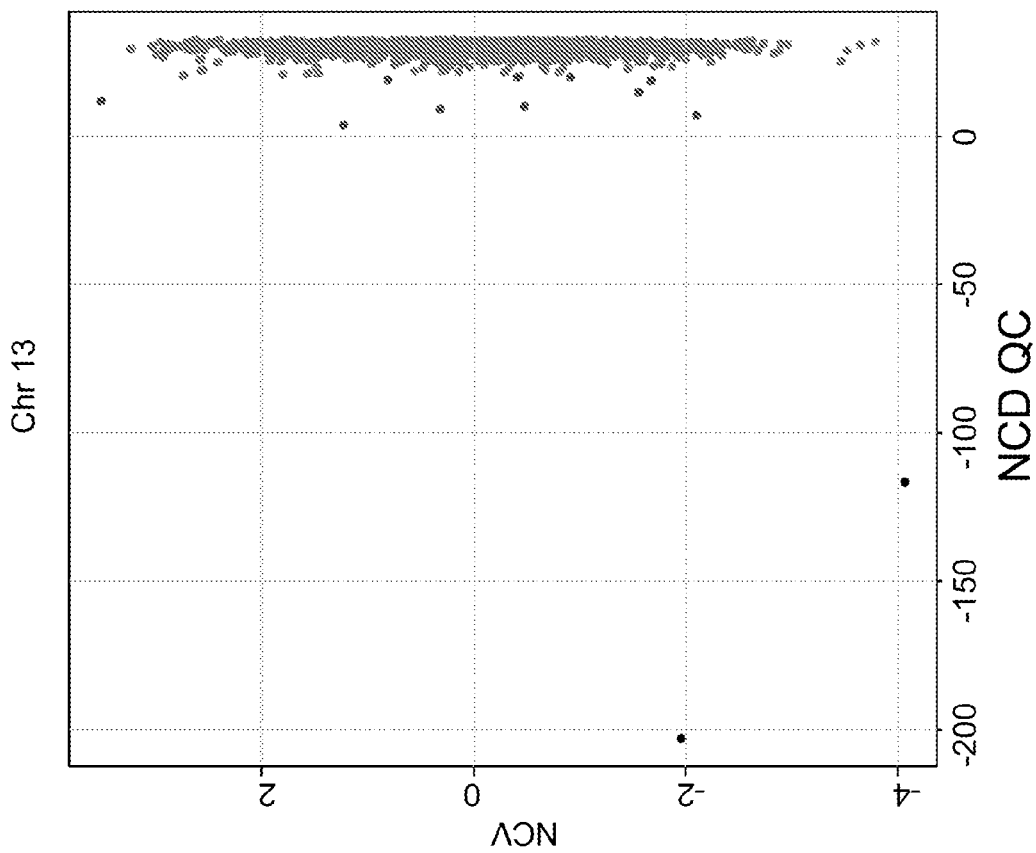

In certain implementations, an additional operation which may be characterized as quality control is performed. See block 323. In some embodiments, a quality control metric involves detection of whether any potential denominator chromosomes i.e. "normalizing chromosomes" or "robust chromosomes" are aneuploid or otherwise inappropriate for determining whether the test sample has a copy number variation in a sequence of interest. When the process determines that a robust chromosome is inappropriate, the process may disregard the test sample and make no call. Alternatively, a failure of this QC metric may trigger use of an alternate set of normalizing chromosomes for calling. In one example, a quality control method compares actual normalized coverage values for robust chromosomes against expectation values for robust autosomal chromosomes. The expectation values can be obtained by fitting a multivariate normal model to the normalized profiles of unaffected training samples, selecting the best model structure according to the likelihood of the data or Bayesian criteria (e.g., the model is selected using Akaike information criterion or possibly Bayesian information criterion), and fixing the best model for use in QC. The normal models of the robust chromosomes can be obtained by, for example, using a clustering technique that identifies a probability function having a mean and standard deviation for the chromosome coverages in the normal samples. Of course, other model forms may be used. The process evaluates the likelihood of observed normalized coverage in any incoming test sample given the fixed model parameters. It may do this by scoring each incoming test sample with the model to obtain likelihood and thereby identify outliers relative to normal sample set. Deviation in the likelihood of the test sample from that of the training samples may suggest either an abnormality in normalizing chromosomes or a sample handling/assay processing artifact that may result in incorrect sample classification. This QC metric can be used to reduce errors in classification associated with either of these sample artifacts. FIG. 3K, right panel, shows on the x-axis chromosome number and the y-axis shows normalized chromosome coverage based on a comparison with a QC model obtained as described above. The graphs shows one sample with an excessive coverage for chromosome 2 and other sample with an excessive coverage for chromosome 20. These samples would be eliminated using the QC metric described here or diverted to use an alternate set of normalizing chromosomes. The left panel of FIG. 3K shows NCV versus likelihood for a chromosome.

The sequence depicted in FIG. 3A may be used for all bins of all chromosomes in the genome. In certain embodiments, a different process is applied to chromosome Y. To calculate chromosome or segment dose, NCV, and/or NSV, the corrected normalized coverage quantities (as determined in FIG. 3A) from bins in the chromosomes or segments used in the expressions for dose, NCV, and/or NSV are used. See block 325. In certain embodiments, a mean normalized coverage quantity is calculated from all bins in a chromosome of interest, normalizing chromosome, segment of interest, and/or normalizing segment is used to calculate sequence dose, NCV, and/or NSV as described elsewhere herein.

In certain embodiments, chromosome Y is treated differently. It may be filtered by masking a set of bins unique to the Y chromosome. In some embodiments, the Y chromosome filter is determined according the process in U.S. Provisional Patent Application No. 61/836,057, previously incorporated by reference. In some embodiments, the filter masks bins that are smaller than those in the filter of the other chromosomes. For example, the Y chromosome mask may filter at the 1 kb level, while the other chromosome masks may filter at the 100 kb level. Nevertheless, the Y chromosome may be normalized at the same bin size as the other chromosomes (e.g., 100 kb).

In certain embodiments, the filtered Y chromosome is normalized as described above in operation 315 of FIG. 3A. However, otherwise, the Y chromosome is not further corrected. Thus, the Y chromosome bins are not subjected to global profile removal. Similarly, the Y chromosome bins are not subjected to GC correction or other filtering steps performed thereafter. This is because when the sample is processed, the process does not know whether the sample is male or female. A female sample should have no reads aligning to the Y reference chromosome.

Creating a Sequence Mask

Some embodiments disclosed herein employ a strategy for filtering out (or masking) non-discriminant sequence reads on a sequence of interest using sequence masks, which leads to higher signal and lower noise, relatively to values calculated by conventional methods, in the coverage values used for CNV evaluation. Such masks can be identified by various techniques. In one embodiment, a mask is identified using a technique illustrated in FIGS. 4A-4B as explained below in further details.

In some implementations, the mask is identified using a training set of representative samples known to have normal copy number of the sequence of interest. Masks may be identified using a technique that first normalizes the training set samples, then corrects for systematic variation across a range of sequence (e.g., a profile), and then corrects them for GC variability as described below. The normalization and correction are performed on samples from a training set, not test samples. The mask is identified once and then applied to many test samples.

Figure 4A:
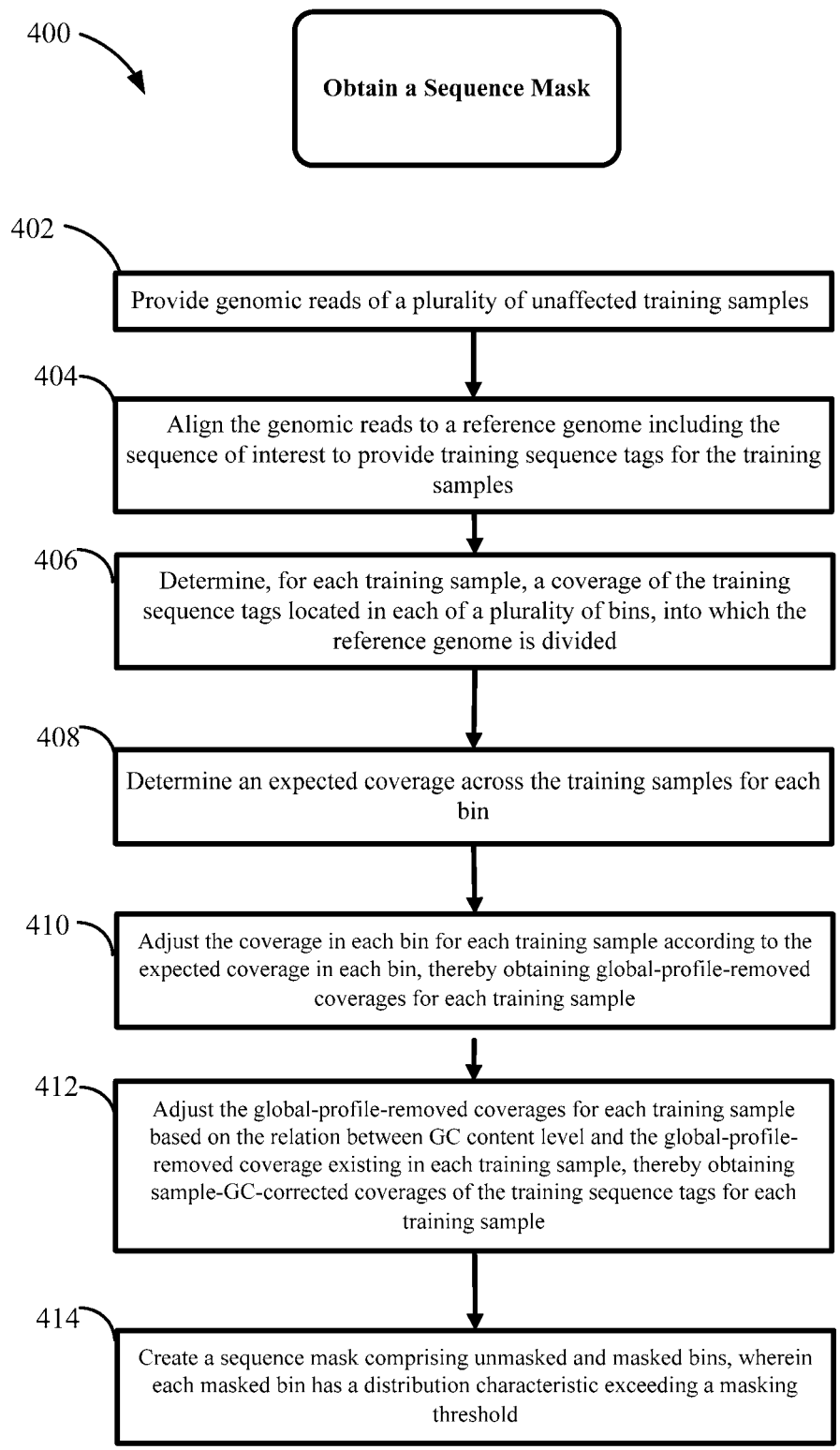
FIG. 4A shows a flow chart of a process for creating a sequence mask for reducing noise in sequence data.

FIG. 4A shows a flow chart of a process 400 for creating such a sequence mask, which can be applied to one or more test samples to remove bins on a sequence of interest from consideration in evaluation of copy number. The process starts by providing a training set including sequence reads from a plurality of unaffected training samples. Block 402. The process then align the sequence reads of the training set to a reference genome comprising the sequence of interest, thereby providing training sequence tags for the training samples. Block 404. In some embodiments, only uniquely aligned non-redundant tags mapped to non-excluded sites are used for further analysis. The process involves dividing the reference genome into a plurality of bins and determining for each unaffected training sample a coverage of training sequence tags in each bin for each training sample. Block 406. The process also determines for each bin an expected coverage of the training sequence tags across all training samples. Block 408. In some embodiments, the expected coverage of each bin is the median or means across the training samples. The expected coverages constitutes a global profile. The process then adjust the coverage of the training sequence tags in each bin for each training sample by removing the variation in the global profile, thereby obtaining global-profile-corrected coverages of the training sequence tags in the bins for each training sample. Block 410. The process optionally adjust the global-profile-corrected coverages for each training sample based on the relation between GC content level and the global-profile-corrected coverages for each training sample as described above, thereby obtaining sample-GC-corrected coverages of the training sequence tags for each training sample. Block 412. The process then creates a sequence mask comprising unmasked and masked bins across the reference genome. Block 414. Each masked bin has a distribution characteristic exceeding a masking threshold. The distribution characteristic is provided for the adjusted coverages of the training sequence tags in the bin across training samples. In some implementations, the masking threshold may relate to the observed variation in normalized coverage within a bin across training samples. Bins with high coefficients of variation or median absolute deviation of normalized coverage across samples may be identified based on an empirical distribution of the respective metrics. In some alternative implementations, the masking threshold may relate to the observed variation in normalized coverage within a bin across training samples. Bins with high coefficients of variation or median absolute deviation of normalized coverage across samples may be masked based on an empirical distribution of the respective metrics.

In some implementations, separate cut-offs for identifying masked bins, i.e., masking thresholds, are defined for the chromosome of interest and for all other chromosomes. Further, separate masking thresholds may be defined for each chromosome of interest separately, and a single masking threshold for the set of all non-affected chromosomes. As an example, a mask based on a certain masking threshold is defined for chromosome 13 and another masking threshold is used to define a mask for the other chromosomes. Non-affected chromosomes may also have their masking thresholds defined per chromosome.

Various masking threshold combinations may be evaluated for each chromosome of interest. The masking threshold combinations provide one mask for the bins of the chromosome of interest and a different mask for the bins of all other chromosomes.

In one approach, a range of values for coefficient of variation (CV) or measure of sample distribution cut-offs is defined as percentiles (e.g., 95, 96, 97, 98, 99) of the empirical distribution of bin CV values and these cut-off values are applied to all autosomes excluding chromosomes of interest. Further, a range of percentile cut-off values for CV is defined for the empirical CV distribution and these cut-off values are applied to a chromosome of interest (e.g., chr 21). In some embodiments, the chromosomes of interest are the X chromosome and chromosomes 13, 18, and 21. Of course, other approaches may be considered; for example, a separate optimization may be performed for each chromosome. Together, the ranges to be optimized in parallel (e.g., one range for a chromosome of interest under consideration and another range for all other chromosomes) define a grid of CV cut-off combinations. See FIG. 4B. Performance of the system on the training set is evaluated across the two cut-offs (one for normalizing chromosomes (or autosomes other than the chromosome of interest) and one for chromosome of interest), and the best performing combination is chosen for final configuration. This combination may be different for each of the chromosomes of interest. In certain embodiments, performance is evaluated on a validation set instead of the training set, namely, cross-validation is used to evaluate performance.

In some embodiments, the performance optimized to determine cut-off ranges is the coefficient of variation of chromosome doses (based on a tentative selection of normalizing chromosomes). The process selects the combination of cut-offs that minimize the CV of the chromosome dose (e.g., ratio) of the chromosome of interest using a currently a selected normalizing chromosome (or chromosomes). In one approach, the process tests the performance of each combination of cut-offs in the grid as follows: (1) apply the combination of cut-offs to define masks for all chromosomes and apply those masks to filter the tags of a training set; (2) calculate normalized coverages across the training set of unaffected samples by applying the process of FIG. 3A to the filtered tags; (3) determine a representative normalized coverage per chromosome by, e.g., summing the bin's normalized coverages for a chromosome under consideration; (4) calculate chromosome doses using the current normalizing chromosomes, and (5) determine the CVs of the chromosome doses. The process may assess the performance of the selected filters by applying them to a set of test samples separated from an original portion of the training set. That is, the process splits the original training set into training and testing subsets. The training subset is used to define the mask cut-offs as described above.

Figure 4B:
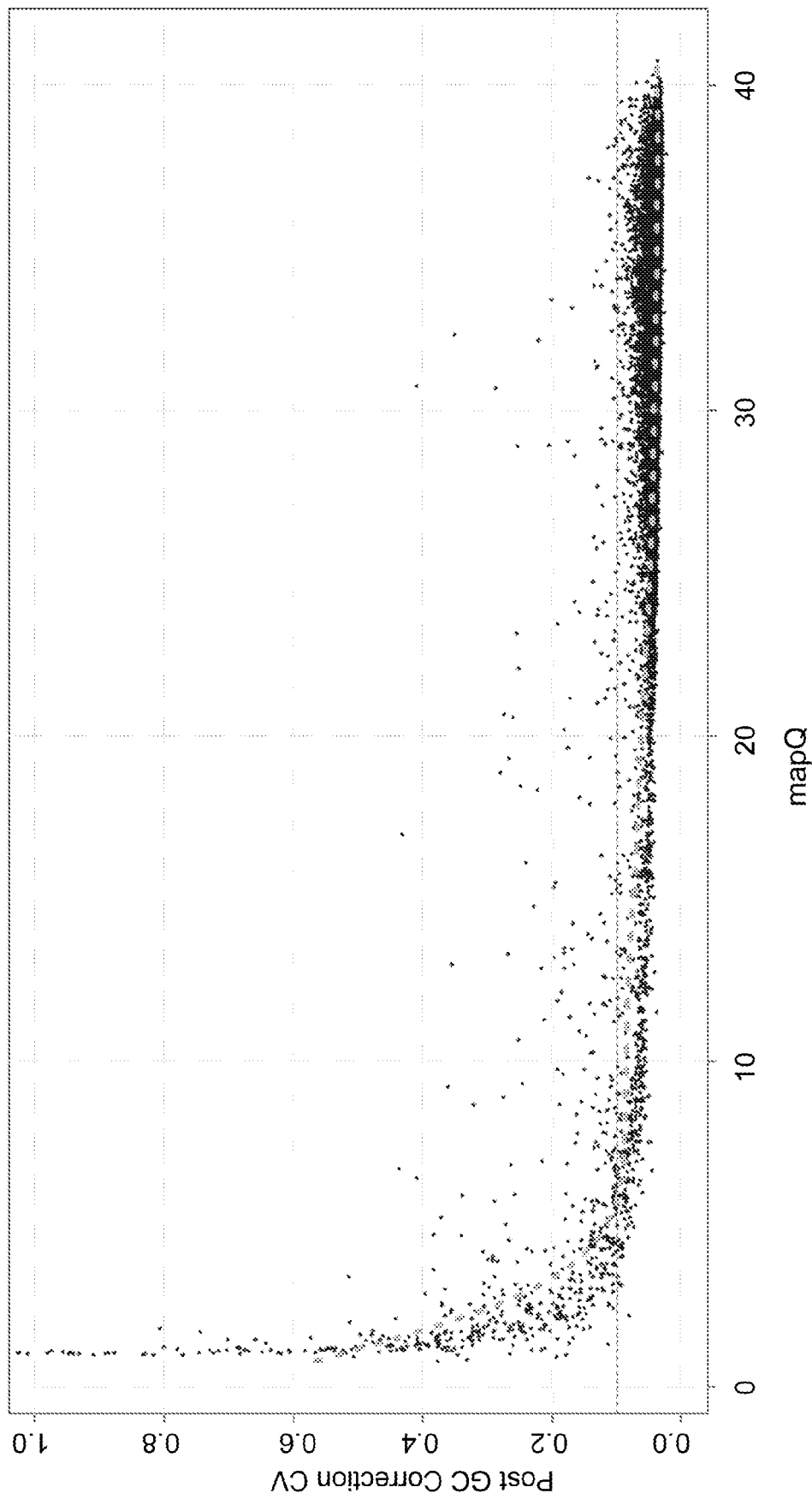
FIG. 4B shows that MapQ score has a strong monotonous correlation with CV of normalized coverage quantities.

In alternative embodiments, instead of defining masks based on CV of coverages, the masks may be defined by a distribution of mapping quality scores from the alignment results across training samples within the bins. A mapping quality score reflects the uniqueness with which a read is mapped to the reference genome. In other words, mapping quality scores quantify the probability that a read is misaligned. A low mapping quality score is associated low uniqueness (high probability of misalignment). The uniqueness accounts for one or more errors in the read sequence (as generated by the sequencer). A detailed description of mapping quality scores is presented in Li H, Ruan J, Durbin R. (2008) Mapping short DNA sequencing reads and calling variants using mapping quality scores. *Genome Research* 18:1851-8, which is incorporated herein by reference in its entirety. In some implementation, the mapping quality score herein is referred to as a MapQ score. FIG. 4B shows that MapQ score has a strong monotonous correlation with CV of processed coverages. For instance, bins with CV higher than 0.4 almost completely cluster on the left of the plot in FIG. 4B, having MapQ scores lower than about 4. Therefore, masking bins with small MapQ can yield a mask quite similar to one defined by masking bins with high CV.

Samples and Sample Processing

Samples

Samples that are used for determining a CNV, e.g., chromosomal aneuploidies, partial aneuploidies, and the like, can include samples taken from any cell, tissue, or organ in which copy number variations for one or more sequences of interest are to be determined. Desirably, the samples contain nucleic acids that are that are present in cells and/or nucleic acids that are "cell-free" (e.g., cfDNA).

In some embodiments it is advantageous to obtain cell-free nucleic acids, e.g., cell-free DNA (cfDNA). Cell-free nucleic acids, including cell-free DNA, can be obtained by various methods known in the art from biological samples including but not limited to plasma, serum, and urine (see, e.g., Fan et al., Proc Natl Acad Sci 105:16266-16271 [2008]; Koide et al., Prenatal Diagnosis 25:604-607 [2005]; Chen et al., Nature Med. 2: 1033-1035 [1996]; Lo et al., Lancet 350: 485-487 [1997]; Botezatu et al., Clin Chem. 46: 1078-1084, 2000; and Su et al., J Mol. Diagn. 6: 101-107 [2004]). To separate cell-free DNA from cells in a sample, various methods including, but not limited to fractionation, centrifugation (e.g., density gradient centrifugation), DNA-specific precipitation, or high-throughput cell sorting and/or other separation methods can be used. Commercially available kits for manual and automated separation of cfDNA are available (Roche Diagnostics, Indianapolis, Ind., Qiagen, Valencia, Calif., Macherey-Nagel, Duren, Del.). Biological samples comprising cfDNA have been used in assays to determine the presence or absence of chromosomal abnormalities, e.g., trisomy 21, by sequencing assays that can detect chromosomal aneuploidies and/or various polymorphisms.

In various embodiments the cfDNA present in the sample can be enriched specifically or non-specifically prior to use (e.g., prior to preparing a sequencing library). Non-specific enrichment of sample DNA refers to the whole genome amplification of the genomic DNA fragments of the sample that can be used to increase the level of the sample DNA prior to preparing a cfDNA sequencing library. Non-specific enrichment can be the selective enrichment of one of the two genomes present in a sample that comprises more than one genome. For example, non-specific enrichment can be selective of the fetal genome in a maternal sample, which can be obtained by known methods to increase the relative proportion of fetal to maternal DNA in a sample. Alternatively, non-specific enrichment can be the non-selective amplification of both genomes present in the sample. For example, non-specific amplification can be of fetal and maternal DNA in a sample comprising a mixture of DNA from the fetal and maternal genomes. Methods for whole genome amplification are known in the art. Degenerate oligonucleotide-primed PCR (DOP), primer extension PCR technique (PEP) and multiple displacement amplification (MDA) are examples of whole genome amplification methods. In some embodiments, the sample comprising the mixture of cfDNA from different genomes is un-enriched for cfDNA of the genomes present in the mixture. In other embodiments, the sample comprising the mixture of cfDNA from different genomes is non-specifically enriched for any one of the genomes present in the sample.

The sample comprising the nucleic acid(s) to which the methods described herein are applied typically comprises a biological sample ("test sample"), e.g., as described above. In some embodiments, the nucleic acid(s) to be screened for one or more CNVs is purified or isolated by any of a number of well-known methods.

Accordingly, in certain embodiments the sample comprises or consists of a purified or isolated polynucleotide, or it can comprise samples such as a tissue sample, a biological fluid sample, a cell sample, and the like. Suitable biological fluid samples include, but are not limited to blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, amniotic fluid, milk, and leukophoresis samples. In some embodiments, the sample is a sample that is easily obtainable by non-invasive procedures, e.g., blood, plasma, serum, sweat, tears, sputum, urine, sputum, ear flow, saliva or feces. In certain embodiments the sample is a peripheral blood sample, or the plasma and/or serum fractions of a peripheral blood sample. In other embodiments, the biological sample is a swab or smear, a biopsy specimen, or a cell culture. In another embodiment, the sample is a mixture of two or more biological samples, e.g., a biological sample can comprise two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments, samples can be obtained from sources, including, but not limited to, samples from different individuals, samples from different developmental stages of the same or different individuals, samples from different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, samples from individuals with predisposition to a pathology, samples individuals with exposure to an infectious disease agent (e.g., HIV), and the like.

In one illustrative, but non-limiting embodiment, the sample is a maternal sample that is obtained from a pregnant female, for example a pregnant woman. In this instance, the sample can be analyzed using the methods described herein to provide a prenatal diagnosis of potential chromosomal abnormalities in the fetus. The maternal sample can be a tissue sample, a biological fluid sample, or a cell sample. A biological fluid includes, as non-limiting examples, blood, plasma, serum, sweat, tears, sputum, urine, sputum, ear flow, lymph, saliva, cerebrospinal fluid, ravages, bone marrow suspension, vaginal flow, transcervical lavage, brain fluid, ascites, milk, secretions of the respiratory, intestinal and genitourinary tracts, and leukophoresis samples.

In another illustrative, but non-limiting embodiment, the maternal sample is a mixture of two or more biological samples, e.g., the biological sample can comprise two or more of a biological fluid sample, a tissue sample, and a cell culture sample. In some embodiments, the sample is a sample that is easily obtainable by non-invasive procedures, e.g., blood, plasma, serum, sweat, tears, sputum, urine, milk, sputum, ear flow, saliva and feces. In some embodiments, the biological sample is a peripheral blood sample, and/or the plasma and serum fractions thereof. In other embodiments, the biological sample is a swab or smear, a biopsy specimen, or a sample of a cell culture. As disclosed above, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In certain embodiments samples can also be obtained from in vitro cultured tissues, cells, or other polynucleotide-containing sources. The cultured samples can be taken from sources including, but not limited to, cultures (e.g., tissue or cells) maintained in different media and conditions (e.g., pH, pressure, or temperature), cultures (e.g., tissue or cells) maintained for different periods of length, cultures (e.g., tissue or cells) treated with different factors or reagents (e.g., a drug candidate, or a modulator), or cultures of different types of tissue and/or cells.

Methods of isolating nucleic acids from biological sources are well known and will differ depending upon the nature of the source. One of skill in the art can readily isolate nucleic acid(s) from a source as needed for the method described herein. In some instances, it can be advantageous to fragment the nucleic acid molecules in the nucleic acid sample. Fragmentation can be random, or it can be specific, as achieved, for example, using restriction endonuclease digestion. Methods for random fragmentation are well known in the art, and include, for example, limited DNAse digestion, alkali treatment and physical shearing. In one embodiment, sample nucleic acids are obtained from as cfDNA, which is not subjected to fragmentation.

In other illustrative embodiments, the sample nucleic acid(s) are obtained as genomic DNA, which is subjected to fragmentation into fragments of approximately 300 or more, approximately 400 or more, or approximately 500 or more base pairs, and to which NGS methods can be readily applied.

Sequencing Library Preparation

In one embodiment, the methods described herein can utilize next generation sequencing technologies (NGS), that allow multiple samples to be sequenced individually as genomic molecules (i.e., singleplex sequencing) or as pooled samples comprising indexed genomic molecules (e.g., multiplex sequencing) on a single sequencing run. These methods can generate up to several hundred million reads of DNA sequences. In various embodiments the sequences of genomic nucleic acids, and/or of indexed genomic nucleic acids can be determined using, for example, the Next Generation Sequencing Technologies (NGS) described herein. In various embodiments analysis of the massive amount of sequence data obtained using NGS can be performed using one or more processors as described herein.

In various embodiments the use of such sequencing technologies does not involve the preparation of sequencing libraries.

However, in certain embodiments the sequencing methods contemplated herein involve the preparation of sequencing libraries. In one illustrative approach, sequencing library preparation involves the production of a random collection of adapter-modified DNA fragments (e.g., polynucleotides) that are ready to be sequenced. Sequencing libraries of polynucleotides can be prepared from DNA or RNA, including equivalents, analogs of either DNA or cDNA, for example, DNA or cDNA that is complementary or copy DNA produced from an RNA template, by the action of reverse transcriptase. The polynucleotides may originate in double-stranded form (e.g., dsDNA such as genomic DNA fragments, cDNA, PCR amplification products, and the like) or, in certain embodiments, the polynucleotides may originated in single-stranded form (e.g., ssDNA, RNA, etc.) and have been converted to dsDNA form. By way of illustration, in certain embodiments, single stranded mRNA molecules may be copied into double-stranded cDNAs suitable for use in preparing a sequencing library. The precise sequence of the primary polynucleotide molecules is generally not material to the method of library preparation, and may be known or unknown. In one embodiment, the polynucleotide molecules are DNA molecules. More particularly, in certain embodiments, the polynucleotide molecules represent the entire genetic complement of an organism or substantially the entire genetic complement of an organism, and are genomic DNA molecules (e.g., cellular DNA, cell free DNA (cfDNA), etc.), that typically include both intron sequence and exon sequence (coding sequence), as well as non-coding regulatory sequences such as promoter and enhancer sequences. In certain embodiments, the primary polynucleotide molecules comprise human genomic DNA molecules, e.g., cfDNA molecules present in peripheral blood of a pregnant subject.

Preparation of sequencing libraries for some NGS sequencing platforms is facilitated by the use of polynucleotides comprising a specific range of fragment sizes. Preparation of such libraries typically involves the fragmentation of large polynucleotides (e.g. cellular genomic DNA) to obtain polynucleotides in the desired size range.

Fragmentation can be achieved by any of a number of methods known to those of skill in the art. For example, fragmentation can be achieved by mechanical means including, but not limited to nebulization, sonication and hydroshear. However mechanical fragmentation typically cleaves the DNA backbone at C—O, P—O and C—C bonds resulting in a heterogeneous mix of blunt and 3'- and 5'-overhanging ends with broken C—O, P—O and/C—C bonds (see, e.g., Alnemri and Liwack, J Biol. Chem 265:17323-17333 [1990]; Richards and Boyer, J Mol Biol 11:327-240 [1965]) which may need to be repaired as they may lack the requisite 5'-phosphate for the subsequent enzymatic reactions, e.g., ligation of sequencing adaptors, that are required for preparing DNA for sequencing.

In contrast, cfDNA, typically exists as fragments of less than about 300 base pairs and consequently, fragmentation is not typically necessary for generating a sequencing library using cfDNA samples.

Typically, whether polynucleotides are forcibly fragmented (e.g., fragmented in vitro), or naturally exist as fragments, they are converted to blunt-ended DNA having 5'-phosphates and 3'-hydroxyl. Standard protocols, e.g., protocols for sequencing using, for example, the Illumina platform as described elsewhere herein, instruct users to end-repair sample DNA, to purify the end-repaired products prior to dA-tailing, and to purify the dA-tailing products prior to the adaptor-ligating steps of the library preparation.

Various embodiments of methods of sequence library preparation described herein obviate the need to perform one or more of the steps typically mandated by standard protocols to obtain a modified DNA product that can be sequenced by NGS. An abbreviated method (ABB method), a 1-step method, and a 2-step method are examples of methods for preparation of a sequencing library, which can be found in patent application Ser. No. 13/555,037 filed on Jul. 20, 2012, which is incorporated by reference by its entirety.

Marker Nucleic Acids for Tracking and Verifying Sample Integrity

In various embodiments verification of the integrity of the samples and sample tracking can be accomplished by sequencing mixtures of sample genomic nucleic acids, e.g., cfDNA, and accompanying marker nucleic acids that have been introduced into the samples, e.g., prior to processing.

Marker nucleic acids can be combined with the test sample (e.g., biological source sample) and subjected to processes that include, for example, one or more of the steps of fractionating the biological source sample, e.g., obtaining an essentially cell-free plasma fraction from a whole blood sample, purifying nucleic acids from a fractionated, e.g., plasma, or unfractionated biological source sample, e.g., a tissue sample, and sequencing. In some embodiments, sequencing comprises preparing a sequencing library. The sequence or combination of sequences of the marker molecules that are combined with a source sample is chosen to be unique to the source sample. In some embodiments, the unique marker molecules in a sample all have the same sequence. In other embodiments, the unique marker molecules in a sample are a plurality of sequences, e.g., a combination of two, three, four, five, six, seven, eight, nine, ten, fifteen, twenty, or more different sequences.

In one embodiment, the integrity of a sample can be verified using a plurality of marker nucleic acid molecules having identical sequences. Alternatively, the identity of a sample can be verified using a plurality of marker nucleic acid molecules that have at least two, at least three, at least four, at least five, at least six, at least seven, at least eight, at least nine, at least ten, at least 11, at least 12, at least 13, at least 14, at least 15, at least 16, at least 17 m, at least 18, at least 19, at least 20, at least 25, at least 30, at least 35, at least 40, at least 50, or more different sequences. Verification of the integrity of the plurality of biological samples, i.e., two or more biological samples, requires that each of the two or more samples be marked with marker nucleic acids that have sequences that are unique to each of the plurality of test sample that is being marked. For example, a first sample can be marked with a marker nucleic acid having sequence A, and a second sample can be marked with a marker nucleic acid having sequence B. Alternatively, a first sample can be marked with marker nucleic acid molecules all having sequence A, and a second sample can be marked with a mixture of sequences B and C, wherein sequences A, B and C are marker molecules having different sequences.

The marker nucleic acid(s) can be added to the sample at any stage of sample preparation that occurs prior to library preparation (if libraries are to be prepared) and sequencing. In one embodiment, marker molecules can be combined with an unprocessed source sample. For example, the marker nucleic acid can be provided in a collection tube that is used to collect a blood sample. Alternatively, the marker nucleic acids can be added to the blood sample following the blood draw. In one embodiment, the marker nucleic acid is added to the vessel that is used to collect a biological fluid sample, e.g., the marker nucleic acid(s) are added to a blood collection tube that is used to collect a blood sample. In another embodiment, the marker nucleic acid(s) are added to a fraction of the biological fluid sample. For example, the marker nucleic acid is added to the plasma and/or serum fraction of a blood sample, e.g., a maternal plasma sample. In yet another embodiment, the marker molecules are added to a purified sample, e.g., a sample of nucleic acids that have been purified from a biological sample. For example, the marker nucleic acid is added to a sample of purified maternal and fetal cfDNA. Similarly, the marker nucleic acids can be added to a biopsy specimen prior to processing the specimen. In some embodiments, the marker nucleic acids can be combined with a carrier that delivers the marker molecules into the cells of the biological sample. Cell-delivery carriers include pH-sensitive and cationic liposomes.

In various embodiments, the marker molecules have antigenomic sequences, that are sequences that are absent from the genome of the biological source sample. In an exemplary embodiment, the marker molecules that are used to verify the integrity of a human biological source sample have sequences that are absent from the human genome. In an alternative embodiment, the marker molecules have sequences that are absent from the source sample and from any one or more other known genomes. For example, the marker molecules that are used to verify the integrity of a human biological source sample have sequences that are absent from the human genome and from the mouse genome. The alternative allows for verifying the integrity of a test sample that comprises two or more genomes. For example, the integrity of a human cell-free DNA sample obtained from a subject affected by a pathogen, e.g., a bacterium, can be verified using marker molecules having sequences that are absent from both the human genome and the genome of the affecting bacterium. Sequences of genomes of numerous pathogens, e.g., bacteria, viruses, yeasts, fungi, protozoa etc., are publicly available on the World Wide Web at ncbi.nlm.nih.gov/genomes. In another embodiment, marker molecules are nucleic acids that have sequences that are absent from any known genome. The sequences of marker molecules can be randomly generated algorithmically.

In various embodiments the marker molecules can be naturally-occurring deoxyribonucleic acids (DNA), ribonucleic acids or artificial nucleic acid analogs (nucleic acid mimics) including peptide nucleic acids (PNA), morpholino nucleic acid, locked nucleic acids, glycol nucleic acids, and threose nucleic acids, which are distinguished from naturally-occurring DNA or RNA by changes to the backbone of the molecule or DNA mimics that do not have a phosphodiester backbone. The deoxyribonucleic acids can be from naturally-occurring genomes or can be generated in a laboratory through the use of enzymes or by solid phase chemical synthesis. Chemical methods can also be used to generate the DNA mimics that are not found in nature. Derivatives of DNA are that are available in which the phosphodiester linkage has been replaced but in which the deoxyribose is retained include but are not limited to DNA mimics having backbones formed by thioformacetal or a carboxamide linkage, which have been shown to be good structural DNA mimics. Other DNA mimics include morpholino derivatives and the peptide nucleic acids (PNA), which contain an N-(2-aminoethyl)glycine-based pseudopeptide backbone (Ann Rev Biophys Biomol Struct 24:167-183 [1995]). PNA is an extremely good structural mimic of DNA (or of ribonucleic acid [RNA]), and PNA oligomers are able to form very stable duplex structures with Watson-Crick complementary DNA and RNA (or PNA) oligomers, and they can also bind to targets in duplex DNA by helix invasion (Mol Biotechnol 26:233-248 [2004]. Another good structural mimic/analog of DNA analog that can be used as a marker molecule is phosphorothioate DNA in which one of the non-bridging oxygens is replaced by a sulfur. This modification reduces the action of endo- and exonucleases2 including 5' to 3' and 3' to 5' DNA POL 1 exonuclease, nucleases S1 and P1, RNases, serum nucleases and snake venom phosphodiesterase.

The length of the marker molecules can be distinct or indistinct from that of the sample nucleic acids, i.e., the length of the marker molecules can be similar to that of the sample genomic molecules, or it can be greater or smaller than that of the sample genomic molecules. The length of the marker molecules is measured by the number of nucleotide or nucleotide analog bases that constitute the marker molecule. Marker molecules having lengths that differ from those of the sample genomic molecules can be distinguished from source nucleic acids using separation methods known in the art. For example, differences in the length of the marker and sample nucleic acid molecules can be determined by electrophoretic separation, e.g., capillary electrophoresis. Size differentiation can be advantageous for quantifying and assessing the quality of the marker and sample nucleic acids. Preferably, the marker nucleic acids are shorter than the genomic nucleic acids, and of sufficient length to exclude them from being mapped to the genome of the sample. For example, as a 30 base human sequence is needed to uniquely map it to a human genome. Accordingly in certain embodiments, marker molecules used in sequencing bioassays of human samples should be at least 30 bp in length.

The choice of length of the marker molecule is determined primarily by the sequencing technology that is used to verify the integrity of a source sample. The length of the sample genomic nucleic acids being sequenced can also be considered. For example, some sequencing technologies employ clonal amplification of polynucleotides, which can require that the genomic polynucleotides that are to be clonally amplified be of a minimum length. For example, sequencing using the Illumina GAII sequence analyzer includes an in vitro clonal amplification by bridge PCR (also known as cluster amplification) of polynucleotides that have a minimum length of 110 bp, to which adaptors are ligated to provide a nucleic acid of at least 200 bp and less than 600 bp that can be clonally amplified and sequenced. In some embodiments, the length of the adaptor-ligated marker molecule is between about 200 bp and about 600 bp, between about 250 bp and 550 bp, between about 300 bp and 500 bp, or between about 350 and 450. In other embodiments, the length of the adaptor-ligated marker molecule is about 200 bp. For example, when sequencing fetal cfDNA that is present in a maternal sample, the length of the marker molecule can be chosen to be similar to that of fetal cfDNA molecules. Thus, in one embodiment, the length of the marker molecule used in an assay that comprises massively parallel sequencing of cfDNA in a maternal sample to determine the presence or absence of a fetal chromosomal aneuploidy, can be about 150 bp, about 160 bp, 170 bp, about 180 bp, about 190 bp or about 200 bp; preferably, the marker molecule is about 170 pp. Other sequencing approaches, e.g., SOLiD sequencing, Polony Sequencing and 454 sequencing use emulsion PCR to clonally amplify DNA molecules for sequencing, and each technology dictates the minimum and the maximum length of the molecules that are to be amplified. The length of marker molecules to be sequenced as clonally amplified nucleic acids can be up to about 600 bp. In some embodiments, the length of marker molecules to be sequenced can be greater than 600 bp.

Single molecule sequencing technologies, that do not employ clonal amplification of molecules, and are capable of sequencing nucleic acids over a very broad range of template lengths, in most situations do not require that the molecules to be sequenced be of any specific length. However, the yield of sequences per unit mass is dependent on the number of 3' end hydroxyl groups, and thus having relatively short templates for sequencing is more efficient than having long templates. If starting with nucleic acids longer than 1000 nt, it is generally advisable to shear the nucleic acids to an average length of 100 to 200 nt so that more sequence information can be generated from the same mass of nucleic acids. Thus, the length of the marker molecule can range from tens of bases to thousands of bases. The length of marker molecules used for single molecule sequencing can be up to about 25 bp, up to about 50 bp, up to about 75 bp, up to about 100 bp, up to about 200 bp, up to about 300 bp, up to about 400 bp, up to about 500 bp, up to about 600 bp, up to about 700 bp, up to about 800 bp, up to about 900 bp, up to about 1000 bp, or more in length.

The length chosen for a marker molecule is also determined by the length of the genomic nucleic acid that is being sequenced. For example, cfDNA circulates in the human bloodstream as genomic fragments of cellular genomic DNA. Fetal cfDNA molecules found in the plasma of pregnant women are generally shorter than maternal cfDNA molecules (Chan et al., Clin Chem 50:8892 [2004]). Size fractionation of circulating fetal DNA has confirmed that the average length of circulating fetal DNA fragments is <300 bp, while maternal DNA has been estimated to be between about 0.5 and 1 Kb (Li et al., Clin Chem, 50: 1002-1011 [2004]). These findings are consistent with those of Fan et al., who determined using NGS that fetal cfDNA is rarely >340 bp (Fan et al., Clin Chem 56:1279-1286 [2010]). DNA isolated from urine with a standard silica-based method consists of two fractions, high molecular weight DNA, which originates from shed cells and low molecular weight (150-250 base pair) fraction of transrenal DNA (Tr-DNA) (Botezatu et al., Clin Chem. 46: 1078-1084, 2000; and Su et al., J Mol. Diagn. 6: 101-107, 2004). The application of newly developed technique for isolation of cell-free nucleic acids from body fluids to the isolation of transrenal nucleic acids has revealed the presence in urine of DNA and RNA fragments much shorter than 150 base pairs (U.S. Patent Application Publication No. 20080139801). In embodiments, wherein cfDNA is the genomic nucleic acid that is sequenced, marker molecules that are chosen can be up to about the length of the cfDNA. For example, the length of marker molecules used in maternal cfDNA samples to be sequenced as single nucleic acid molecules or as clonally amplified nucleic acids can be between about 100 bp and 600. In other embodiments, the sample genomic nucleic acids are fragments of larger molecules. For example, a sample genomic nucleic acid that is sequenced is fragmented cellular DNA. In embodiments, when fragmented cellular DNA is sequenced, the length of the marker molecules can be up to the length of the DNA fragments. In some embodiments, the length of the marker molecules is at least the minimum length required for mapping the sequence read uniquely to the appropriate reference genome. In other embodiments, the length of the marker molecule is the minimum length that is required to exclude the marker molecule from being mapped to the sample reference genome.

In addition, marker molecules can be used to verify samples that are not assayed by nucleic acid sequencing, and that can be verified by common bio-techniques other than sequencing, e.g., real-time PCR.

Sample Controls (e.g., in Process Positive Controls for Sequencing and/or Analysis).

In various embodiments marker sequences introduced into the samples, e.g., as described above, can function as positive controls to verify the accuracy and efficacy of sequencing and subsequent processing and analysis.

Accordingly, compositions and method for providing an in-process positive control (IPC) for sequencing DNA in a sample are provided. In certain embodiments, positive controls are provided for sequencing cfDNA in a sample comprising a mixture of genomes are provided. An IPC can be used to relate baseline shifts in sequence information obtained from different sets of samples, e.g., samples that are sequenced at different times on different sequencing runs. Thus, for example, an IPC can relate the sequence information obtained for a maternal test sample to the sequence information obtained from a set of qualified samples that were sequenced at a different time.

Similarly, in the case of segment analysis, an IPC can relate the sequence information obtained from a subject for particular segment(s) to the sequence obtained from a set of qualified samples (of similar sequences) that were sequenced at a different time. In certain embodiments an IPC can relate the sequence information obtained from a subject for particular cancer-related loci to the sequence information obtained from a set of qualified samples (e.g., from a known amplification/deletion, and the like).

In addition, IPCs can be used as markers to track sample (s) through the sequencing process. IPCs can also provide a qualitative positive sequence dose value, e.g., NCV, for one or more aneuploidies of chromosomes of interest, e.g., trisomy 21, trisomy 13, trisomy 18 to provide proper interpretation, and to ensure the dependability and accuracy of the data. In certain embodiments IPCs can be created to comprise nucleic acids from male and female genomes to provide doses for chromosomes X and Y in a maternal sample to determine whether the fetus is male.

The type and the number of in-process controls depends on the type or nature of the test needed. For example, for a test requiring the sequencing of DNA from a sample comprising a mixture of genomes to determine whether a chromosomal aneuploidy exists, the in-process control can comprise DNA obtained from a sample known comprising the same chromosomal aneuploidy that is being tested. In some embodiments, the IPC includes DNA from a sample known to comprise an aneuploidy of a chromosome of interest. For example, the IPC for a test to determine the presence or absence of a fetal trisomy, e.g., trisomy 21, in a maternal sample comprises DNA obtained from an individual with trisomy 21. In some embodiments, the IPC comprises a mixture of DNA obtained from two or more individuals with different aneuploidies. For example, for a test to determine the presence or absence of trisomy 13, trisomy 18, trisomy 21, and monosomy X, the IPC comprises a combination of DNA samples obtained from pregnant women each carrying a fetus with one of the trisomies being tested. In addition to complete chromosomal aneuploidies, IPCs can be created to provide positive controls for tests to determine the presence or absence of partial aneuploidies.

An IPC that serves as the control for detecting a single aneuploidy can be created using a mixture of cellular genomic DNA obtained from a two subjects one being the contributor of the aneuploid genome. For example, an IPC that is created as a control for a test to determine a fetal trisomy, e.g., trisomy 21, can be created by combining genomic DNA from a male or female subject carrying the trisomic chromosome with genomic DNA with a female subject known not to carry the trisomic chromosome. Genomic DNA can be extracted from cells of both subjects, and sheared to provide fragments of between about 100-400 bp, between about 150-350 bp, or between about 200-300 bp to simulate the circulating cfDNA fragments in maternal samples. The proportion of fragmented DNA from the subject carrying the aneuploidy, e.g., trisomy 21, is chosen to simulate the proportion of circulating fetal cfDNA found in maternal samples to provide an IPC comprising a mixture of fragmented DNA comprising about 5%, about 10%, about 15%, about 20%, about 25%, about 30%, of DNA from the subject carrying the aneuploidy. The IPC can comprise DNA from different subjects each carrying a different aneuploidy. For example, the IPC can comprise about 80% of the unaffected female DNA, and the remaining 20% can be DNA from three different subjects each carrying a trisomic chromosome 21, a trisomic chromosome 13, and a trisomic chromosome 18. The mixture of fragmented DNA is prepared for sequencing. Processing of the mixture of fragmented DNA can comprise preparing a sequencing library, which can be sequenced using any massively parallel methods in singleplex or multiplex fashion. Stock solutions of the genomic IPC can be stored and used in multiple diagnostic tests.

Alternatively the IPC can be created using cfDNA obtained from a mother known to carry a fetus with a known chromosomal aneuploidy. For example, cfDNA can be obtained from a pregnant woman carrying a fetus with trisomy 21. The cfDNA is extracted from the maternal sample, and cloned into a bacterial vector and grown in bacteria to provide an ongoing source of the IPC. The DNA can be extracted from the bacterial vector using restriction enzymes. Alternatively, the cloned cfDNA can be amplified by, e.g., PCR. The IPC DNA can be processed for sequencing in the same runs as the cfDNA from the test samples that are to be analyzed for the presence or absence of chromosomal aneuploidies.

While the creation of IPCs is described above with respect to trisomies, it will be appreciated that IPCs can be created to reflect other partial aneuploidies including for example, various segment amplification and/or deletions. Thus, for example, where various cancers are known to be associated with particular amplifications (e.g., breast cancer associated with 20Q13) IPCs can be created that incorporate those known amplifications.
Sequencing Methods As indicated above, the prepared samples (e.g., Sequencing Libraries) are sequenced as part of the procedure for identifying copy number variation(s). Any of a number of sequencing technologies can be utilized.

Some sequencing technologies are available commercially, such as the sequencing-by-hybridization platform from Affymetrix Inc. (Sunnyvale, Calif.) and the sequencing-by-synthesis platforms from 454 Life Sciences (Bradford, Conn.), Illumina/Solexa (Hayward, Calif.) and Helicos Biosciences (Cambridge, Mass.), and the sequencing-by-ligation platform from Applied Biosystems (Foster City, Calif.), as described below. In addition to the single molecule sequencing performed using sequencing-by-synthesis of Helicos Biosciences, other single molecule sequencing technologies include, but are not limited to, the SMRT™ technology of Pacific Biosciences, the ION TORRENT™ technology, and nanopore sequencing developed for example, by Oxford Nanopore Technologies.

While the automated Sanger method is considered as a 'first generation' technology, Sanger sequencing including the automated Sanger sequencing, can also be employed in the methods described herein. Additional suitable sequencing methods include, but are not limited to nucleic acid imaging technologies, e.g., atomic force microscopy (AFM) or transmission electron microscopy (TEM). Illustrative sequencing technologies are described in greater detail below.

In one illustrative, but non-limiting, embodiment, the methods described herein comprise obtaining sequence information for the nucleic acids in a test sample, e.g., cfDNA in a maternal sample, cfDNA or cellular DNA in a subject being screened for a cancer, and the like, using single molecule sequencing technology of the Helicos True Single Molecule Sequencing (tSMS) technology (e.g. as described in Harris T. D. et al., Science 320:106-109 [2008]). In the tSMS technique, a DNA sample is cleaved into strands of approximately 100 to 200 nucleotides, and a polyA sequence is added to the 3' end of each DNA strand. Each strand is labeled by the addition of a fluorescently labeled adenosine nucleotide. The DNA strands are then hybridized to a flow cell, which contains millions of oligo-T capture sites that are immobilized to the flow cell surface. In certain embodiments the templates can be at a density of about 100 million templates/cm2. The flow cell is then loaded into an instrument, e.g., HeliScope™ sequencer, and a laser illuminates the surface of the flow cell, revealing the position of each template. A CCD camera can map the position of the templates on the flow cell surface. The template fluorescent label is then cleaved and washed away. The sequencing reaction begins by introducing a DNA polymerase and a fluorescently labeled nucleotide. The oligo-T nucleic acid serves as a primer. The polymerase incorporates the labeled nucleotides to the primer in a template directed manner. The polymerase and unincorporated nucleotides are removed. The templates that have directed incorporation of the fluorescently labeled nucleotide are discerned by imaging the flow cell surface. After imaging, a cleavage step removes the fluorescent label, and the process is repeated with other fluorescently labeled nucleotides until the desired read length is achieved. Sequence information is collected with each nucleotide addition step. Whole genome sequencing by single molecule sequencing technologies excludes or typically obviates PCR-based amplification in the preparation of the sequencing libraries, and the methods allow for direct measurement of the sample, rather than measurement of copies of that sample.

In another illustrative, but non-limiting embodiment, the methods described herein comprise obtaining sequence information for the nucleic acids in the test sample, e.g., cfDNA in a maternal test sample, cfDNA or cellular DNA in a subject being screened for a cancer, and the like, using the 454 sequencing (Roche) (e.g. as described in Margulies, M. et al. Nature 437:376-380 [2005]). 454 sequencing typically involves two steps. In the first step, DNA is sheared into fragments of approximately 300-800 base pairs, and the fragments are blunt-ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., Adaptor B, which contains 5'-biotin tag. The fragments attached to the beads are PCR amplified within droplets of an oil-water emulsion. The result is multiple copies of clonally amplified DNA fragments on each bead. In the second step, the beads are captured in wells (e.g., picoliter-sized wells). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is measured and analyzed.

In another illustrative, but non-limiting, embodiment, the methods described herein comprises obtaining sequence information for the nucleic acids in the test sample, e.g., cfDNA in a maternal test sample, cfDNA or cellular DNA in a subject being screened for a cancer, and the like, using the SOLiD™ technology (Applied Biosystems). In SOLiD™ sequencing-by-ligation, genomic DNA is sheared into fragments, and adaptors are attached to the 5' and 3' ends of the fragments to generate a fragment library. Alternatively, internal adaptors can be introduced by ligating adaptors to the 5' and 3' ends of the fragments, circularizing the fragments, digesting the circularized fragment to generate an internal adaptor, and attaching adaptors to the 5' and 3' ends of the resulting fragments to generate a mate-paired library. Next, clonal bead populations are prepared in microreactors containing beads, primers, template, and PCR components. Following PCR, the templates are denatured and beads are enriched to separate the beads with extended templates. Templates on the selected beads are subjected to a 3' modification that permits bonding to a glass slide. The sequence can be determined by sequential hybridization and ligation of partially random oligonucleotides with a central determined base (or pair of bases) that is identified by a specific fluorophore. After a color is recorded, the ligated oligonucleotide is cleaved and removed and the process is then repeated.

In another illustrative, but non-limiting, embodiment, the methods described herein comprise obtaining sequence information for the nucleic acids in the test sample, e.g., cfDNA in a maternal test sample, cfDNA or cellular DNA in a subject being screened for a cancer, and the like, using the single molecule, real-time (SMRT™) sequencing technology of Pacific Biosciences. In SMRT sequencing, the continuous incorporation of dye-labeled nucleotides is imaged during DNA synthesis. Single DNA polymerase molecules are attached to the bottom surface of individual zero-mode wavelength detectors (ZMW detectors) that obtain sequence information while phospholinked nucleotides are being incorporated into the growing primer strand. A ZMW detector comprises a confinement structure that enables observation of incorporation of a single nucleotide by DNA polymerase against a background of fluorescent nucleotides that rapidly diffuse in an out of the ZMW (e.g., in microseconds). It typically takes several milliseconds to incorporate a nucleotide into a growing strand. During this time, the fluorescent label is excited and produces a fluorescent signal, and the fluorescent tag is cleaved off. Measurement of the corresponding fluorescence of the dye indicates which base was incorporated. The process is repeated to provide a sequence.

In another illustrative, but non-limiting embodiment, the methods described herein comprise obtaining sequence information for the nucleic acids in the test sample, e.g., cfDNA in a maternal test sample, cfDNA or cellular DNA in a subject being screened for a cancer, and the like, using nanopore sequencing (e.g. as described in Soni G V and Meller A. Clin Chem 53: 1996-2001 [2007]). Nanopore sequencing DNA analysis techniques are developed by a number of companies, including, for example, Oxford Nanopore Technologies (Oxford, United Kingdom), Sequenom, NABsys, and the like. Nanopore sequencing is a single-molecule sequencing technology whereby a single molecule of DNA is sequenced directly as it passes through a nanopore. A nanopore is a small hole, typically of the order of 1 nanometer in diameter. Immersion of a nanopore in a conducting fluid and application of a potential (voltage) across it results in a slight electrical current due to conduction of ions through the nanopore. The amount of current that flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore provides a read of the DNA sequence.

In another illustrative, but non-limiting, embodiment, the methods described herein comprises obtaining sequence information for the nucleic acids in the test sample, e.g., cfDNA in a maternal test sample, cfDNA or cellular DNA in a subject being screened for a cancer, and the like, using the chemical-sensitive field effect transistor (chemFET) array (e.g., as described in U.S. Patent Application Publication No. 2009/0026082). In one example of this technique, DNA molecules can be placed into reaction chambers, and the template molecules can be hybridized to a sequencing primer bound to a polymerase. Incorporation of one or more triphosphates into a new nucleic acid strand at the 3' end of the sequencing primer can be discerned as a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In another embodiment, the present method comprises obtaining sequence information for the nucleic acids in the test sample, e.g., cfDNA in a maternal test sample, using the Halcyon Molecular's technology, which uses transmission electron microscopy (TEM). The method, termed Individual Molecule Placement Rapid Nano Transfer (IMPRNT), comprises utilizing single atom resolution transmission electron microscope imaging of high-molecular weight (150 kb or greater) DNA selectively labeled with heavy atom markers and arranging these molecules on ultra-thin films in ultra-dense (3 nm strand-to-strand) parallel arrays with consistent base-to-base spacing. The electron microscope is used to image the molecules on the films to determine the position of the heavy atom markers and to extract base sequence information from the DNA. The method is further described in PCT patent publication WO 2009/046445. The method allows for sequencing complete human genomes in less than ten minutes.

In another embodiment, the DNA sequencing technology is the Ion Torrent single molecule sequencing, which pairs semiconductor technology with a simple sequencing chemistry to directly translate chemically encoded information (A, C, G, T) into digital information (0, 1) on a semiconductor chip. In nature, when a nucleotide is incorporated into a strand of DNA by a polymerase, a hydrogen ion is released as a byproduct. Ion Torrent uses a high-density array of micro-machined wells to perform this biochemical process in a massively parallel way. Each well holds a different DNA molecule. Beneath the wells is an ion-sensitive layer and beneath that an ion sensor. When a nucleotide, for example a C, is added to a DNA template and is then incorporated into a strand of DNA, a hydrogen ion will be released. The charge from that ion will change the pH of the solution, which can be detected by Ion Torrent's ion sensor. The sequencer—essentially the world's smallest solid-state pH meter—calls the base, going directly from chemical information to digital information. The Ion personal Genome Machine (PGM™) sequencer then sequentially floods the chip with one nucleotide after another. If the next nucleotide that floods the chip is not a match. No voltage change will be recorded and no base will be called. If there are two identical bases on the DNA strand, the voltage will be double, and the chip will record two identical bases called. Direct detection allows recordation of nucleotide incorporation in seconds.

In another embodiment, the present method comprises obtaining sequence information for the nucleic acids in the test sample, e.g., cfDNA in a maternal test sample, using sequencing by hybridization. Sequencing-by-hybridization comprises contacting the plurality of polynucleotide sequences with a plurality of polynucleotide probes, wherein each of the plurality of polynucleotide probes can be optionally tethered to a substrate. The substrate might be flat surface comprising an array of known nucleotide sequences. The pattern of hybridization to the array can be used to determine the polynucleotide sequences present in the sample. In other embodiments, each probe is tethered to a bead, e.g., a magnetic bead or the like. Hybridization to the beads can be determined and used to identify the plurality of polynucleotide sequences within the sample.

In another embodiment, the present method comprises obtaining sequence information for the nucleic acids in the test sample, e.g., cfDNA in a maternal test sample, by massively parallel sequencing of millions of DNA fragments using Illumina's sequencing-by-synthesis and reversible terminator-based sequencing chemistry (e.g. as described in Bentley et al., Nature 6:53-59 [2009]). Template DNA can be genomic DNA, e.g., cfDNA. In some embodiments, genomic DNA from isolated cells is used as the template, and it is fragmented into lengths of several hundred base pairs. In other embodiments, cfDNA is used as the template, and fragmentation is not required as cfDNA exists as short fragments. For example fetal cfDNA circulates in the bloodstream as fragments approximately 170 base pairs (bp) in length (Fan et al., Clin Chem 56:1279-1286 [2010]), and no fragmentation of the DNA is required prior to sequencing. Illumina's sequencing technology relies on the attachment of fragmented genomic DNA to a planar, optically transparent surface on which oligonucleotide anchors are bound. Template DNA is end-repaired to generate 5'-phosphorylated blunt ends, and the polymerase activity of Klenow fragment is used to add a single A base to the 3' end of the blunt phosphorylated DNA fragments. This addition prepares the DNA fragments for ligation to oligonucleotide adapters, which have an overhang of a single T base at their 3' end to increase ligation efficiency. The adapter oligonucleotides are complementary to the flow-cell anchors. Under limiting-dilution conditions, adapter-modified, single-stranded template DNA is added to the flow cell and immobilized by hybridization to the anchors. Attached DNA fragments are extended and bridge amplified to create an ultra-high density sequencing flow cell with hundreds of millions of clusters, each containing 1,000 copies of the same template. In one embodiment, the randomly fragmented genomic DNA, e.g., cfDNA, is amplified using PCR before it is subjected to cluster amplification. Alternatively, an amplification-free genomic library preparation is used, and the randomly fragmented genomic DNA, e.g., cfDNA is enriched using the cluster amplification alone (Kozarewa et al., Nature Methods 6:291-295 [2009]). The templates are sequenced using a robust four-color DNA sequencing-by-synthesis technology that employs reversible terminators with removable fluorescent dyes. High-sensitivity fluorescence detection is achieved using laser excitation and total internal reflection optics. Short sequence reads of about 20-40 bp, e.g., 36 bp, are aligned against a repeat-masked reference genome and unique mapping of the short sequence reads to the reference genome are identified using specially developed data analysis pipeline software. Non-repeat-masked reference genomes can also be used. Whether repeat-masked or non-repeat-masked reference genomes are used, only reads that map uniquely to the reference genome are counted. After completion of the first read, the templates can be regenerated in situ to enable a second read from the opposite end of the fragments. Thus, either single-end or paired end sequencing of the DNA fragments can be used. Partial sequencing of DNA fragments present in the sample is performed, and sequence tags comprising reads of predetermined length, e.g., 36 bp, are mapped to a known reference genome are counted. In one embodiment, the reference genome sequence is the NCBI36/hg18 sequence, which is available on the world wide web at genome.ucsc.edu/cgi-bin/hgGateway?org=Human&db=hg18&hgsid=166260105). Alternatively, the reference genome sequence is the GRCh37/hg19, which is available on the world wide web at genome.ucsc.edu/cgi-bin/hgGateway. Other sources of public sequence information include GenBank, dbEST, dbSTS, EMBL (the European Molecular Biology Laboratory), and the DDBJ (the DNA Databank of Japan). A number of computer algorithms are available for aligning sequences, including without limitation BLAST (Altschul et al., 1990), BLITZ (MPsrch) (Sturrock & Collins, 1993), FASTA (Person & Lipman, 1988), BOWTIE (Langmead et al., Genome Biology 10:R25.1-R25.10 [2009]), or ELAND (Illumina, Inc., San Diego, Calif., USA). In one embodiment, one end of the clonally expanded copies of the plasma cfDNA molecules is sequenced and processed by bioinformatics alignment analysis for the Illumina Genome Analyzer, which uses the Efficient Large-Scale Alignment of Nucleotide Databases (ELAND) software.

In some embodiments of the methods described herein, the mapped sequence tags comprise sequence reads of about 20 bp, about 25 bp, about 30 bp, about 35 bp, about 40 bp, about 45 bp, about 50 bp, about 55 bp, about 60 bp, about 65 bp, about 70 bp, about 75 bp, about 80 bp, about 85 bp, about 90 bp, about 95 bp, about 100 bp, about 110 bp, about 120 bp, about 130, about 140 bp, about 150 bp, about 200 bp, about 250 bp, about 300 bp, about 350 bp, about 400 bp, about 450 bp, or about 500 bp. It is expected that technological advances will enable single-end reads of greater than 500 bp enabling for reads of greater than about 1000 bp when paired end reads are generated. In one embodiment, the mapped sequence tags comprise sequence reads that are 36 bp. Mapping of the sequence tags is achieved by comparing the sequence of the tag with the sequence of the reference to determine the chromosomal origin of the sequenced nucleic acid (e.g. cfDNA) molecule, and specific genetic sequence information is not needed. A small degree of mismatch (0-2 mismatches per sequence tag) may be allowed to account for minor polymorphisms that may exist between the reference genome and the genomes in the mixed sample.

A plurality of sequence tags are typically obtained per sample. In some embodiments, at least about $3 \times 10^6$ sequence tags, at least about $5 \times 10^6$ sequence tags, at least about $8 \times 10^6$ sequence tags, at least about $10 \times 10^6$ sequence tags, at least about $15 \times 10^6$ sequence tags, at least about $20 \times 10^6$ sequence tags, at least about $30 \times 10^6$ sequence tags, at least about $40 \times 10^6$ sequence tags, or at least about $50 \times 10^6$ sequence tags comprising between 20 and 40 bp reads, e.g., 36 bp, are obtained from mapping the reads to the reference genome per sample. In one embodiment, all the sequence reads are mapped to all regions of the reference genome. In one embodiment, the tags that have been mapped to all regions, e.g., all chromosomes, of the reference genome are counted, and the CNV, i.e., the over- or under-representation of a sequence of interest, e.g., a chromosome or portion thereof, in the mixed DNA sample is determined. The method does not require differentiation between the two genomes.

The accuracy required for correctly determining whether a CNV, e.g., aneuploidy, is present or absent in a sample, is predicated on the variation of the number of sequence tags that map to the reference genome among samples within a sequencing run (inter-chromosomal variability), and the variation of the number of sequence tags that map to the reference genome in different sequencing runs (inter-sequencing variability). For example, the variations can be particularly pronounced for tags that map to GC-rich or GC-poor reference sequences. Other variations can result from using different protocols for the extraction and purification of the nucleic acids, the preparation of the sequencing libraries, and the use of different sequencing platforms. The present method uses sequence doses (chromosome doses, or segment doses) based on the knowledge of normalizing sequences (normalizing chromosome sequences or normalizing segment sequences), to intrinsically account for the accrued variability stemming from interchromosomal (intra-run), and inter-sequencing (inter-run) and platform-dependent variability. Chromosome doses are based on the knowledge of a normalizing chromosome sequence, which can be composed of a single chromosome, or of two or more chromosomes selected from chromosomes 1-22, X, and Y. Alternatively, normalizing chromosome sequences can be composed of a single chromosome segment, or of two or more segments of one chromosome or of two or more chromosomes. Segment doses are based on the knowledge of a normalizing segment sequence, which can be composed of a single segment of any one chromosome, or of two or more segments of any two or more of chromosomes 1-22, X, and Y.

CNV and Prenatal Diagnoses

Cell-free fetal DNA and RNA circulating in maternal blood can be used for the early non-invasive prenatal diagnosis (NIPD) of an increasing number of genetic conditions, both for pregnancy management and to aid reproductive decision-making. The presence of cell-free DNA circulating in the bloodstream has been known for over 50 years. More recently, presence of small amounts of circulating fetal DNA was discovered in the maternal bloodstream during pregnancy (Lo et al., Lancet 350:485-487 [1997]). Thought to originate from dying placental cells, cell-free fetal DNA (cfDNA) has been shown to consists of short fragments typically fewer than 200 bp in length Chan et al., Clin Chem 50:88-92 [2004]), which can be discerned as early as 4 weeks gestation (Illanes et al., Early Human Dev 83:563-566 [2007]), and known to be cleared from the maternal circulation within hours of delivery (Lo et al., Am J Hum Genet 64:218-224 [1999]). In addition to cfDNA, fragments of cell-free fetal RNA (cfRNA) can also be discerned in the maternal bloodstream, originating from genes that are transcribed in the fetus or placenta. The extraction and subsequent analysis of these fetal genetic elements from a maternal blood sample offers novel opportunities for NIPD.

The present method is a polymorphism-independent method that for use in NIPD and that does not require that the fetal cfDNA be distinguished from the maternal cfDNA to enable the determination of a fetal aneuploidy. In some embodiments, the aneuploidy is a complete chromosomal trisomy or monosomy, or a partial trisomy or monosomy. Partial aneuploidies are caused by loss or gain of part of a chromosome, and encompass chromosomal imbalances resulting from unbalanced translocations, unbalanced inversions, deletions and insertions. By far, the most common known aneuploidy compatible with life is trisomy 21, i.e., Down Syndrome (DS), which is caused by the presence of part or all of chromosome 21. Rarely, DS can be caused by an inherited or sporadic defect whereby an extra copy of all or part of chromosome 21 becomes attached to another chromosome (usually chromosome 14) to form a single aberrant chromosome. DS is associated with intellectual impairment, severe learning difficulties and excess mortality caused by long-term health problems such as heart disease. Other aneuploidies with known clinical significance include Edward syndrome (trisomy 18) and Patau Syndrome (trisomy 13), which are frequently fatal within the first few months of life. Abnormalities associated with the number of sex chromosomes are also known and include monosomy X, e.g., Turner syndrome (XO), and triple X syndrome (XXX) in female births and Kleinefelter syndrome (XXY) and XYY syndrome in male births, which are all associated with various phenotypes including sterility and reduction in intellectual skills. Monosomy X [45, X] is a common cause of early pregnancy loss accounting for about 7% of spontaneous abortions. Based on the liveborn frequency of 45,X (also called Turner syndrome) of 1-2/10,000, it is estimated that less than 1% of 45,X conceptions will survive to term. About 30% of Turners syndrome patients are mosaic with both a 45,X cell line and either a 46,XX cell line or one containing a rearranged X chromosome (Hook and Warburton 1983). The phenotype in a liveborn infant is relatively mild considering the high embryonic lethality and it has been hypothesized that possibly all liveborn females with Turner syndrome carry a cell line containing two sex chromosomes. Monosomy X can occur in females as 45,X or as 45,X/46XX, and in males as 45,X/46XY. Autosomal monosomies in human are generally suggested to be incompatible with life; however, there is quite a number of cytogenetic reports describing full monosomy of one chromosome 21 in live born children (Vosranova I et al., Molecular Cytogen. 1:13 [2008]; Joosten et al., Prenatal Diagn. 17:271-5 [1997]. The method described herein can be used to diagnose these and other chromosomal abnormalities prenatally.

According to some embodiments the methods disclosed herein can determine the presence or absence of chromosomal trisomies of any one of chromosomes 1-22, X and Y. Examples of chromosomal trisomies that can be detected according to the present method include without limitation trisomy 21 (T21; Down Syndrome), trisomy 18 (T18; Edward's Syndrome), trisomy 16 (T16), trisomy 20 (T20), trisomy 22 (T22; Cat Eye Syndrome), trisomy 15 (T15; Prader Willi Syndrome), trisomy 13 (T13; Patau Syndrome), trisomy 8 (T8; Warkany Syndrome), trisomy 9, and the XXY (Kleinefelter Syndrome), XYY, or XXX trisomies. Complete trisomies of other autosomes existing in a non-mosaic state are lethal, but can be compatible with life when present in a mosaic state. It will be appreciated that various complete trisomies, whether existing in a mosaic or non-mosaic state, and partial trisomies can be determined in fetal cfDNA according to the teachings provided herein.

Non-limiting examples of partial trisomies that can be determined by the present method include, but are not limited to, partial trisomy 1q32-44, trisomy 9 p, trisomy 4 mosaicism, trisomy 17p, partial trisomy 4q26-qter, partial 2p trisomy, partial trisomy 1q, and/or partial trisomy 6p/monosomy 6q.

The methods disclosed herein can be also used to determine chromosomal monosomy X, chromosomal monosomy 21, and partial monosomies such as, monosomy 13, monosomy 15, monosomy 16, monosomy 21, and monosomy 22, which are known to be involved in pregnancy miscarriage. Partial monosomy of chromosomes typically involved in complete aneuploidy can also be determined by the method described herein. Non-limiting examples of deletion syndromes that can be determined according to the present method include syndromes caused by partial deletions of chromosomes. Examples of partial deletions that can be determined according to the methods described herein include without limitation partial deletions of chromosomes 1, 4, 5, 7, 11, 18, 15, 13, 17, 22 and 10, which are described in the following.

1q21.1 deletion syndrome or 1q21.1 (recurrent) microdeletion is a rare aberration of chromosome 1. Next to the deletion syndrome, there is also a 1q21.1 duplication syndrome. While there is a part of the DNA missing with the deletion syndrome on a particular spot, there are two or three copies of a similar part of the DNA on the same spot with the duplication syndrome. Literature refers to both the deletion and the duplication as the 1q21.1 copy-number variations (CNV). The 1q21.1 deletion can be associated with the TAR Syndrome (Thrombocytopenia with Absent radius).

Wolf-Hirschhorn syndrome (WHS) (OMIN #194190) is a contiguous gene deletion syndrome associated with a hemizygous deletion of 4p16.3. Wolf-Hirschhorn syndrome is a congenital malformation syndrome characterized by pre- and postnatal growth deficiency, developmental disability of variable degree, characteristic craniofacial features ('Greek warrior helmet' appearance of the nose, high forehead, prominent glabella, hypertelorism, high-arched eyebrows, protruding eyes, epicanthal folds, short philtrum, distinct mouth with downturned corners, and micrognathia), and a seizure disorder.

Partial deletion of chromosome 5, also known as 5p– or 5p minus, and named Cris du Chat syndrome (OMIN #123450), is caused by a deletion of the short arm (p arm) of chromosome 5 (5p15.3-p15.2). Infants with this condition often have a high-pitched cry that sounds like that of a cat. The disorder is characterized by intellectual disability and delayed development, small head size (microcephaly), low birth weight, and weak muscle tone (hypotonia) in infancy, distinctive facial features and possibly heart defects.

Williams-Beuren Syndrome also known as chromosome 7q11.23 deletion syndrome (OMIN 194050) is a contiguous gene deletion syndrome resulting in a multisystem disorder caused by hemizygous deletion of 1.5 to 1.8 Mb on chromosome 7q11.23, which contains approximately 28 genes.

Jacobsen Syndrome, also known as 11 q deletion disorder, is a rare congenital disorder resulting from deletion of a terminal region of chromosome 11 that includes band 11q24.1. It can cause intellectual disabilities, a distinctive facial appearance, and a variety of physical problems including heart defects and a bleeding disorder.

Partial monosomy of chromosome 18, known as monosomy 18p is a rare chromosomal disorder in which all or part of the short arm (p) of chromosome 18 is deleted (monosomic). The disorder is typically characterized by short stature, variable degrees of mental retardation, speech delays, malformations of the skull and facial (craniofacial) region, and/or additional physical abnormalities. Associated craniofacial defects may vary greatly in range and severity from case to case.

Conditions caused by changes in the structure or number of copies of chromosome 15 include Angelman Syndrome and Prader-Willi Syndrome, which involve a loss of gene activity in the same part of chromosome 15, the 15q11-q13 region. It will be appreciated that several translocations and microdeletions can be asymptomatic in the carrier parent, yet can cause a major genetic disease in the offspring. For example, a healthy mother who carries the 15q11-q13 microdeletion can give birth to a child with Angelman syndrome, a severe neurodegenerative disorder. Thus, the methods, apparatus and systems described herein can be used to identify such a partial deletion and other deletions in the fetus.

Partial monosomy 13q is a rare chromosomal disorder that results when a piece of the long arm (q) of chromosome 13 is missing (monosomic). Infants born with partial monosomy 13q may exhibit low birth weight, malformations of the head and face (craniofacial region), skeletal abnormalities (especially of the hands and feet), and other physical abnormalities. Mental retardation is characteristic of this condition. The mortality rate during infancy is high among individuals born with this disorder. Almost all cases of partial monosomy 13q occur randomly for no apparent reason (sporadic).

Smith-Magenis syndrome (SMS—OMIM #182290) is caused by a deletion, or loss of genetic material, on one copy of chromosome 17. This well-known syndrome is associated with developmental delay, mental retardation, congenital anomalies such as heart and kidney defects, and neurobehavioral abnormalities such as severe sleep disturbances and self-injurious behavior. Smith-Magenis syndrome (SMS) is caused in most cases (90%) by a 3.7-Mb interstitial deletion in chromosome 17p11.2.

22q11.2 deletion syndrome, also known as DiGeorge syndrome, is a syndrome caused by the deletion of a small piece of chromosome 22. The deletion (22 q11.2) occurs near the middle of the chromosome on the long arm of one of the pair of chromosome. The features of this syndrome vary widely, even among members of the same family, and affect many parts of the body. Characteristic signs and symptoms may include birth defects such as congenital heart disease, defects in the palate, most commonly related to neuromuscular problems with closure (velo-pharyngeal insufficiency), learning disabilities, mild differences in facial features, and recurrent infections. Microdeletions in chromosomal region 22q11.2 are associated with a 20 to 30-fold increased risk of schizophrenia.

Deletions on the short arm of chromosome 10 are associated with a DiGeorge Syndrome like phenotype. Partial monosomy of chromosome 10p is rare but has been observed in a portion of patients showing features of the DiGeorge Syndrome.

In one embodiment, the methods, apparatus, and systems described herein is used to determine partial monosomies including but not limited to partial monosomy of chromosomes 1, 4, 5, 7, 11, 18, 15, 13, 17, 22 and 10, e.g., partial monosomy 1q21.11, partial monosomy 4p16.3, partial monosomy 5p15.3-p15.2, partial monosomy 7q11.23, partial monosomy 11q24.1, partial monosomy 18p, partial monosomy of chromosome 15 (15g11-q13), partial monosomy 13q, partial monosomy 17p11.2, partial monosomy of chromosome 22 (22q11.2), and partial monosomy 10p can also be determined using the method.

Other partial monosomies that can be determined according to the methods described herein include unbalanced translocation t(8; 11)(p23.2; p15.5); 11q23 microdeletion; 17p11.2 deletion; 22q13.3 deletion; Xp22.3 microdeletion; 10p14 deletion; 20p microdeletion, [del(22)(q11.2q11.23)], 7q11.23 and 7q36 deletions; 1p36 deletion; 2p microdeletion; neurofibromatosis type 1 (17q11.2 microdeletion), Yq deletion; 4p16.3 microdeletion; 1p36.2 microdeletion; 11q14 deletion; 19q13.2 microdeletion; Rubinstein-Taybi (16 p13.3 microdeletion); 7p21 microdeletion; Miller-Dieker syndrome (17p13.3); and 2q37 microdeletion. Partial deletions can be small deletions of part of a chromosome, or they can be microdeletions of a chromosome where the deletion of a single gene can occur.

Several duplication syndromes caused by the duplication of part of chromosome arms have been identified (see OMIN [Online Mendelian Inheritance in Man viewed online at ncbi.nlm.nih.gov/omim]). In one embodiment, the present method can be used to determine the presence or absence of duplications and/or multiplications of segments of any one of chromosomes 1-22, X and Y. Non-limiting examples of duplications syndromes that can be determined according to the present method include duplications of part of chromosomes 8, 15, 12, and 17, which are described in the following.

8p23.1 duplication syndrome is a rare genetic disorder caused by a duplication of a region from human chromosome 8. This duplication syndrome has an estimated prevalence of 1 in 64,000 births and is the reciprocal of the 8p23.1 deletion syndrome. The 8p23.1 duplication is associated with a variable phenotype including one or more of speech delay, developmental delay, mild dysmorphism, with prominent forehead and arched eyebrows, and congenital heart disease (CHD).

Chromosome 15q Duplication Syndrome (Dup15q) is a clinically identifiable syndrome which results from duplications of chromosome 15q11-13.1 Babies with Dup15q usually have hypotonia (poor muscle tone), growth retardation; they may be born with a cleft lip and/or palate or malformations of the heart, kidneys or other organs; they show some degree of cognitive delay/disability (mental retardation), speech and language delays, and sensory processing disorders.

Pallister Killian syndrome is a result of extra #12 chromosome material. There is usually a mixture of cells (mosaicism), some with extra #12 material, and some that are normal (46 chromosomes without the extra #12 material). Babies with this syndrome have many problems including severe mental retardation, poor muscle tone, "coarse" facial features, and a prominent forehead. They tend to have a very thin upper lip with a thicker lower lip and a short nose. Other health problems include seizures, poor feeding, stiff joints, cataracts in adulthood, hearing loss, and heart defects. Persons with Pallister Killian have a shortened lifespan.

Individuals with the genetic condition designated as dup (17)(p11.2p11.2) or dup 17p carry extra genetic information (known as a duplication) on the short arm of chromosome 17. Duplication of chromosome 17p11.2 underlies Potocki-Lupski syndrome (PTLS), which is a newly recognized genetic condition with only a few dozen cases reported in the medical literature. Patients who have this duplication often have low muscle tone, poor feeding, and failure to thrive during infancy, and also present with delayed development of motor and verbal milestones. Many individuals who have PTLS have difficulty with articulation and language processing. In addition, patients may have behavioral characteristics similar to those seen in persons with autism or autism-spectrum disorders. Individuals with PTLS may have heart defects and sleep apnea. A duplication of a large region in chromosome 17p12 that includes the gene PMP22 is known to cause Charcot-Marie Tooth disease.

CNV have been associated with stillbirths. However, due to inherent limitations of conventional cytogenetics, the contribution of CNV to stillbirth is thought to be underrepresented (Harris et al., Prenatal Diagn 31:932-944 [2011]). As is shown in the examples and described elsewhere herein, the present method is capable of determining the presence of partial aneuploidies, e.g., deletions and multiplications of chromosome segments, and can be used to identify and determine the presence or absence of CNV that are associated with stillbirths.

Apparatus and Systems for Determining CNV

Analysis of the sequencing data and the diagnosis derived therefrom are typically performed using various computer executed algorithms and programs. Therefore, certain embodiments employ processes involving data stored in or transferred through one or more computer systems or other processing systems. Embodiments disclosed herein also relate to apparatus for performing these operations. This apparatus may be specially constructed for the required purposes, or it may be a general-purpose computer (or a group of computers) selectively activated or reconfigured by a computer program and/or data structure stored in the computer. In some embodiments, a group of processors performs some or all of the recited analytical operations collaboratively (e.g., via a network or cloud computing) and/or in parallel. A processor or group of processors for performing the methods described herein may be of various types including microcontrollers and microprocessors such as programmable devices (e.g., CPLDs and FPGAs) and non-programmable devices such as gate array ASICs or general purpose microprocessors.

In addition, certain embodiments relate to tangible and/or non-transitory computer readable media or computer program products that include program instructions and/or data (including data structures) for performing various computer-implemented operations. Examples of computer-readable media include, but are not limited to, semiconductor memory devices, magnetic media such as disk drives, magnetic tape, optical media such as CDs, magneto-optical media, and hardware devices that are specially configured to store and perform program instructions, such as read-only memory devices (ROM) and random access memory (RAM). The computer readable media may be directly controlled by an end user or the media may be indirectly controlled by the end user. Examples of directly controlled media include the media located at a user facility and/or media that are not shared with other entities. Examples of indirectly controlled media include media that is indirectly accessible to the user via an external network and/or via a service providing shared resources such as the "cloud." Examples of program instructions include both machine code, such as produced by a compiler, and files containing higher level code that may be executed by the computer using an interpreter.

In various embodiments, the data or information employed in the disclosed methods and apparatus is provided in an electronic format. Such data or information may include reads and tags derived from a nucleic acid sample, counts or densities of such tags that align with particular regions of a reference sequence (e.g., that align to a chromosome or chromosome segment), reference sequences (including reference sequences providing solely or primarily polymorphisms), chromosome and segment doses, calls such as aneuploidy calls, normalized chromosome and segment values, pairs of chromosomes or segments and corresponding normalizing chromosomes or segments, counseling recommendations, diagnoses, and the like. As used herein, data or other information provided in electronic format is available for storage on a machine and transmission between machines. Conventionally, data in electronic format is provided digitally and may be stored as bits and/or bytes in various data structures, lists, databases, etc. The data may be embodied electronically, optically, etc.

One embodiment provides a computer program product for generating an output indicating the presence or absence of an aneuploidy, e.g., a fetal aneuploidy or cancer, in a test sample. The computer product may contain instructions for performing any one or more of the above-described methods for determining a chromosomal anomaly. As explained, the computer product may include a non-transitory and/or tangible computer readable medium having a computer executable or compilable logic (e.g., instructions) recorded thereon for enabling a processor to determine chromosome doses and, in some cases, whether a fetal aneuploidy is present or absent. In one example, the computer product comprises a computer readable medium having a computer executable or compilable logic (e.g., instructions) recorded thereon for enabling a processor to diagnose a fetal aneuploidy comprising: a receiving procedure for receiving sequencing data from at least a portion of nucleic acid molecules from a maternal biological sample, wherein said sequencing data comprises a calculated chromosome and/or segment dose; computer assisted logic for analyzing a fetal aneuploidy from said received data; and an output procedure for generating an output indicating the presence, absence or kind of said fetal aneuploidy.

The sequence information from the sample under consideration may be mapped to chromosome reference sequences to identify a number of sequence tags for each of any one or more chromosomes of interest and to identify a number of sequence tags for a normalizing segment sequence for each of said any one or more chromosomes of interest. In various embodiments, the reference sequences are stored in a database such as a relational or object database, for example.

It should be understood that it is not practical, or even possible in most cases, for an unaided human being to perform the computational operations of the methods disclosed herein. For example, mapping a single 30 bp read from a sample to any one of the human chromosomes might require years of effort without the assistance of a computational apparatus. Of course, the problem is compounded because reliable aneuploidy calls generally require mapping thousands (e.g., at least about 10,000) or even millions of reads to one or more chromosomes.

The methods disclosed herein can be performed using a system for evaluation of copy number of a genetic sequence of interest in a test sample. The system comprising: (a) a sequencer for receiving nucleic acids from the test sample providing nucleic acid sequence information from the sample; (b) a processor; and (c) one or more computer-readable storage media having stored thereon instructions for execution on said processor to carry out a method for identifying any CNV, e.g., chromosomal or partial aneuploidies.

In some embodiments, the methods are instructed by a computer-readable medium having stored thereon computer-readable instructions for carrying out a method for identifying any CNV, e.g., chromosomal or partial aneuploidies. Thus one embodiment provides a computer program product comprising one or more computer-readable non-transitory storage media having stored thereon computer-executable instructions that, when executed by one or more processors of a computer system, cause the computer system to implement a method for evaluation of copy number of a sequence of interest in a test sample comprising fetal and maternal cell-free nucleic acids. The method includes: (a) providing sequence reads of the test sample; (b) aligning the sequence reads of the test sample to a reference genome comprising the sequence of interest, thereby providing test sequence tags; (c) determining a coverage of the test sequence tags located in each bin, wherein the reference genome is divided into a plurality of bins; (d) providing a global profile for the sequence of interest, wherein the global profile comprises an expected coverage in each bin, and wherein the expected coverage is obtained from a training set of unaffected training samples sequenced and aligned in substantially the same manner as the test sample, the expected coverage exhibiting variation from bin to bin; (e) adjusting the coverage of the test sequence tags according to the expected coverage in each bin, thereby obtaining a global-profile-corrected coverage in each bin of the test sequence tags; (f) adjusting the global-profile-corrected coverages based on the relation between GC content level and the global-profile-corrected coverage for the bins of the test sequence tags, thereby obtaining a sample-GC-corrected coverage of the test sequence tags on the sequence of interest; and (g) evaluating a copy number of the sequence of interest in the test sample based on the sample-GC-corrected coverage. In some embodiments, the coverage determined in step (c) is normalized. The normalization may involve dividing the coverage by or modeling the coverage from the total number of reads mapping to robust chromosomes (sometimes also referred to as library depth normalization).

In some embodiments, the instructions may further include automatically recording information pertinent to the method such as chromosome doses and the presence or absence of a fetal chromosomal aneuploidy in a patient medical record for a human subject providing the maternal test sample. The patient medical record may be maintained by, for example, a laboratory, physician's office, a hospital, a health maintenance organization, an insurance company, or a personal medical record website. Further, based on the results of the processor-implemented analysis, the method may further involve prescribing, initiating, and/or altering treatment of a human subject from whom the maternal test sample was taken. This may involve performing one or more additional tests or analyses on additional samples taken from the subject.

Disclosed methods can also be performed using a computer processing system which is adapted or configured to perform a method for identifying any CNV, e.g., chromosomal or partial aneuploidies. One embodiment provides a computer processing system which is adapted or configured to perform a method as described herein. In one embodiment, the apparatus comprises a sequencing device adapted or configured for sequencing at least a portion of the nucleic acid molecules in a sample to obtain the type of sequence information described elsewhere herein. The apparatus may also include components for processing the sample. Such components are described elsewhere herein.

Sequence or other data, can be input into a computer or stored on a computer readable medium either directly or indirectly. In one embodiment, a computer system is directly coupled to a sequencing device that reads and/or analyzes sequences of nucleic acids from samples. Sequences or other information from such tools are provided via interface in the computer system. Alternatively, the sequences processed by system are provided from a sequence storage source such as a database or other repository. Once available to the processing apparatus, a memory device or mass storage device buffers or stores, at least temporarily, sequences of the nucleic acids. In addition, the memory device may store tag counts for various chromosomes or genomes, etc. The memory may also store various routines and/or programs for analyzing the presenting the sequence or mapped data. Such programs/routines may include programs for performing statistical analyses, etc.

In one example, a user provides a sample into a sequencing apparatus. Data is collected and/or analyzed by the sequencing apparatus which is connected to a computer. Software on the computer allows for data collection and/or analysis. Data can be stored, displayed (via a monitor or other similar device), and/or sent to another location. The computer may be connected to the internet which is used to transmit data to a handheld device utilized by a remote user (e.g., a physician, scientist or analyst). It is understood that the data can be stored and/or analyzed prior to transmittal. In some embodiments, raw data is collected and sent to a remote user or apparatus that will analyze and/or store the data. Transmittal can occur via the internet, but can also occur via satellite or other connection. Alternately, data can be stored on a computer-readable medium and the medium can be shipped to an end user (e.g., via mail). The remote user can be in the same or a different geographical location including, but not limited to a building, city, state, country or continent.

In some embodiments, the methods also include collecting data regarding a plurality of polynucleotide sequences (e.g., reads, tags and/or reference chromosome sequences) and sending the data to a computer or other computational system. For example, the computer can be connected to laboratory equipment, e.g., a sample collection apparatus, a nucleotide amplification apparatus, a nucleotide sequencing apparatus, or a hybridization apparatus. The computer can then collect applicable data gathered by the laboratory device. The data can be stored on a computer at any step, e.g., while collected in real time, prior to the sending, during or in conjunction with the sending, or following the sending. The data can be stored on a computer-readable medium that can be extracted from the computer. The data collected or stored can be transmitted from the computer to a remote location, e.g., via a local network or a wide area network such as the internet. At the remote location various operations can be performed on the transmitted data as described below.

Among the types of electronically formatted data that may be stored, transmitted, analyzed, and/or manipulated in systems, apparatus, and methods disclosed herein are the following:
  Reads obtained by sequencing nucleic acids in a test sample
  Tags obtained by aligning reads to a reference genome or other reference sequence or sequences
  The reference genome or sequence
  Sequence tag density—Counts or numbers of tags for each of two or more regions (typically chromosomes or chromosome segments) of a reference genome or other reference sequences
  Identities of normalizing chromosomes or chromosome segments for particular chromosomes or chromosome segments of interest
  Doses for chromosomes or chromosome segments (or other regions) obtained from chromosomes or segments of interest and corresponding normalizing chromosomes or segments
  Thresholds for calling chromosome doses as either affected, non-affected, or no call
  The actual calls of chromosome doses
  Diagnoses (clinical condition associated with the calls)
  Recommendations for further tests derived from the calls and/or diagnoses
  Treatment and/or monitoring plans derived from the calls and/or diagnoses These various types of data may be obtained, stored transmitted, analyzed, and/or manipulated at one or more locations using distinct apparatus. The processing options span a wide spectrum. At one end of the spectrum, all or much of this information is stored and used at the location where the test sample is processed, e.g., a doctor's office or other clinical setting. In other extreme, the sample is obtained at one location, it is processed and optionally sequenced at a different location, reads are aligned and calls are made at one or more different locations, and diagnoses, recommendations, and/or plans are prepared at still another location (which may be a location where the sample was obtained).

In various embodiments, the reads are generated with the sequencing apparatus and then transmitted to a remote site where they are processed to produce aneuploidy calls. At this remote location, as an example, the reads are aligned to a reference sequence to produce tags, which are counted and assigned to chromosomes or segments of interest. Also at the remote location, the counts are converted to doses using associated normalizing chromosomes or segments. Still further, at the remote location, the doses are used to generate aneuploidy calls.

Among the processing operations that may be employed at distinct locations are the following:
  Sample collection
  Sample processing preliminary to sequencing
  Sequencing
  Analyzing sequence data and deriving aneuploidy calls
  Diagnosis
  Reporting a diagnosis and/or a call to patient or health care provider Developing a plan for further treatment, testing, and/or monitoring Executing the plan Counseling Any one or more of these operations may be automated as described elsewhere herein. Typically, the sequencing and the analyzing of sequence data and deriving aneuploidy calls will be performed computationally. The other operations may be performed manually or automatically.

Examples of locations where sample collection may be performed include health practitioners' offices, clinics, patients' homes (where a sample collection tool or kit is provided), and mobile health care vehicles. Examples of locations where sample processing prior to sequencing may be performed include health practitioners' offices, clinics, patients' homes (where a sample processing apparatus or kit is provided), mobile health care vehicles, and facilities of aneuploidy analysis providers. Examples of locations where sequencing may be performed include health practitioners' offices, clinics, health practitioners' offices, clinics, patients' homes (where a sample sequencing apparatus and/or kit is provided), mobile health care vehicles, and facilities of aneuploidy analysis providers. The location where the sequencing takes place may be provided with a dedicated network connection for transmitting sequence data (typically reads) in an electronic format. Such connection may be wired or wireless and have and may be configured to send the data to a site where the data can be processed and/or aggregated prior to transmission to a processing site. Data aggregators can be maintained by health organizations such as Health Maintenance Organizations (HMOs).

The analyzing and/or deriving operations may be performed at any of the foregoing locations or alternatively at a further remote site dedicated to computation and/or the service of analyzing nucleic acid sequence data. Such locations include for example, clusters such as general purpose server farms, the facilities of an aneuploidy analysis service business, and the like. In some embodiments, the computational apparatus employed to perform the analysis is leased or rented. The computational resources may be part of an internet accessible collection of processors such as processing resources colloquially known as the cloud. In some cases, the computations are performed by a parallel or massively parallel group of processors that are affiliated or unaffiliated with one another. The processing may be accomplished using distributed processing such as cluster computing, grid computing, and the like. In such embodiments, a cluster or grid of computational resources collective form a super virtual computer composed of multiple processors or computers acting together to perform the analysis and/or derivation described herein. These technologies as well as more conventional supercomputers may be employed to process sequence data as described herein. Each is a form of parallel computing that relies on processors or computers. In the case of grid computing these processors (often whole computers) are connected by a network (private, public, or the Internet) by a conventional network protocol such as Ethernet. By contrast, a supercomputer has many processors connected by a local high-speed computer bus.

In certain embodiments, the diagnosis (e.g., the fetus has Downs syndrome or the patient has a particular type of cancer) is generated at the same location as the analyzing operation. In other embodiments, it is performed at a different location. In some examples, reporting the diagnosis is performed at the location where the sample was taken, although this need not be the case. Examples of locations where the diagnosis can be generated or reported and/or where developing a plan is performed include health practitioners' offices, clinics, internet sites accessible by computers, and handheld devices such as cell phones, tablets, smart phones, etc. having a wired or wireless connection to a network. Examples of locations where counseling is performed include health practitioners' offices, clinics, internet sites accessible by computers, handheld devices, etc.

In some embodiments, the sample collection, sample processing, and sequencing operations are performed at a first location and the analyzing and deriving operation is performed at a second location. However, in some cases, the sample collection is collected at one location (e.g., a health practitioner's office or clinic) and the sample processing and sequencing is performed at a different location that is optionally the same location where the analyzing and deriving take place.

In various embodiments, a sequence of the above-listed operations may be triggered by a user or entity initiating sample collection, sample processing and/or sequencing. After one or more these operations have begun execution the other operations may naturally follow. For example, the sequencing operation may cause reads to be automatically collected and sent to a processing apparatus which then conducts, often automatically and possibly without further user intervention, the sequence analysis and derivation of aneuploidy operation. In some implementations, the result of this processing operation is then automatically delivered, possibly with reformatting as a diagnosis, to a system component or entity that processes reports the information to a health professional and/or patient. As explained such information can also be automatically processed to produce a treatment, testing, and/or monitoring plan, possibly along with counseling information. Thus, initiating an early stage operation can trigger an end to end sequence in which the health professional, patient or other concerned party is provided with a diagnosis, a plan, counseling and/or other information useful for acting on a physical condition. This is accomplished even though parts of the overall system are physically separated and possibly remote from the location of, e.g., the sample and sequence apparatus.

Figure 5:
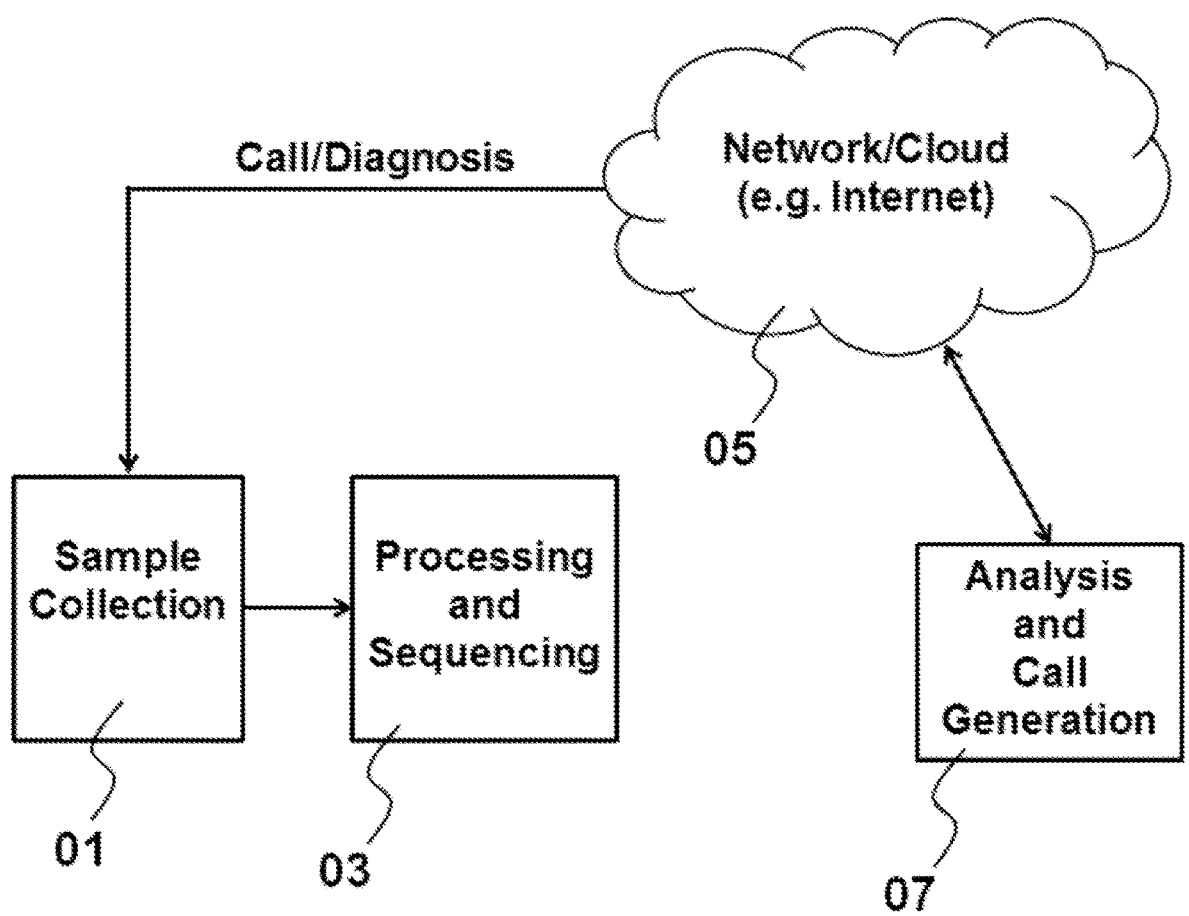
FIG. 5 is a block diagram of a dispersed system for processing a test sample and ultimately making a diagnosis.

FIG. 5 shows one implementation of a dispersed system for producing a call or diagnosis from a test sample. A sample collection location 01 is used for obtaining a test sample from a patient such as a pregnant female or a putative cancer patient. The samples then provided to a processing and sequencing location 03 where the test sample may be processed and sequenced as described above. Location 03 includes apparatus for processing the sample as well as apparatus for sequencing the processed sample. The result of the sequencing, as described elsewhere herein, is a collection of reads which are typically provided in an electronic format and provided to a network such as the Internet, which is indicated by reference number 05 in FIG. 5.

The sequence data is provided to a remote location 07 where analysis and call generation are performed. This location may include one or more powerful computational devices such as computers or processors. After the computational resources at location 07 have completed their analysis and generated a call from the sequence information received, the call is relayed back to the network 05. In some implementations, not only is a call generated at location 07 but an associated diagnosis is also generated. The call and or diagnosis are then transmitted across the network and back to the sample collection location 01 as illustrated in FIG. 5. As explained, this is simply one of many variations on how the various operations associated with generating a call or diagnosis may be divided among various locations. One common variant involves providing sample collection and processing and sequencing in a single location. Another variation involves providing processing and sequencing at the same location as analysis and call generation.

Figure 6:
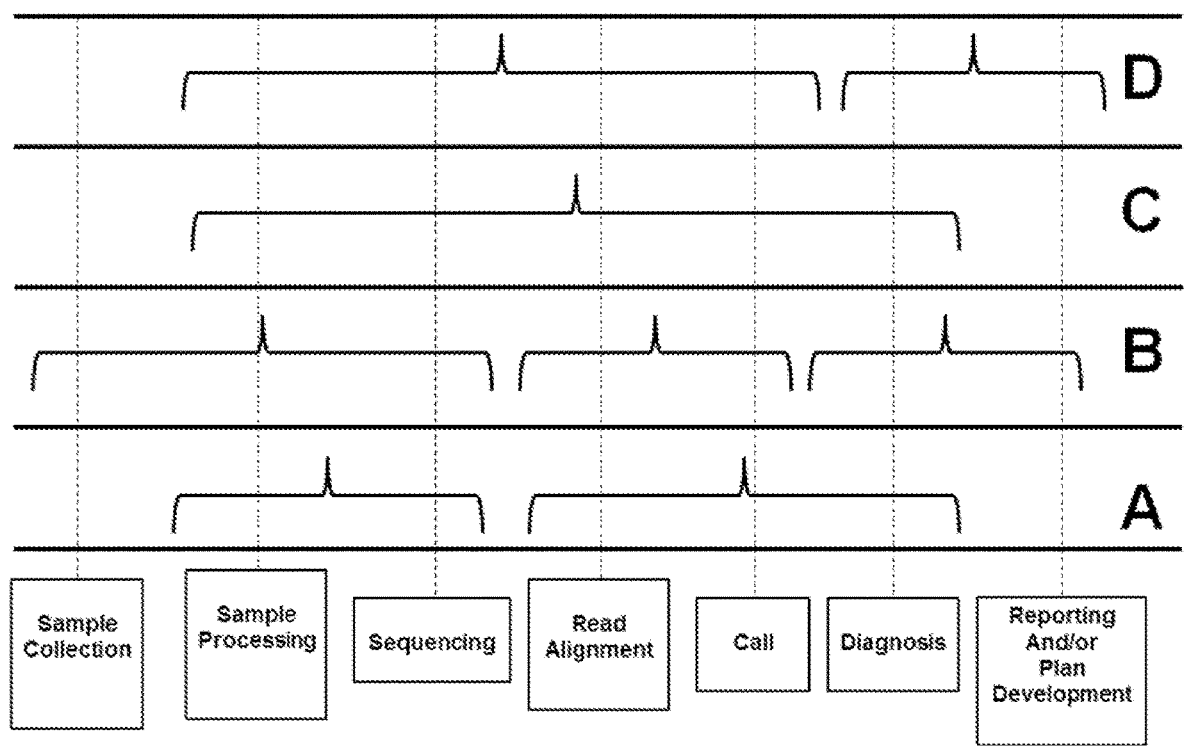
FIG. 6 schematically illustrates how different operations in processing test samples may be grouped to be handled by different elements of a system.

FIG. 6 elaborates on the options for performing various operations at distinct locations. In the most granular sense depicted in FIG. 6, each of the following operations is performed at a separate location: sample collection, sample processing, sequencing, read alignment, calling, diagnosis, and reporting and/or plan development.

In one embodiment that aggregates some of these operations, sample processing and sequencing are performed in one location and read alignment, calling, and diagnosis are performed at a separate location. See the portion of FIG. 6 identified by reference character A. In another implementation, which is identified by character B in FIG. 6, sample collection, sample processing, and sequencing are all performed at the same location. In this implementation, read alignment and calling are performed in a second location. Finally, diagnosis and reporting and/or plan development are performed in a third location. In the implementation depicted by character C in FIG. 6, sample collection is performed at a first location, sample processing, sequencing, read alignment, calling, and diagnosis are all performed together at a second location, and reporting and/or plan development are performed at a third location. Finally, in the implementation labeled D in FIG. 6, sample collection is performed at a first location, sample processing, sequencing, read alignment, and calling are all performed at a second location, and diagnosis and reporting and/or plan management are performed at a third location.

One embodiment provides a system for use in determining the presence or absence of any one or more different complete fetal chromosomal aneuploidies in a maternal test sample comprising fetal and maternal nucleic acids, the system including a sequencer for receiving a nucleic acid sample and providing fetal and maternal nucleic acid sequence information from the sample; a processor; and a machine readable storage medium comprising instructions for execution on said processor, the instructions comprising:
(a) code for obtaining sequence information for said fetal and maternal nucleic acids in the sample;
(b) code for using said sequence information to computationally identify a number of sequence tags from the fetal and maternal nucleic acids for each of any one or more chromosomes of interest selected from chromosomes 1-22, X, and Y and to identify a number of sequence tags for at least one normalizing chromosome sequence or normalizing chromosome segment sequence for each of said any one or more chromosomes of interest;
(c) code for using said number of sequence tags identified for each of said any one or more chromosomes of interest and said number of sequence tags identified for each normalizing chromosome sequence or normalizing chromosome segment sequence to calculate a single chromosome dose for each of the any one or more chromosomes of interest; and
(d) code for comparing each of the single chromosome doses for each of the any one or more chromosomes of interest to a corresponding threshold value for each of the one or more chromosomes of interest, and thereby determining the presence or absence of any one or more complete different fetal chromosomal aneuploidies in the sample.

In some embodiments, the code for calculating a single chromosome dose for each of the any one or more chromosomes of interest comprises code for calculating a chromosome dose for a selected one of the chromosomes of interest as the ratio of the number of sequence tags identified for the selected chromosome of interest and the number of sequence tags identified for a corresponding at least one normalizing chromosome sequence or normalizing chromosome segment sequence for the selected chromosome of interest.

In some embodiments, the system further comprises code for repeating the calculating of a chromosome dose for each of any remaining chromosome segments of the any one or more segments of any one or more chromosomes of interest.

In some embodiments, the one or more chromosomes of interest selected from chromosomes 1-22, X, and Y comprise at least twenty chromosomes selected from chromosomes 1-22, X, and Y, and wherein the instructions comprise instructions for determining the presence or absence of at least twenty different complete fetal chromosomal aneuploidies is determined.

In some embodiments, the at least one normalizing chromosome sequence is a group of chromosomes selected from chromosomes 1-22, X, and Y. In other embodiments, the at least one normalizing chromosome sequence is a single chromosome selected from chromosomes 1-22, X, and Y.

Another embodiment provides a system for use in determining the presence or absence of any one or more different partial fetal chromosomal aneuploidies in a maternal test sample comprising fetal and maternal nucleic acids, the system comprising: a sequencer for receiving a nucleic acid sample and providing fetal and maternal nucleic acid sequence information from the sample; a processor; and a machine readable storage medium comprising instructions for execution on said processor, the instructions comprising:
(a) code for obtaining sequence information for said fetal and maternal nucleic acids in said sample;
(b) code for using said sequence information to computationally identify a number of sequence tags from the fetal and maternal nucleic acids for each of any one or more segments of any one or more chromosomes of interest selected from chromosomes 1-22, X, and Y and to identify a number of sequence tags for at least one normalizing segment sequence for each of said any one or more segments of any one or more chromosomes of interest;
(c) code using said number of sequence tags identified for each of said any one or more segments of any one or more chromosomes of interest and said number of sequence tags identified for said normalizing segment sequence to calculate a single chromosome segment dose for each of said any one or more segments of any one or more chromosomes of interest; and
(d) code for comparing each of said single chromosome segment doses for each of said any one or more segments of any one or more chromosomes of interest to a corresponding threshold value for each of said any one or more chromosome segments of any one or more chromosome of interest, and thereby determining the presence or absence of one or more different partial fetal chromosomal aneuploidies in said sample.

In some embodiments, the code for calculating a single chromosome segment dose comprises code for calculating a chromosome segment dose for a selected one of the chromosome segments as the ratio of the number of sequence tags identified for the selected chromosome segment and the number of sequence tags identified for a corresponding normalizing segment sequence for the selected chromosome segment.

In some embodiments, the system further comprises code for repeating the calculating of a chromosome segment dose for each of any remaining chromosome segments of the any one or more segments of any one or more chromosomes of interest.

In some embodiments, the system further comprises (i) code for repeating (a)-(d) for test samples from different maternal subjects, and (ii) code for determining the presence or absence of any one or more different partial fetal chromosomal aneuploidies in each of said samples.

In other embodiments of any of the systems provided herein, the code further comprises code for automatically recording the presence or absence of a fetal chromosomal aneuploidy as determined in (d) in a patient medical record for a human subject providing the maternal test sample, wherein the recording is performed using the processor.

In some embodiments of any of the systems provided herein, the sequencer is configured to perform next generation sequencing (NGS). In some embodiments, the sequencer is configured to perform massively parallel sequencing using sequencing-by-synthesis with reversible dye terminators. In other embodiments, the sequencer is configured to perform sequencing-by-ligation. In yet other embodiments, the sequencer is configured to perform single molecule sequencing.

EXPERIMENTAL

Example 1

Preparation and Sequencing of Primary and Enriched Sequencing Libraries a. Preparation of Sequencing Libraries—Abbreviated Protocol (ABB)

All sequencing libraries, i.e., primary and enriched libraries, were prepared from approximately 2 ng of purified cfDNA that was extracted from maternal plasma. Library preparation was performed using reagents of the NEBNext™ DNA Sample Prep DNA Reagent Set 1 (Part No. E6000L; New England Biolabs, Ipswich, Mass.), for Illumina® as follows. Because cell-free plasma DNA is fragmented in nature, no further fragmentation by nebulization or sonication was done on the plasma DNA samples. The overhangs of approximately 2 ng purified cfDNA fragments contained in 40 µl were converted into phosphorylated blunt ends according to the NEBNext® End Repair Module by incubating in a 1.5 ml microfuge tube the cfDNA with 5 µl 10× phosphorylation buffer, 2 µl deoxynucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 for 15 minutes at 20° C. The enzymes were then heat inactivated by incubating the reaction mixture at 75° C. for 5 minutes. The mixture was cooled to 4° C., and dA tailing of the blunt-ended DNA was accomplished using 10 µl of the dA-tailing master mix containing the Klenow fragment (3' to 5' exo minus) (NEBNext™ DNA Sample Prep DNA Reagent Set 1), and incubating for 15 minutes at 37° C. Subsequently, the Klenow fragment was heat inactivated by incubating the reaction mixture at 75° C. for 5 minutes. Following the inactivation of the Klenow fragment, 1 µl of a 1:5 dilution of Illumina Genomic Adaptor Oligo Mix (Part No. 1000521; Illumina Inc., Hayward, Calif.) was used to ligate the Illumina adaptors (Non-Index Y-Adaptors) to the dA-tailed DNA using 4 µl of the T4 DNA ligase provided in the NEBNext™ DNA Sample Prep DNA Reagent Set 1, by incubating the reaction mixture for 15 minutes at 25° C. The mixture was cooled to 4° C., and the adaptor-ligated cfDNA was purified from unligated adaptors, adaptor dimers, and other reagents using magnetic beads provided in the Agencourt AMPure XP PCR purification system (Part No. A63881; Beckman Coulter Genomics, Danvers, Mass.). Eighteen cycles of PCR were performed to selectively enrich adaptor-ligated cfDNA (25 µl) using Phusion® High-Fidelity Master Mix (25 µl; Finnzymes, Woburn, Mass.) and Illumina's PCR primers (0.5 µM each) complementary to the adaptors (Part No. 1000537 and 1000537). The adaptor-ligated DNA was subjected to PCR (98° C. for 30 seconds; 18 cycles of 98° C. for 10 seconds, 65° C. for 30 seconds, and 72° C. for 30; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, Mass.) according to the manufacturer's instructions available at www.beckmangenomics.com/products/AMPureXPProtocol_000387v001.pdf. The purified amplified product was eluted in 40 µl of Qiagen EB Buffer, and the concentration and size distribution of the amplified libraries was analyzed using the Agilent DNA 1000 Kit for the 2100 Bioanalyzer (Agilent technologies Inc., Santa Clara, Calif.).

b. Preparation of Sequencing Libraries—Full-Length Protocol

The full-length protocol described here is essentially the standard protocol provided by Illumina, and only differs from the Illumina protocol in the purification of the amplified library. The Illumina protocol instructs that the amplified library be purified using gel electrophoresis, while the protocol described herein uses magnetic beads for the same purification step. Approximately 2 ng of purified cfDNA extracted from maternal plasma was used to prepare a primary sequencing library using NEBNext™ DNA Sample Prep DNA Reagent Set 1 (Part No. E6000L; New England Biolabs, Ipswich, Mass.) for Illumina® essentially according to the manufacturer's instructions. All steps except for the final purification of the adaptor-ligated products, which was performed using Agencourt magnetic beads and reagents instead of the purification column, were performed according to the protocol accompanying the NEBNext™ Reagents for Sample Preparation for a genomic DNA library that is sequenced using the Illumina® GAIL The NEBNext™ protocol essentially follows that provided by Illumina, which is available at grcf.jhml.edu/hts/protocols/11257047_ChIP_Sample_Prep.pdf.

Figure 7A:
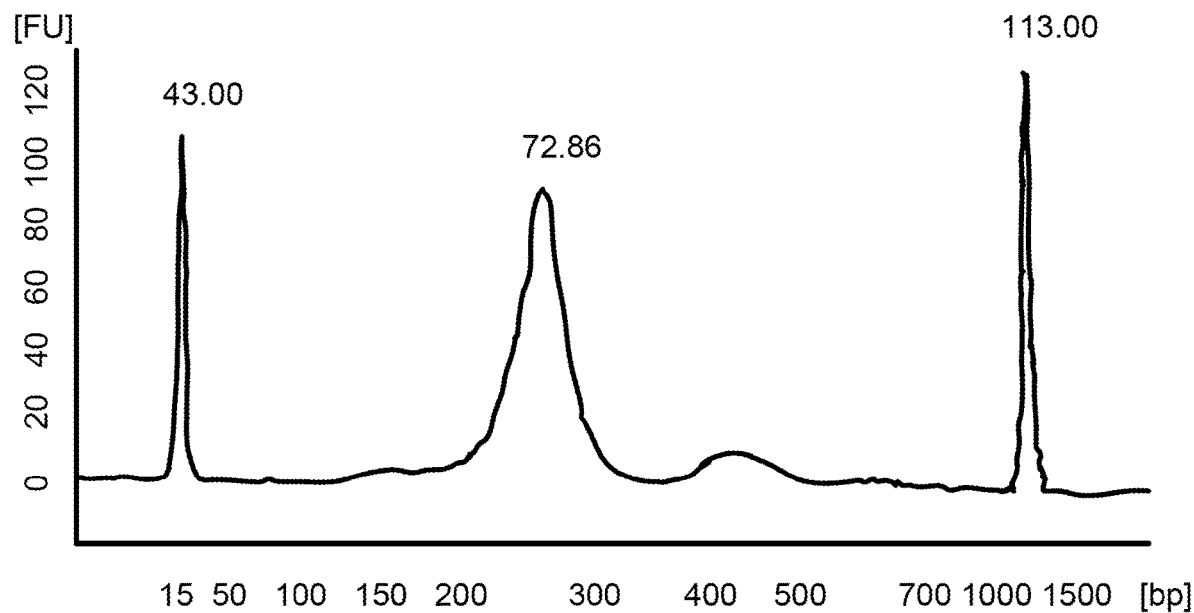
FIGS. 7A and 7B shows electropherograms of a cfDNA sequencing library prepared according to the abbreviated protocol described in Example 1a (FIG. 7A), and the protocol described in Example 1b (FIG. 7B).
Figure 7B:
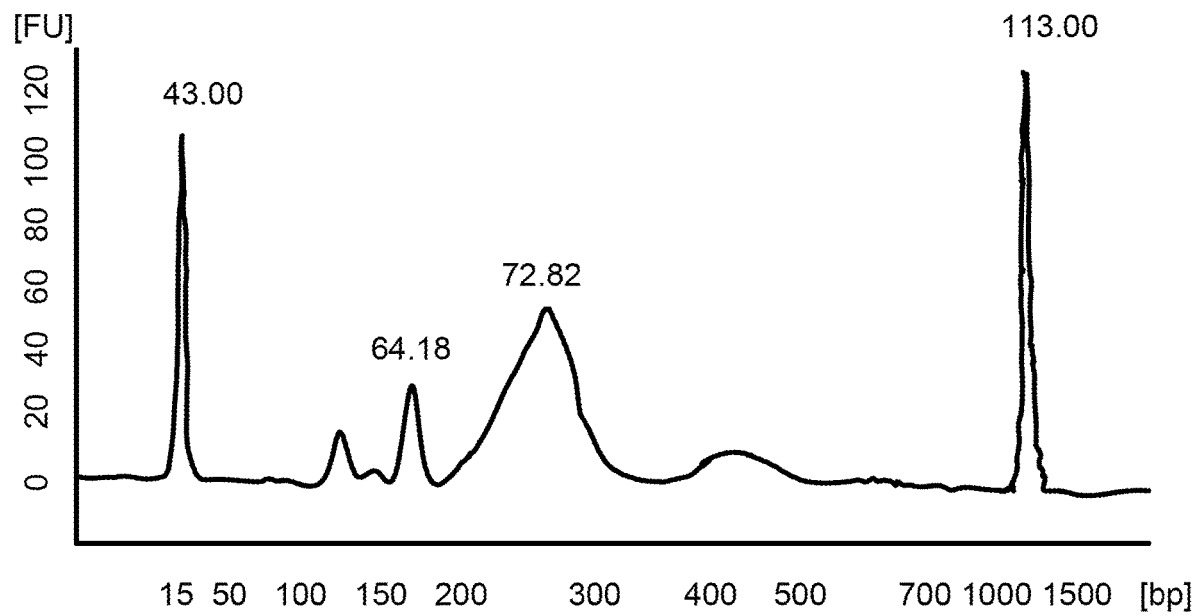

The overhangs of approximately 2 ng purified cfDNA fragments contained in 40 µl were converted into phosphorylated blunt ends according to the NEBNext® End Repair Module by incubating the 40 µl cfDNA with 5 µl 10× phosphorylation buffer, 2 µl deoxynucleotide solution mix (10 mM each dNTP), 1 µl of a 1:5 dilution of DNA Polymerase I, 1 µl T4 DNA Polymerase and 1 µl T4 Polynucleotide Kinase provided in the NEBNext™ DNA Sample Prep DNA Reagent Set 1 in a 200 µl microfuge tube in a thermal cycler for 30 minutes at 20° C. The sample was cooled to 4° C., and purified using a QIAQuick column provided in the QIAQuick PCR Purification Kit (QIAGEN Inc., Valencia, Calif.) as follows. The 50 µl reaction was transferred to 1.5 ml microfuge tube, and 250 µl of Qiagen Buffer PB were added. The resulting 300 µl were transferred to a QIAquick column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 39 µl Qiagen Buffer EB by centrifugation. dA tailing of 34 µl of the blunt-ended DNA was accomplished using 16 µl of the dA-tailing master mix containing the Klenow fragment (3' to 5' exo minus) (NEBNext™ DNA Sample Prep DNA Reagent Set 1), and incubating for 30 minutes at 37° C. according to the manufacturer's NEBNext® dA-Tailing Module. The sample was cooled to 4° C., and purified using a column provided in the MinElute PCR Purification Kit (QIAGEN Inc., Valencia, Calif.) as follows. The 50 µl reaction was transferred to 1.5 ml microfuge tube, and 250 µl of Qiagen Buffer PB were added. The 300 µl were transferred to the MinElute column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 15 µl Qiagen Buffer EB by centrifugation. Ten microliters of the DNA eluate were incubated with 1 µl of a 1:5 dilution of the Illumina Genomic Adapter Oligo Mix (Part No. 1000521), 15 µl of 2× Quick Ligation Reaction Buffer, and 4 µl Quick T4 DNA Ligase, for 15 minutes at 25° C. according to the NEBNext® Quick Ligation Module. The sample was cooled to 4° C., and purified using a MinElute column as follows. One hundred and fifty microliters of Qiagen Buffer PE were added to the 30 µl reaction, and the entire volume was transferred to a MinElute column were transferred to a MinElute column, which was centrifuged at 13,000 RPM for 1 minute in a microfuge. The column was washed with 750 µl Qiagen Buffer PE, and re-centrifuged. Residual ethanol was removed by an additional centrifugation for 5 minutes at 13,000 RPM. The DNA was eluted in 28 µl Qiagen Buffer EB by centrifugation. Twenty three microliters of the adaptor-ligated DNA eluate were subjected to 18 cycles of PCR (98° C. for 30 seconds; 18 cycles of 98° C. for 10 seconds, 65° C. for 30 seconds, and 72° C. for 30; final extension at 72° C. for 5 minutes, and hold at 4° C.) using Illumina Genomic PCR Primers (Part Nos. 100537 and 1000538) and the Phusion HF PCR Master Mix provided in the NEBNext™ DNA Sample Prep DNA Reagent Set 1, according to the manufacturer's instructions. The amplified product was purified using the Agencourt AMPure XP PCR purification system (Agencourt Bioscience Corporation, Beverly, Mass.) according to the manufacturer's instructions available at www.beckmangenomics.com/products/AMPureXPProtocol_000387v001.pdf. The Agencourt AMPure XP PCR purification system removes unincorporated dNTPs, primers, primer dimers, salts and other contaminates, and recovers amplicons greater than 100 bp. The purified amplified product was eluted from the Agencourt beads in 40 µl of Qiagen EB Buffer and the size distribution of the libraries was analyzed using the Agilent DNA 1000 Kit for the 2100 Bioanalyzer (Agilent technologies Inc., Santa Clara, Calif.).

c. Analysis of Sequencing Libraries Prepared According to the Abbreviated (a) and the Full-Length (b) Protocols The electropherograms generated by the Bioanalyzer are shown in FIGS. 7A and 7B. FIG. 7A shows the electropherogram of library DNA prepared from cfDNA purified from plasma sample M24228 using the full-length protocol described in (a), and FIG. 7B shows the electropherogram of library DNA prepared from cfDNA purified from plasma sample M24228 using the full-length protocol described in (b). In both figures, peaks 1 and 4 represent the 15 bp Lower Marker, and the 1,500 Upper Marker, respectively; the numbers above the peaks indicate the migration times for the library fragments; and the horizontal lines indicate the set threshold for integration. The electropherogram in FIG. 7A shows a minor peak of fragments of 187 bp and a major peak of fragments of 263 bp, while the electropherogram in FIG. 7B shows only one peak at 265 bp. Integration of the peak areas resulted in a calculated concentration of 0.40 ng/µl for the DNA of the 187 bp peak in FIG. 7A, a concentration of 7.34 ng/µl for the DNA of the 263 bp peak in FIG. 7A, and a concentration of 14.72 ng/µl for the DNA of the 265 bp peak in FIG. 7B. The Illumina adaptors that were ligated to the cfDNA are known to be 92 bp, which when subtracted from the 265 bp, indicate that the peak size of the cfDNA is 173 bp. It is possible that the minor peak at 187 bp represents fragments of two primers that were ligated end-to-end. The linear two-primer fragments are eliminated from the final library product when the abbreviated protocol is used. The abbreviated protocol also eliminates other smaller fragments of less than 187 bp. In this example, the concentration of purified adaptor-ligated cfDNA is double that of the adaptor-ligated cfDNA produced using the full-length protocol. It has been noted that the concentration of the adaptor-ligated cfDNA fragments was always greater than that obtained using the full-length protocol (data not shown).

Thus, an advantage of preparing the sequencing library using the abbreviated protocol is that the library obtained consistently comprises only one major peak in the 262-267 bp range while the quality of the library prepared using the full-length protocol varies as reflected by the number and mobility of peaks other than that representing the cfDNA. Non-cfDNA products would occupy space on the flow cell and diminish the quality of the cluster amplification and subsequent imaging of the sequencing reactions, which underlies the overall assignment of the aneuploidy status. The abbreviated protocol was shown not to affect the sequencing of the library.

Another advantage of preparing the sequencing library using the abbreviated protocol is that the three enzymatic steps of blunt-ending, d-A tailing, and adaptor-ligation, take less than an hour to complete to support the validation and implementation of a rapid aneuploid diagnostic service.

Another advantage is that the three enzymatic steps of blunt-ending, d-A tailing, and adaptor ligation, are performed in the same reaction tube, thus avoiding multiple sample transfers that would potentially lead to loss of material, and more importantly to possible sample mix-up and sample contamination.

Example 2

Accurate Aneuploidy Detection in Twin Pregnancies

Introduction

Non-invasive prenatal testing (NIPT) of total cell free DNA (cfDNA) using whole-genome massively parallel sequencing has been shown to be a very accurate and robust method of detecting fetal chromosome aneuploidies. See, Bianchi D W, Platt L D, Goldberg J D, et al. Genome-wide fetal aneuploidy detection by maternal plasma DNA sequencing. Obstet Gynecol 2012; 119:890-901; Fan H C, Blumenfeld Y J, Chitkara U, Hudgins L, Quake S R. Noninvasive diagnosis of fetal aneuploidy by shotgun sequencing DNA from maternal blood. Proc Natl Acad Sci USA 2008; 105:16266-71; Sehnert A J, Rhees B, Comstock D, et al. Optimal detection of fetal chromosomal abnormalities by massively parallel DNA sequencing of cell-free fetal DNA from maternal blood. Clin Chem 2011; 57:1042-9. The instant test detects trisomy 21, 18, 13 and sex chromosome aneuploidies from a single maternal blood sample. The instant test is currently indicated for pregnant women with singleton gestation at 10+ weeks, and at high-risk for fetal aneuploidy. Recently, the American College of Obstetricians and Gynecologists (ACOG), the International Society for Prenatal Diagnosis (ISPD), the American College of Medical Genetics and Genomics (ACMG) and the National Society of Genetic Counselors (NSGC) have recommended considering the use of NIPT for women with a high risk of fetal aneuploidy.

In the United States, twins account for approximately one in 30 live births and the rate of twin births is on the increase (National Center for Health Statistics Data Brief, No. 80, January 2012). As women age, they are more likely to release more than one egg per menstrual cycle and, as such, women over 30 account for about ⅓ of the increase in twin pregnancies. Assisted reproduction techniques, where often more than one embryo is transferred during in vitro fertilization, account for the majority of the remaining increase in twin pregnancies.

Preliminary evidence suggests that the amount of fetal DNA present in maternal circulation increases approximately 35% in twin pregnancies when compared to singleton pregnancies but the study did not look at the amount of cfDNA derived from each fetus. Canick J A, Kloza E M, Lambert-Messerlian G M, et al. DNA sequencing of maternal plasma to identify Down syndrome and other trisomies in multiple gestations. Prenat Diagn 2012; 32:730-4. Researchers have demonstrated that although there is an overall increase in the amount of circulating fetal DNA in twin pregnancies, the amount of cfDNA for each fetus decreases. Srinivasan A, Bianchi D, Liao W, Sehnert A, Rava R. 52: Maternal plasma DNA sequencing: effects of multiple gestation on aneuploidy detection and the relative cell-free fetal DNA (cffDNA) per fetus. American journal of obstetrics and gynecology 2013; 208:S31. Srinivasan A, Bianchi D W, Huang H, Sehnert A J, Rava R P. Noninvasive detection of fetal subchromosome abnormalities via deep sequencing of maternal plasma. American journal of human genetics 2013; 92:167-76. Therefore, sensitive methodologies are required to insure correct classification of aneuploidy in twin pregnancies.

Factors that maximize the ability of NIPT to accurately classify aneuploidy samples are an increase in the number of sequencing reads used in the analysis so the statistical noise is minimized and the ability to normalize chromosomal signals such that inter-run variability is reduced. Recently, applicant has developed an improved, automated sample preparation workflow that increases the number of usable reads per sample and an improved analytical methodology that increases the specific signal of aneuploid chromosomes. These enhancements improve the overall accuracy of classifying aneuploid affected samples.

This example describes the application of an improved classification algorithm to the largest twin validation cohort used to date. We demonstrate that an improved SAFeR (Selective Algorithm for Fetal Results) algorithm allows for accurate aneuploidy detection in twin samples, which are known to have a reduced amount of cell free DNA per fetus.

Methods

Samples were collected as part of two independent clinical studies involving both high risk and average risk maternal populations. The MatErnal BLood IS Source to Accurately Diagnose Fetal Aneuploidy study (MELISSA; NCT01122524) was designed to detect whole chromosome aneuploidies in high-risk pregnancies. Bianchi D W, Platt L D, Goldberg J D, et al. Genome-wide fetal aneuploidy detection by maternal plasma DNA sequencing. Obstet Gynecol 2012; 119:890-901. The Comparison of Aneuploidy Risk Evaluations trial (CARE; NCT01663350) was designed to demonstrate a superior specificity of the instant test compared to conventional prenatal serum screening methods for trisomy 21 and trisomy 18 in an average risk maternal population (submitted for publication). Details of the dataset are shown in Table 2. Clinical outcomes were determined either by karyotype from a prenatal invasive procedure or by newborn physical examination.

TABLE 2

Karyotype and instant classification of twin samples. Maternal samples from 118 twin pregnancies were analyzed using the instant prenatal test for aneuploidies of chromosomes 21, 18 and 13 and for the presence of the Y chromosome. The instant data was compared with clinical outcomes determined by either karyotype analysis or newborn physical examination.

| Number studied | Fetus 1 | Fetus 2 | instant aneuploidy classification | instant chromosome Y classification |
|---|---|---|---|---|
| 24 | 46, XX | 46, XX | Not affected | Not detected |
| 48 | 46, XX | 46, XY | Not affected | Y Detected |
| 42 | 46, XY | 46, XY | Not affected | Y Detected |
| 2 | 47, XY, +21 | 46, XY | T21 affected | Y Detected |
| 1 | Mos 47, XY, +21[7]/ 46, XY[11] | 46, XX | T21 affected | Y Detected |
| 1 | 47, XY, +18 | 47, XY, +18 | T18 affected | Y Detected |

Cell-free DNA was extracted from frozen plasma samples and sequenced on HiSeq2000 sequencers as described previously. Sehnert A J, Rhees B, Comstock D, et al. Optimal detection of fetal chromosomal abnormalities by massively parallel DNA sequencing of cell-free fetal DNA from maternal blood. Clin Chem 2011; 57:1042-9. Massive Parallel Sequencing (MPS) sequence tags were mapped to the human genome reference build hg19 and Normalized Chromosome Values (NCVs) were calculated for chromosomes 21, 18, 13, X and Y using an improved analytical workflow that maximized signal to noise ratio and improved the overall sensitivity of detection. The algorithmic components included improved genomic filtering, removal of systematic biases introduced through the molecular biology steps and improved normalization and classification methods. Laboratory personnel who carried out the sequencing were blinded to the clinical outcome.

Results

Figure 8:
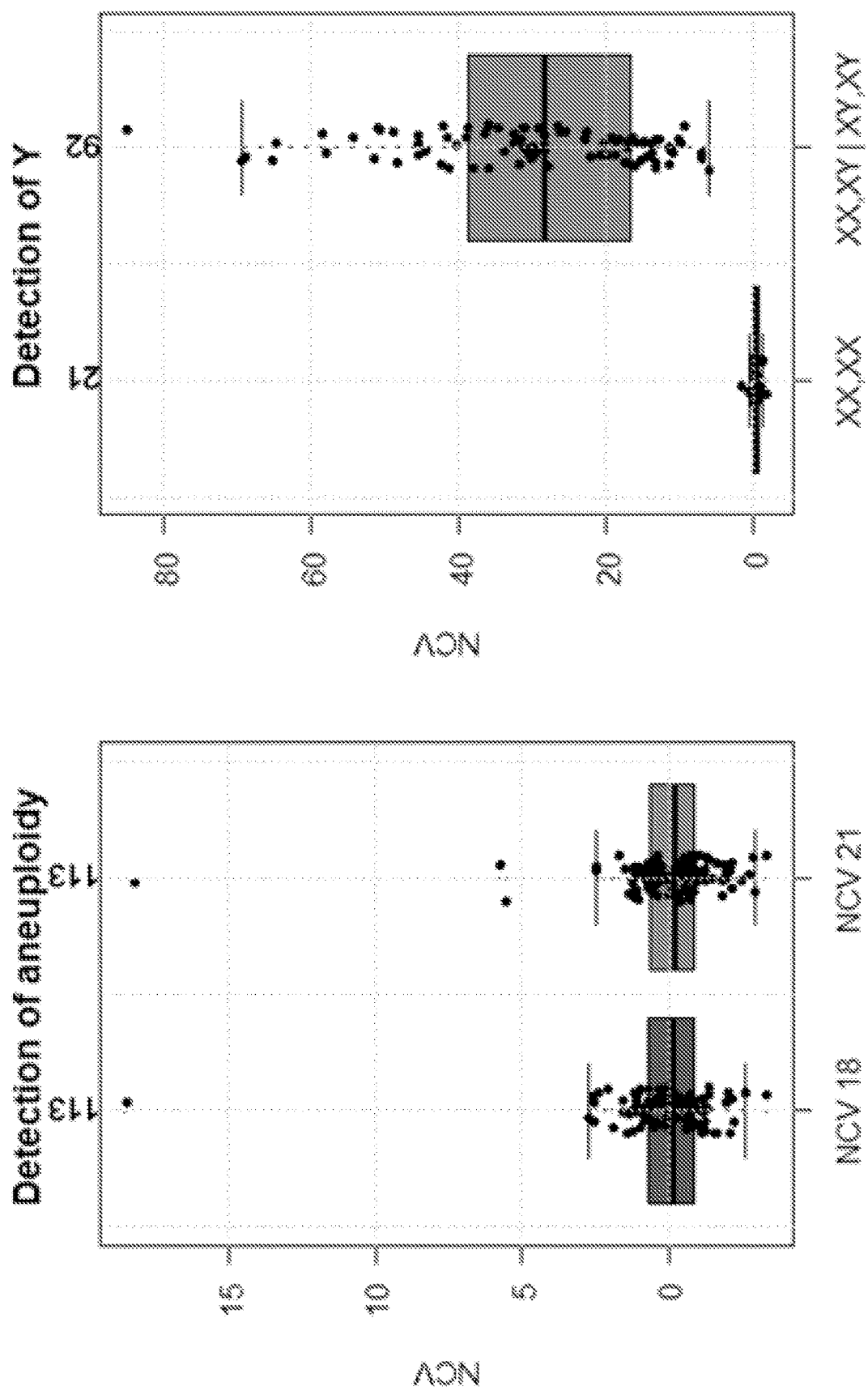
FIG. 8 shows Normalized Chromosome Value (NCV) distributions for maternal plasma samples from 118 twin pregnancies. (A) NCV distributions for chromosomes 21 and 18; three samples were classified as T21 affected (including a fetus that was mosaic for T21) and one sample was classified as T18 affected. (B) NCV distribution for chromosome Y. The cohort was split into samples that were clinically classified as female/female or samples that contained at least one male fetus (male/female and male/male) and the presence of the Y chromosome was determined using the NCV for chromosome Y.

Maternal plasma samples from 118 twin pregnancies with clinically defined outcomes were investigated in this study (Table 3). Aneuploidy classifications for chromosomes 21, 18 and 13 were generated for all of the samples in the study and four samples from pregnancies with one or more aneuploidy fetuses were correctly identified (FIG. 8). Two of these samples were from dichorionic twin pairs each with one T21 affected male fetus and one non-affected male fetus (47,XY+21/46,XY); one was a monochorionic twin sample with a 47,XY+18 karyotype; and one sample was dichorionic twins where one twin had the mosaic karyotype 47,XY+T21[7]/46,XY[11]. None of the clinically-defined unaffected samples (N=114) in this study were classified as affected for aneuploidy.

The sex of the fetuses can be determined by the presence of the Y chromosome in cfDNA. The test disclosed herein was able to positively identify the presence of the Y chromosome in all samples that had at least one male fetus (FIG. 8). Furthermore, the test also correctly identified the absence of the Y chromosome in samples with two female fetuses.

CONCLUSIONS

Figure 9:
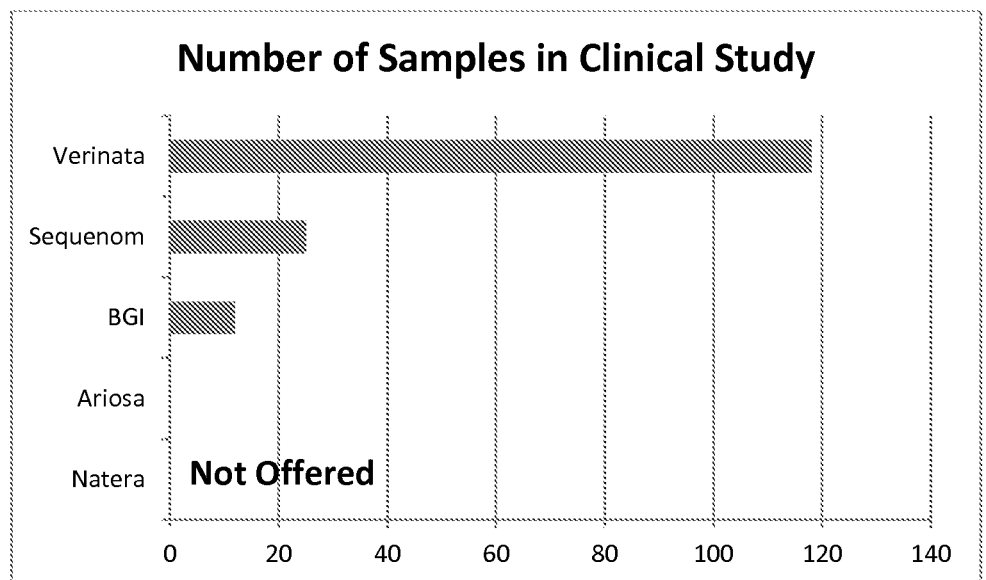
FIG. 9 shows twin samples analyzed in NIPT Studies. Number of twin samples used in various studies to assess the performance of commercially available NIPT tests.

The current study demonstrates an improved analytical methodology that enables the most sensitive autosomal aneuploidy testing of twin samples. The enhanced analytical method takes advantage of improvements in genome filtering, systematic noise reduction and improved classification methods. The utility of the improved analytical workflow was demonstrated on a set of 118 twin samples; the largest number of samples used in any validation of MPS to detect autosomal aneuploidies and presence of the Y chromosome in twins (FIG. 9). FIG. 9 shows twin samples analyzed in NIPT Studies. Number of twin samples used in various studies to assess the performance of commercially available NIPT tests. Canick J A, Kloza E M, Lambert-Messerlian G M, et al. DNA sequencing of maternal plasma to identify Down syndrome and other trisomies in multiple gestations. Prenat Diagn 2012; 32:730-4. Lau T K, Jiang F, Chan M K, Zhang H, Lo P S S, Wang W. Non-invasive prenatal screening of fetal Down syndrome by maternal plasma DNA sequencing in twin pregnancies. Journal of Maternal-Fetal and Neonatal Medicine 2013; 26:434-7. The improved analytical method was shown to perform accurately by correctly detecting the presence of all trisomy 21 and trisomy 18 samples in the cohort, including an affected fetus that was mosaic for trisomy 21, without generating any false positives results. Additionally, the improved analytical method correctly detected the presence of the Y chromosome in all twin pregnancies that had at least one male fetus and did not detect the Y chromosome in any of the twin pregnancies that had two female fetuses.

One characteristic of a sensitive method is the ability to minimize systematic noise and increase the overall signal to noise ratio. The current study accomplished this by producing more sequencing reads per sample than any of the other commercially-available NIPT assays (approximately 28M sequencing reads/sample) and by improving the analytical methodology to better handle the systematic noise that comes with biochemical manipulation of complex DNA samples. The improved analytical workflow ultimately reduces the width of the normalized chromosomal count distribution allowing a better separation of the unaffected and affected populations and an improved capability to accurately identify aneuploidy affected fetuses with low amounts of fetal DNA.

The ability to have a very accurate and sensitive methodology to detect aneuploidy in twin pregnancies is important because although the total amount of cell free fetal DNA increases in twin pregnancies, the amount attributable to each fetus decreases. Therefore, one can A) ignore this finding and test samples as if they were equivalent to singleton pregnancies and increase the likelihood of false negative results, B) reject an increased number of samples due to insufficient DNA or C) build a more sensitive methodology (Table 3).

Table 3: Strategies for Processing Twin Pregnancies Using Commercially Available NIPT Tests

| | Options | Results |
|---|---|---|
| A | Test twin pregnancies as if the cfDNA present were identical to singleton pregnancies. | Increased likelihood of false negatives. |
| B | Use current methodology to test twin pregnancies. | Reject samples due to insufficient DNA |
| C | Use an improved methodology that is more sensitive to individual cfDNA concentrations | More accurate testing for twins and low-level singletons with fewer false negatives. |

The analytical improvements to the SAFeR™ algorithm extend beyond enabling accurate aneuploidy classification in twin pregnancies. An improved separation of unaffected and affected populations also reduces the overall frequency of samples that are classified as aneuploidy suspected. Additionally, the improved analytical workflow can be applied to singleton pregnancies with similar improvements in aneuploidy detection and sex classification.

In conclusion, the current study describes an improved analytical method that leads to better separation of aneuploidy unaffected and affected samples and more accurate autosomal aneuploidy classifications from samples containing low amounts of fetal DNA. By incorporating these improvements the capabilities of the prenatal test have been expanded to test twin gestations.

The present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope

What is claimed is:

1. A method, implemented at a computer system that includes one or more processors and system memory, for evaluation of copy number of a nucleic acid sequence of interest in a test sample, the method comprising:
   (a) providing, at the computer system, at least 10,000 sequence reads obtained by a nucleic acid sequencer from the test sample, which test sample comprises nucleic acid molecules from one or more genomes;
   (b) aligning, by the computer system, the at least 10,000 sequence reads of the test sample to a reference genome comprising the nucleic acid sequence of interest, thereby providing test sequence tags;
   (c) determining, by the computer system, a coverage of the test sequence tags located in each bin, wherein each chromosome of the reference genome is divided into a plurality of bins, and wherein the coverage indicates a quantity of sequence tags in a bin;
   (d) providing, by the computer system, a global profile for the nucleic acid sequence of interest, wherein the global profile comprises an expected coverage in each bin, and wherein the expected coverage is obtained from a training set of training samples unaffected by a copy number variation of the nucleic acid sequence of interest, the expected coverage exhibiting variation from bin to bin;
   (e) adjusting, by the computer system, the coverage of the test sequence tags in each bin of at least the nucleic acid sequence of interest using the expected coverage in each bin, thereby obtaining global-profile-corrected coverages for the nucleic acid sequence of interest;
   (f) adjusting, by the computer system, the global-profile-corrected coverages based on a relation between GC content levels of the test sample and the global-profile-corrected coverages of the test sample, thereby obtaining sample-GC-corrected coverages for the nucleic acid sequence of interest, wherein the adjusting is not based on GC-coverage relations of samples other than the test sample; and
   (g) evaluating, by the computer system, a copy number of the nucleic acid sequence of interest in the test sample based on the sample-GC-corrected coverages, wherein the sample-GC-corrected coverages improve a signal level and/or reduce a noise level for determining the copy number of the nucleic acid sequence of interest.

2. The method of claim 1, further comprising, before providing sequence reads, sequencing nucleic acids from the test sample using a sequencer, thereby generating the sequence reads.

3. The method of claim 2, further comprising combining marker nucleic acids with the test sample before sequencing the nucleic acids.

4. The method of claim 3, wherein the marker nucleic acids are selected from the group consisting of: naturally-occurring deoxyribonucleic acids, naturally-occurring ribonucleic acids, peptide nucleic acids (PNA), morpholino nucleic acid, locked nucleic acids, glycol nucleic acids, threose nucleic acids, and any combinations thereof.

5. The method of claim 1, wherein the sequence reads are obtained from sequences of cell-free DNA of a pregnant woman and cell-free DNA of a fetus carried by the pregnant woman.

6. The method of claim 1, further comprising applying a sequence mask that excludes from consideration coverages in masked bins.

7. The method of claim 6, wherein the sequence mask is obtained by a method comprising:
providing, at the computer system, a training set comprising sequence reads from a plurality of unaffected training samples;
aligning, by the computer system, the sequence reads of the training set to the reference genome, thereby providing training sequence tags for the training samples;
dividing, by the computer system, the reference genome into a plurality of bins;
determining, by the computer system, a coverage of training sequence tags in each bin for each training sample; and
creating, by the computer system, a sequence mask comprising unmasked and masked bins, wherein each masked bin has a distribution index exceeding a masking threshold, the distribution index relating to the distribution of coverages of the training samples.

8. The method of claim 7, further comprising, before creating a sequence mask, adjusting the coverage of the training sequence tags according to the expected coverage in each bin, thereby obtaining global-profile-corrected coverages of the training sequence tags in the bins, which are then used to create a sequence mask.

9. The method of claim 7, wherein the distribution index is mathematically related to the variance of the coverages of the training samples.

10. The method of claim 9, wherein the distribution index is a coefficient of variation.

11. The method of claim 6, wherein the masked bins on the nucleic acid sequence of interest have a first masking threshold and the masked bins on a normalizing sequence have a second masking threshold.

12. The method of claim 11, wherein the combination of the first masking threshold and the second masking threshold provides a sequence mask that results in a lower variation of coverage over a region including the sequence of interest in unaffected samples than sequence masks obtained using other thresholds.

13. The method of claim 6, wherein the sequence mask comprises masked bins and unmasked bins defined by the distribution of mapping quality scores across training samples within the bins, the mapping quality scores being derived from aligning sequence reads of a plurality of unaffected training samples to the reference genome.

14. The method of claim 1, wherein evaluating copy number of the nucleic acid sequence of interest in the test sample in operation (g) comprises calculating a sequence dose of the nucleic acid sequence of interest for the test sample using coverage information of a normalizing sequence.

15. The method of claim 14, wherein calculating the sequence dose comprises dividing the sample-GC-corrected coverage of the test sequence tags in the nucleic acid sequence of interest by the sample-GC-corrected coverage of the test sequence tags in a normalizing sequence.

16. The method claim 15, wherein the normalizing sequence comprises one or more robust autosomes sequences or segments thereof.

17. The method of claim 1, wherein evaluating the copy number of the nucleic acid sequence of interest in the test sample in operation (g) comprises calculating a normalized chromosome value or a normalized segment value of the nucleic acid sequence of interest for the test sample using coverage information of a normalizing sequence.

18. The method of claim 1, wherein the test sample comprises a mixture of nucleic acids from two different genomes.

19. The method of claim 18, wherein said nucleic acids comprise cell-free DNA molecules.

20. The method of claim 1, wherein the test sample comprises fetal and maternal cell-free nucleic acids.

21. The method of claim 1, wherein the test sample comprises fetal cell-free nucleic acids from two or more fetuses.

22. The method of claim 1, wherein the test sample comprises nucleic acids from cancerous and unaffected cells from the same subject.

23. The method of claim 1, wherein the evaluating copy number of the nucleic acid sequence of interest in the test sample comprises determining the presence or absence of a complete or partial fetal aneuploidy.

24. The method of claim 1, further comprising removing, after operation (f), outlier bins of sample-GC-corrected coverage from consideration in evaluation of copy number variation.

25. The method of claim 24, wherein the outlier bins comprises bins whose median sample-GC-corrected coverage are more than about 1 median absolute deviation from the median of all the bins.

26. The method of claim 1, wherein the expected coverage in each bin comprises a median or mean of coverages of training samples, and wherein the adjusting the coverage of the test sequence tags in operation (e) comprises dividing the coverage of the test sequence tags for each bin by the median or mean of coverages of training samples from the bin.

27. The method of claim 1, wherein adjusting the coverage of the test sequence tags in operation (e) comprises: (i) obtaining a relation between the coverage of the test sequence tags versus the expected coverage in a plurality of bins in one or more robust chromosomes or regions, and (ii) applying the relation to bins in the sequence of interest to obtain the global-profile-corrected coverages.

28. The method claim 27, wherein
the relation in (i) is a obtained by a linear regression:

$$y_a = \text{intercept} + \text{slope} * gwp_a,$$

wherein $y_a$ is coverage of bin a for the test sample in one or more robust chromosomes or regions, and $gwp_a$ is the global profile for bin a for unaffected training samples; and
obtaining the global-profile-corrected coverages in (ii) comprises obtaining the global-profile-corrected coverages $z_b$ as:

$$z_b = y_b / (\text{intercept} + \text{slope} * gwp_b) - 1$$

wherein $y_b$ is an observed coverage of bin b for the test sample in the sequence of interest, and $gwp_b$ is the global profile for bin b for unaffected training samples.

29. The method of claim 1, wherein the global-profile-corrected coverage of the test sequence tags from (e) comprise global-profile-corrected coverage of bins in the nucleic acid sequence of interest and global-profile-corrected coverage of bins in a normalizing sequence.

30. The method of claim 1, wherein adjusting the global-profile-corrected coverage in operation (f) comprises:
grouping bins in the reference genome into a plurality of GC groups, each GC group comprising multiple bins, wherein the multiple bins contain test sequence tags and have similar GC content;
determining an expected value of the global-profile-corrected coverage for each GC group for a plurality of robust autosomes; and
adjusting the global-profile-corrected coverage of the test sequence tags for each GC group based on the determined expected value of the same GC group, thereby obtaining the sample-GC-corrected coverage of the test sequence tags on the nucleic acid sequence of interest.

31. The method of claim 30, wherein the expected value of the global-profile-corrected coverage is the mean or the median of the coverage for the GC group of a plurality of robust autosomes.

32. The method of claim 30, wherein adjusting the global-profile-corrected coverage of the test sequence tags comprises subtracting the expected value from the global-profile-corrected coverage.

33. The method of claim 30, wherein the adjusting the global-profile-corrected coverage in operation (f) comprises:
fitting a linear or non-linear mathematical function to data points from a plurality of robust autosomes, wherein each data point relates a coverage value to a GC content value; and
adjusting the global-profile-corrected coverage of the test sequence tags in each bin based on an expected value of coverage for each bin, which equals to the coverage value of the mathematical function at the GC content value of the bin under consideration.

34. The method of claim 33, wherein adjusting the global-profile-corrected coverage of the test sequence tags comprises subtracting the expected value from the global-profile-corrected coverage.

35. The method of claim 1, further comprising extracting cell free DNA from a plurality of unaffected individuals and/or the test sample.

36. The method of claim 1, wherein the sequence reads comprise sequences of about 20 to 50-bp from anywhere in the entire genome of an individual.

37. The method of claim 1, wherein the sequence reads of (a) comprises bar-coded 25-mers.

38. The method of claim 1, wherein the sample is a blood plasma sample.

39. A system for evaluation of copy number of a nucleic acid sequence of interest in a test sample, the system comprising:
a sequencer for receiving nucleic acids from the test sample providing nucleic acid sequence information from the sample;
one or more processors; and
one or more computer-readable storage media having stored thereon instructions for execution on said processor to evaluate copy number in the test sample using a method comprising:
(a) providing, at the system, at least 10,000 sequence reads of the test sample;
(b) aligning, by the one or more processors, the at least 10,000 sequence reads of the test sample to a reference genome comprising the nucleic acid sequence of interest, thereby providing test sequence tags;
(c) determining, by the one or more processors, a coverage of the test sequence tags located in each bin, wherein each chromosome of the reference genome is divided into a plurality of bins;
(d) providing, by the one or more processors, a global profile for the nucleic acid sequence of interest, wherein the global profile comprises an expected coverage in each bin, and wherein the expected coverage is obtained from a training set of training samples unaffected by a copy number variation of the nucleic acid sequence of interest, the expected coverage exhibiting variation from bin to bin;
(e) adjusting, by the one or more processors, the coverage of the test sequence tags in each bin of at least the nucleic acid sequence of interest according to the expected coverage in each bin, thereby obtaining a global-profile-corrected coverage in each bin of the test sequence tags;
(f) adjusting, by the one or more processors, the global-profile-corrected coverages based on a relation between GC content level of the test sample and the global-profile-corrected coverage of the test sample for the bins of the test sequence tags, thereby obtaining a sample-GC-corrected coverage of the test sequence tags on the nucleic acid sequence of interest, wherein the adjusting is not based on GC-coverage relations of samples other than the test sample; and
(g) evaluating, by the one or more processors, copy number of the nucleic acid sequence of interest in the test sample based on the sample-GC-corrected coverage.

* * * * *